US007244411B2

(12) United States Patent
Núñez et al.

(10) Patent No.: US 7,244,411 B2
(45) Date of Patent: Jul. 17, 2007

(54) METHOD OF SELECTIVE PEPTIDE ISOLATION FOR THE IDENTIFICATION AND QUANTITATIVE ANALYSIS OF PROTEINS IN COMPLEX MIXTURES

(75) Inventors: Lázaro Hiram Betancourt Núñez, Ciudad de la Habana (CU); Jorge Fernández de Cossio Dorta-Duque, Ciudad de la Habana (CU); Vladimir Armando Besada Pérez, Ciudad de la Habana (CU); Jeovanis Gil Valdés, Ciudad de la Habana (CU); Luis Javier González López, Ciudad de la Habana (CU); Gabriel Ramón Padrón Palomares, Ciudad de la Habana (CU); Rolando Pajón Feyt, La Habana (CU); Félix Modesto Álvarez Gil, Ciudad de la Habana (CU)

(73) Assignee: Centro de Ingenieria Genetica y Biotecnologia, C. Habana (CU)

( * ) Notice: Subject to any disclaimer, the term of this patent is extended or adjusted under 35 U.S.C. 154(b) by 68 days.

(21) Appl. No.: 10/988,943

(22) Filed: Nov. 15, 2004

(65) Prior Publication Data

US 2005/0176085 A1 Aug. 11, 2005

(30) Foreign Application Priority Data

Nov. 19, 2003 (CU) .......................................... 1/03

(51) Int. Cl.
*A61K 51/00* (2006.01)
*A61M 36/14* (2006.01)

(52) U.S. Cl. .................................................... 424/1.69

(58) Field of Classification Search ..................... None
See application file for complete search history.

(56) References Cited

OTHER PUBLICATIONS

Berger et al. Anal. Chem. 2002;74:4994-5000.*
Zhu et al. Rapid Commun Mass Spectrom 1995;9(13):1315-1320.*
Dixon et al. Biochem J 1968;109:312-314.*
Hale et al. Analy. Biochem. 2000;287:110-117.*

* cited by examiner

*Primary Examiner*—Ralph Gitomer
*Assistant Examiner*—Bin Shen
(74) *Attorney, Agent, or Firm*—Hoffmann & Baron, LLP

(57) ABSTRACT

The present invention describes a method of selective peptide isolation for the identification and quantitative analysis of proteins in complex mixture. The method comprises the selective isolation from every protein of those peptides that neither contain arginine nor histidine (NHNR peptides), and the determination of the relative concentrations of one or several proteins in different samples from the ratio between the areas of the estimated theoretical spectra for the NHNR peptides labeled with different isotopes in each sample. The determination of the relative concentration of proteins is valid for any type of isotopic label of the NHNR peptides. The method avoids the separation and purification of the proteins present in a complex mixture, and the analysis of all peptides generated from the enzymatic digest of the samples. The method is applicable to the identification of proteins with vacunal, therapeutic and diagnostic aims.

11 Claims, 8 Drawing Sheets

100
%
0
654.35
725.84
810.11
888.43
908.46
1081.55
1214.69
500
600
700
800
900
1000
1100
1200
1300
1400
1500
m/z

SEQUENCE LISTING

```
<160> NUMBER OF SEQ ID NOS: 61

<210> SEQ ID NO 1
<211> LENGTH: 415
<212> TYPE: PRT
<213> ORGANISM: Streptococcus equisimilis

<400> SEQUENCE: 1

Met Ile Ala Gly Pro Glu Trp Leu Leu Asp Arg Pro Ser Val Asn Asn
  1               5                  10                  15

Ser Gln Leu Val Val Ser Val Ala Gly Thr Val Glu Gly Thr Asn Gln
            20                  25                  30

Asp Ile Ser Leu Lys Phe Phe Glu Ile Asp Leu Thr Ser Arg Pro Ala
        35                  40                  45

His Gly Gly Lys Thr Glu Gln Gly Leu Ser Pro Lys Ser Lys Pro Phe
     50                  55                  60

Ala Thr Asp Ser Gly Ala Met Pro His Lys Leu Glu Lys Ala Asp Leu
 65                  70                  75                  80

Leu Lys Ala Ile Gln Glu Gln Leu Ile Ala Asn Val His Ser Asn Asp
                85                  90                  95

Asp Tyr Phe Glu Val Ile Asp Phe Ala Ser Asp Ala Thr Ile Thr Asp
            100                 105                 110

Arg Asn Gly Lys Val Tyr Phe Ala Asp Lys Asp Gly Ser Val Thr Leu
```

```
        115                 120                 125

Pro Thr Gln Pro Val Gln Glu Phe Leu Leu Ser Gly His Val Arg Val
    130                 135                 140

Arg Pro Tyr Lys Glu Lys Pro Ile Gln Asn Gln Ala Lys Ser Val Asp
145                 150                 155                 160

Val Glu Tyr Thr Val Gln Phe Thr Pro Leu Asn Pro Asp Asp Asp Phe
                165                 170                 175

Arg Pro Gly Leu Lys Asp Thr Lys Leu Leu Lys Thr Leu Ala Ile Gly
            180                 185                 190

Asp Thr Ile Thr Ser Gln Glu Leu Leu Ala Gln Ala Gln Ser Ile Leu
        195                 200                 205

Asn Lys Thr His Pro Gly Tyr Thr Ile Tyr Glu Arg Asp Ser Ser Ile
    210                 215                 220

Val Thr His Asp Asn Asp Ile Phe Arg Thr Ile Leu Pro Met Asp Gln
225                 230                 235                 240

Glu Phe Thr Tyr His Val Lys Asn Arg Glu Gln Ala Tyr Glu Ile Asn
                245                 250                 255

Lys Lys Ser Gly Leu Asn Glu Glu Ile Asn Asn Thr Asp Leu Ile Ser
            260                 265                 270

Glu Lys Tyr Tyr Val Leu Lys Lys Gly Glu Lys Pro Tyr Asp Pro Phe
        275                 280                 285

Asp Arg Ser His Leu Lys Leu Phe Thr Ile Lys Tyr Val Asp Val Asn
    290                 295                 300

Thr Asn Glu Leu Leu Lys Ser Glu Gln Leu Leu Thr Ala Ser Glu Arg
305                 310                 315                 320

Asn Leu Asp Phe Arg Asp Leu Tyr Asp Pro Arg Asp Lys Ala Lys Leu
                325                 330                 335

Leu Tyr Asn Asn Leu Asp Ala Phe Gly Ile Met Asp Tyr Thr Leu Thr
            340                 345                 350

Gly Lys Val Glu Asp Asn His Asp Asp Thr Asn Arg Ile Ile Thr Val
        355                 360                 365

Tyr Met Gly Lys Arg Pro Glu Gly Glu Asn Ala Ser Tyr His Leu Ala
    370                 375                 380

Tyr Asp Lys Asp Arg Tyr Thr Glu Glu Glu Arg Glu Val Tyr Ser Tyr
385                 390                 395                 400

Leu Arg Tyr Thr Gly Thr Pro Ile Pro Asp Asn Pro Asn Asp Lys
                405                 410                 415


<210> SEQ ID NO 2
<211> LENGTH: 389
<212> TYPE: PRT
<213> ORGANISM: Neisseria meningitidis (group B)

<400> SEQUENCE: 2

Met Arg Lys Lys Leu Thr Ala Leu Val Leu Ser Ala Leu Pro Leu Ala
  1               5                  10                  15

Ala Val Ala Asp Val Ser Leu Tyr Gly Glu Ile Lys Ala Gly Val Glu
             20                  25                  30

Gly Arg Asn Tyr Gln Leu Gln Leu Thr Glu Ala Gln Ala Ala Asn Gly
         35                  40                  45

Gly Ala Ser Gly Gln Val Lys Val Thr Lys Ala Lys Ser Arg Ile Arg
     50                  55                  60

Thr Lys Ile Ser Asp Phe Gly Ser Phe Ile Gly Phe Lys Gly Ser Glu
 65                  70                  75                  80
```

-continued

```
Asp Leu Gly Glu Gly Leu Lys Ala Val Trp Gln Leu Glu Gln Asp Val
                85                  90                  95

Ser Val Ala Gly Gly Gly Ala Thr Gln Trp Gly Asn Arg Glu Ser Phe
            100                 105                 110

Ile Gly Leu Ala Gly Glu Phe Gly Thr Leu Arg Ala Gly Arg Val Ala
        115                 120                 125

Asn Gln Phe Asp Asp Ala Ser Gln Ala Ile Asp Pro Trp Asp Ser Asn
    130                 135                 140

Asn Asp Val Arg Ser Gln Leu Gly Ile Phe Lys Arg His Asp Asp Met
145                 150                 155                 160

Pro Val Ser Val Arg Tyr Asp Ser Pro Asp Phe Ser Gly Phe Ser Gly
                165                 170                 175

Ser Val Gln Phe Val Pro Ile Gln Asn Ser Lys Ser Ala Tyr Thr Pro
            180                 185                 190

Ala His Val Val Val Asn Asn Lys Val Ala Thr His Val Pro Ala Val
        195                 200                 205

Val Gly Lys Pro Gly Ser Asp Val Tyr Tyr Ala Gly Leu Asn Tyr Lys
    210                 215                 220

Asn Gly Gly Phe Ala Gly Asn Tyr Ala Phe Lys Tyr Ala Arg His Ala
225                 230                 235                 240

Asn Val Gly Arg Asn Ala Phe Glu Leu Phe Leu Ile Gly Ser Ala Thr
                245                 250                 255

Ser Asp Gln Ala Lys Gly Thr Asp Pro Leu Lys Asn His Gln Val His
            260                 265                 270

Arg Leu Thr Gly Gly Tyr Glu Glu Gly Gly Leu Asn Leu Ala Leu Ala
        275                 280                 285

Ala Gln Leu Asp Leu Ser Glu Asn Ala Asp Lys Thr Lys Asn Ser Thr
    290                 295                 300

Thr Glu Ile Ala Ala Thr Ala Ser Tyr Arg Phe Gly Asn Ala Val Pro
305                 310                 315                 320

Arg Ile Ser Tyr Ala His Gly Phe Asp Leu Ile Glu Arg Gly Lys Lys
                325                 330                 335

Gly Glu Asn Thr Ser Tyr Asp Gln Ile Ile Ala Gly Val Asp Tyr Asp
            340                 345                 350

Phe Ser Lys Arg Thr Ser Ala Ile Val Ser Gly Ala Trp Leu Lys Arg
        355                 360                 365

Asn Thr Gly Ile Gly Asn Tyr Thr Gln Ile Asn Ala Ala Ser Val Gly
    370                 375                 380

Leu Arg His Lys Phe
385


<210> SEQ ID NO 3
<211> LENGTH: 331
<212> TYPE: PRT
<213> ORGANISM: Neisseria meningitidis (group B)

<400> SEQUENCE: 3

Met Lys Lys Ser Leu Ile Ala Leu Thr Leu Ala Ala Leu Pro Val Ala
  1               5                  10                  15

Ala Met Ala Asp Val Thr Leu Tyr Gly Thr Ile Lys Ala Gly Val Glu
             20                  25                  30

Thr Ser Arg Ser Val Phe His Gln Asn Gly Gln Val Thr Glu Val Thr
         35                  40                  45

Thr Ala Thr Gly Ile Val Asp Leu Gly Ser Lys Ile Gly Phe Lys Gly
     50                  55                  60
```

-continued

```
Gln Glu Asp Leu Gly Asn Gly Leu Lys Ala Ile Trp Gln Val Glu Gln
 65                  70                  75                  80

Lys Ala Ser Ile Ala Gly Thr Asp Ser Gly Trp Gly Asn Arg Gln Ser
                 85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
        115                 120                 125

Ser Asp Tyr Leu Gly Val Asn Lys Ile Ala Glu Pro Glu Ala Arg Leu
    130                 135                 140

Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His His Gln Val Gln Glu Gly Leu Asn Ile
        195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Leu Val Asp Asp Ala Asp Ile Gly Asn Glu Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330


<210> SEQ ID NO 4
<211> LENGTH: 252
<212> TYPE: PRT
<213> ORGANISM: Neisseria meningitidis (group B)

<400> SEQUENCE: 4

Ala Gln Glu Leu Gln Thr Ala Asn Glu Phe Thr Val His Thr Asp Leu
  1               5                  10                  15

Ser Ser Ile Ser Ser Thr Arg Ala Phe Leu Lys Glu Lys His Lys Ala
             20                  25                  30

Ala Lys His Ile Ser Val Arg Ala Asp Ile Pro Phe Asp Ala Asn Gln
         35                  40                  45

Gly Ile Arg Leu Glu Ala Gly Phe Gly Arg Ser Lys Lys Asn Ile Ile
     50                  55                  60

Asn Leu Glu Thr Asp Glu Asn Lys Leu Gly Lys Thr Lys Asn Val Lys
 65                  70                  75                  80

Leu Pro Thr Gly Val Pro Glu Asn Arg Ile Asp Leu Tyr Thr Gly Tyr
                 85                  90                  95

Thr Tyr Thr Gln Thr Leu Ser Asp Ser Leu Asn Phe Arg Val Gly Ala
```

-continued

```
            100                 105                 110

Gly Leu Gly Phe Glu Ser Ser Lys Asp Ser Ile Lys Thr Thr Lys His
        115                 120                 125

Thr Leu His Ser Ser Arg Gln Ser Trp Leu Ala Lys Val His Ala Asp
    130                 135                 140

Leu Leu Ser Gln Leu Gly Asn Gly Trp Tyr Ile Asn Pro Trp Ser Glu
145                 150                 155                 160

Val Lys Phe Asp Leu Asn Ser Arg Tyr Lys Leu Asn Thr Gly Val Thr
                165                 170                 175

Asn Leu Lys Lys Asp Ile Asn Gln Lys Thr Asn Gly Trp Gly Phe Gly
            180                 185                 190

Leu Gly Ala Asn Ile Gly Lys Lys Leu Gly Glu Ser Ala Ser Ile Glu
        195                 200                 205

Ala Gly Pro Phe Tyr Lys Gln Arg Thr Tyr Lys Glu Ser Gly Glu Phe
    210                 215                 220

Ser Val Thr Thr Lys Ser Gly Asp Val Ser Leu Thr Ile Pro Lys Thr
225                 230                 235                 240

Ser Ile Arg Glu Tyr Gly Leu Arg Val Gly Ile Lys
                245                 250


<210> SEQ ID NO 5
<211> LENGTH: 594
<212> TYPE: PRT
<213> ORGANISM: Neisseria meningitidis (group B)

<400> SEQUENCE: 5

Met Ala Leu Val Glu Leu Lys Val Pro Asp Ile Gly Gly His Glu Asn
  1               5                  10                  15

Val Asp Ile Ile Ala Val Glu Val Asn Val Gly Asp Thr Ile Ala Val
            20                  25                  30

Asp Asp Thr Leu Ile Thr Leu Glu Thr Asp Lys Ala Thr Met Asp Val
        35                  40                  45

Pro Ala Glu Val Ala Gly Val Val Lys Glu Val Lys Val Lys Val Gly
     50                  55                  60

Asp Lys Ile Ser Glu Gly Gly Leu Ile Val Val Val Glu Ala Glu Gly
 65                  70                  75                  80

Thr Ala Ala Ala Pro Lys Ala Glu Ala Ala Ala Ala Pro Ala Gln Glu
                 85                  90                  95

Ala Pro Lys Ala Ala Ala Pro Ala Pro Gln Ala Ala Gln Phe Gly Gly
            100                 105                 110

Ser Ala Asp Ala Glu Tyr Asp Val Val Val Leu Gly Gly Gly Pro Gly
        115                 120                 125

Gly Tyr Ser Ala Ala Phe Ala Ala Ala Asp Glu Gly Leu Lys Val Ala
    130                 135                 140

Ile Val Glu Arg Tyr Lys Thr Leu Gly Gly Val Cys Leu Asn Val Gly
145                 150                 155                 160

Cys Ile Pro Ser Lys Ala Leu Leu His Asn Ala Ala Val Ile Asp Glu
                165                 170                 175

Val Arg His Leu Ala Ala Asn Gly Ile Lys Tyr Pro Glu Pro Glu Leu
            180                 185                 190

Asp Ile Asp Met Leu Arg Ala Tyr Lys Asp Gly Val Val Ser Arg Leu
        195                 200                 205

Thr Gly Gly Leu Ala Gly Met Ala Lys Ser Arg Lys Val Asp Val Ile
    210                 215                 220
```

-continued

```
Gln Gly Asp Gly Gln Phe Leu Asp Pro His His Leu Glu Val Ser Leu
225                 230                 235                 240

Thr Ala Gly Asp Ala Tyr Glu Gln Ala Ala Pro Thr Gly Glu Lys Lys
                245                 250                 255

Ile Val Ala Phe Lys Asn Cys Ile Ile Ala Ala Gly Ser Arg Val Thr
            260                 265                 270

Lys Leu Pro Phe Ile Pro Glu Asp Pro Arg Ile Ile Asp Ser Ser Gly
        275                 280                 285

Ala Leu Ala Leu Lys Glu Val Pro Gly Lys Leu Leu Ile Ile Gly Gly
    290                 295                 300

Gly Ile Ile Gly Leu Glu Met Gly Thr Val Tyr Ser Thr Leu Gly Ser
305                 310                 315                 320

Arg Leu Asp Val Val Glu Met Met Asp Gly Leu Met Gln Gly Ala Asp
                325                 330                 335

Arg Asp Leu Val Lys Val Trp Gln Lys Gln Asn Glu Tyr Arg Phe Asp
            340                 345                 350

Asn Ile Met Val Asn Thr Lys Thr Val Ala Val Glu Pro Lys Glu Asp
        355                 360                 365

Gly Val Tyr Val Thr Phe Glu Gly Ala Asn Ala Pro Lys Glu Pro Gln
    370                 375                 380

Arg Tyr Asp Ala Val Leu Val Ala Ala Gly Arg Ala Pro Asn Gly Lys
385                 390                 395                 400

Leu Ile Ser Ala Glu Lys Ala Gly Val Ala Val Thr Asp Arg Gly Phe
                405                 410                 415

Ile Glu Val Asp Lys Gln Met Arg Thr Asn Val Pro His Ile Tyr Ala
            420                 425                 430

Ile Gly Asp Ile Val Gly Gln Pro Met Leu Ala His Lys Ala Val His
        435                 440                 445

Glu Gly His Val Ala Ala Glu Asn Cys Ala Gly His Lys Ala Tyr Phe
    450                 455                 460

Asp Ala Arg Val Ile Pro Gly Val Ala Tyr Thr Ser Pro Glu Val Ala
465                 470                 475                 480

Trp Val Gly Glu Thr Glu Leu Ser Ala Lys Ala Ser Gly Arg Lys Ile
                485                 490                 495

Thr Lys Ala Asn Phe Pro Trp Ala Ala Ser Gly Arg Ala Ile Ala Asn
            500                 505                 510

Gly Cys Asp Lys Pro Phe Thr Lys Leu Ile Phe Asp Ala Glu Thr Gly
        515                 520                 525

Arg Ile Ile Gly Gly Gly Ile Val Gly Pro Asn Gly Gly Asp Met Ile
    530                 535                 540

Gly Glu Val Cys Leu Ala Ile Glu Met Gly Cys Asp Ala Ala Asp Ile
545                 550                 555                 560

Gly Lys Thr Ile His Pro His Pro Thr Leu Gly Glu Ser Ile Gly Met
                565                 570                 575

Ala Ala Glu Val Ala Leu Gly Thr Cys Thr Asp Leu Pro Pro Gln Lys
            580                 585                 590

Lys Lys


<210> SEQ ID NO 6
<211> LENGTH: 242
<212> TYPE: PRT
<213> ORGANISM: Neisseria meningitidis (group B)

<400> SEQUENCE: 6
```

-continued

```
Met Thr Lys Gln Leu Lys Leu Ser Ala Leu Phe Val Ala Leu Leu Ala
  1               5                  10                  15

Ser Gly Thr Ala Val Ala Gly Glu Ala Ser Val Gln Gly Tyr Thr Val
             20                  25                  30

Ser Gly Gln Ser Asn Glu Ile Val Arg Asn Asn Tyr Gly Glu Cys Trp
         35                  40                  45

Lys Asn Ala Tyr Phe Asp Lys Ala Ser Gln Gly Arg Val Glu Cys Gly
     50                  55                  60

Asp Ala Val Ala Ala Pro Glu Pro Glu Pro Glu Pro Glu Pro Ala Pro
 65                  70                  75                  80

Ala Pro Val Val Val Val Glu Gln Ala Pro Gln Tyr Val Asp Glu Thr
                 85                  90                  95

Ile Ser Leu Ser Ala Lys Thr Leu Phe Gly Phe Asp Lys Asp Ser Leu
            100                 105                 110

Arg Ala Glu Ala Gln Asp Asn Leu Lys Val Leu Ala Gln Arg Leu Gly
        115                 120                 125

Gln Thr Asn Ile Gln Ser Val Arg Val Glu Gly His Thr Asp Phe Met
    130                 135                 140

Gly Ser Asp Lys Tyr Asn Gln Ala Leu Ser Glu Arg Arg Ala Tyr Val
145                 150                 155                 160

Val Ala Asn Asn Leu Val Ser Asn Gly Val Pro Val Ser Arg Ile Ser
                165                 170                 175

Ala Val Gly Leu Gly Glu Ser Gln Ala Gln Met Thr Gln Val Cys Glu
            180                 185                 190

Ala Glu Val Ala Lys Leu Gly Ala Lys Val Ser Lys Ala Lys Lys Arg
        195                 200                 205

Glu Ala Leu Ile Ala Cys Ile Glu Pro Asp Arg Arg Val Asp Val Lys
    210                 215                 220

Ile Arg Ser Ile Val Thr Arg Gln Val Val Pro Ala His Asn His His
225                 230                 235                 240

Gln His


<210> SEQ ID NO 7
<211> LENGTH: 797
<212> TYPE: PRT
<213> ORGANISM: Neisseria meningitidis (group B)

<400> SEQUENCE: 7

Met Lys Leu Lys Gln Ile Ala Ser Ala Leu Met Met Leu Gly Ile Ser
  1               5                  10                  15

Pro Leu Ala Leu Ala Asp Phe Thr Ile Gln Asp Ile Arg Val Glu Gly
             20                  25                  30

Leu Gln Arg Thr Glu Pro Ser Thr Val Phe Asn Tyr Leu Pro Val Lys
         35                  40                  45

Val Gly Asp Thr Tyr Asn Asp Thr His Gly Ser Ala Ile Ile Lys Ser
     50                  55                  60

Leu Tyr Ala Thr Gly Phe Phe Asp Asp Val Arg Val Glu Thr Ala Asp
 65                  70                  75                  80

Gly Gln Leu Leu Leu Thr Val Ile Glu Arg Pro Thr Ile Gly Ser Leu
                 85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125
```

-continued

```
Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Thr Ala Gly
            500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
    530                 535                 540

Pro Lys His Tyr Ala Asp Phe Ile Lys Lys Tyr Gly Lys Thr Asp Gly
```

```
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
    610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
        755                 760                 765

Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795


<210> SEQ ID NO 8
<211> LENGTH: 714
<212> TYPE: PRT
<213> ORGANISM: Neisseria meningitidis (group B)

<400> SEQUENCE: 8

Met Asn Thr Pro Leu Phe Arg Leu Ser Leu Leu Ser Leu Thr Leu Ala
  1               5                  10                  15

Ala Gly Phe Ala His Ala Ala Glu Asn Asn Ala Lys Val Val Leu Asp
             20                  25                  30

Thr Val Thr Val Lys Gly Asp Arg Gln Gly Ser Lys Ile Arg Thr Asn
         35                  40                  45

Ile Val Thr Leu Gln Gln Lys Asp Glu Ser Thr Ala Thr Asp Met Arg
     50                  55                  60

Glu Leu Leu Lys Glu Glu Pro Ser Ile Asp Phe Gly Gly Gly Asn Gly
 65                  70                  75                  80

Thr Ser Gln Phe Leu Thr Leu Arg Gly Met Gly Gln Asn Ser Val Asp
                 85                  90                  95

Ile Lys Val Asp Asn Ala Tyr Ser Asp Ser Gln Ile Leu Tyr His Gln
            100                 105                 110

Gly Arg Phe Ile Val Asp Pro Ala Leu Val Lys Val Val Ser Val Gln
        115                 120                 125
```

-continued

```
Lys Gly Ala Gly Ser Ala Ser Ala Gly Ile Gly Ala Thr Asn Gly Ala
    130                 135                 140

Ile Ile Thr Lys Thr Val Asp Ala Gln Asp Leu Leu Lys Gly Leu Asp
145                 150                 155                 160

Lys Asn Trp Gly Val Arg Leu Asn Ser Gly Phe Ala Ser Asn Glu Gly
                165                 170                 175

Val Ser Tyr Gly Ala Ser Val Phe Gly Lys Glu Gly Asn Phe Asp Gly
            180                 185                 190

Leu Phe Ser Tyr Asn Arg Asn Asn Glu Lys Asp Tyr Glu Ala Gly Lys
        195                 200                 205

Gly Phe Arg Asn Asn Phe Asn Gly Gly Lys Thr Val Pro Tyr Ser Ala
    210                 215                 220

Leu Asp Lys Arg Ser Tyr Leu Ala Lys Ile Gly Thr Ser Phe Gly Asp
225                 230                 235                 240

Gly Asp His Arg Ile Val Leu Ser His Met Lys Asp Gln His Arg Gly
                245                 250                 255

Ile Arg Thr Val Arg Glu Glu Phe Thr Val Gly Gly Asp Lys Glu Arg
            260                 265                 270

Ile Ser Met Glu Arg Gln Ala Pro Ala Tyr Arg Glu Thr Thr Gln Ser
        275                 280                 285

Asn Thr Asn Leu Ala Tyr Thr Gly Lys Asn Leu Gly Phe Val Glu Lys
    290                 295                 300

Leu Asp Ala Asn Ala Tyr Val Leu Glu Lys Glu Arg Tyr Ser Ala Asp
305                 310                 315                 320

Asp Ser Gly Thr Gly Tyr Ala Gly Asn Val Lys Gly Pro Asn His Thr
                325                 330                 335

Gln Ile Thr Thr Arg Gly Met Asn Phe Asn Phe Asp Ser Arg Leu Ala
            340                 345                 350

Glu Gln Thr Leu Leu Lys Tyr Gly Ile Asn Tyr Arg His Gln Glu Ile
        355                 360                 365

Lys Pro Gln Ala Phe Leu Asn Ser Gln Phe Lys Ile Glu Asp Lys Glu
    370                 375                 380

Lys Ala Thr Asp Glu Glu Lys Asn Lys Asn Arg Glu Asn Glu Lys Ile
385                 390                 395                 400

Ala Lys Ala Tyr Arg Leu Thr Asn Pro Thr Lys Thr Asp Thr Gly Ala
                405                 410                 415

Tyr Ile Glu Ala Ile His Glu Ile Asp Gly Phe Thr Leu Thr Gly Gly
            420                 425                 430

Leu Arg Tyr Asp Arg Phe Lys Val Lys Thr His Asp Gly Lys Thr Val
        435                 440                 445

Ser Ser Asn Asn Leu Asn Pro Ser Phe Gly Val Ile Trp Gln Pro His
    450                 455                 460

Glu His Trp Ser Phe Ser Ala Ser His Asn Tyr Ala Ser Arg Ser Pro
465                 470                 475                 480

Arg Leu Tyr Asp Ala Leu Gln Thr His Gly Lys Arg Gly Ile Ile Ser
                485                 490                 495

Ile Ala Asp Gly Thr Lys Ala Glu Arg Ala Arg Asn Thr Glu Ile Gly
            500                 505                 510

Phe Asn Tyr Asn Asp Gly Thr Phe Ala Ala Asn Gly Ser Tyr Phe Trp
        515                 520                 525

Gln Thr Ile Lys Asp Ala Leu Ala Asn Pro Gln Asn Arg His Asp Ser
    530                 535                 540

Val Ala Val Arg Glu Ala Val Asn Ala Gly Tyr Ile Lys Asn His Gly
```

-continued

```
545                 550                 555                 560

Tyr Glu Leu Gly Ala Ser Tyr Arg Thr Gly Gly Leu Thr Ala Lys Val
                565                 570                 575

Gly Val Ser His Ser Lys Pro Arg Phe Tyr Asp Thr His Lys Asp Lys
            580                 585                 590

Leu Leu Ser Ala Asn Pro Glu Phe Gly Ala Gln Val Gly Arg Thr Trp
        595                 600                 605

Thr Ala Ser Leu Ala Tyr Arg Phe Gln Asn Pro Asn Leu Glu Ile Gly
    610                 615                 620

Trp Arg Gly Arg Tyr Val Gln Lys Ala Val Gly Ser Ile Leu Val Ala
625                 630                 635                 640

Gly Gln Lys Asp Arg Asn Gly Lys Leu Glu Asn Val Val Arg Lys Gly
                645                 650                 655

Phe Gly Val Asn Asp Val Phe Ala Asn Trp Lys Pro Leu Gly Lys Asp
            660                 665                 670

Thr Leu Asn Val Asn Leu Ser Val Asn Asn Val Phe Asn Thr Phe Tyr
        675                 680                 685

Tyr Pro His Ser Gln Arg Trp Thr Asn Thr Leu Pro Gly Val Gly Arg
    690                 695                 700

Asp Val Arg Leu Gly Val Asn Tyr Lys Phe
705                 710


<210> SEQ ID NO 9
<211> LENGTH: 331
<212> TYPE: PRT
<213> ORGANISM: Neisseria meningitidis (group B)

<400> SEQUENCE: 9

Met Lys Thr Ser Ile Arg Tyr Ala Leu Leu Ala Ala Ala Leu Thr Ala
  1               5                  10                  15

Ala Thr Pro Ala Leu Ala Asp Ile Thr Val Tyr Asn Gly Gln His Lys
             20                  25                  30

Glu Ala Ala Gln Ala Val Ala Asp Ala Phe Thr Arg Ala Thr Gly Ile
         35                  40                  45

Lys Val Lys Leu Asn Ser Ala Lys Gly Asp Gln Leu Ala Gly Gln Ile
     50                  55                  60

Lys Glu Glu Gly Ser Arg Ser Pro Ala Asp Val Phe Tyr Ser Glu Gln
 65                  70                  75                  80

Ile Pro Ala Leu Ala Thr Leu Ser Ala Ala Asn Leu Leu Glu Pro Leu
                 85                  90                  95

Pro Ala Ser Thr Ile Asn Glu Thr Arg Gly Lys Gly Val Pro Val Ala
            100                 105                 110

Ala Lys Lys Asp Trp Val Ala Leu Ser Gly Arg Ser Arg Val Val Val
        115                 120                 125

Tyr Asp Thr Arg Lys Leu Ser Glu Lys Asp Leu Glu Lys Ser Val Leu
    130                 135                 140

Asn Tyr Ala Thr Pro Lys Trp Lys Asn Arg Ile Gly Tyr Ala Pro Thr
145                 150                 155                 160

Ser Gly Ala Phe Leu Glu Gln Val Val Ala Ile Val Lys Leu Lys Gly
                165                 170                 175

Glu Ala Ala Ala Leu Lys Trp Leu Lys Gly Leu Lys Glu Tyr Gly Lys
            180                 185                 190

Pro Tyr Ala Lys Asn Ser Val Ala Leu Gln Ala Val Glu Asn Gly Glu
        195                 200                 205
```

-continued

```
Ile Asp Ala Ala Leu Ile Asn Asn Tyr Tyr Trp His Ala Phe Ala Arg
    210                 215                 220

Glu Lys Gly Val Gln Asn Val His Thr Arg Leu Asn Phe Val Arg His
225                 230                 235                 240

Arg Asp Pro Gly Ala Leu Val Thr Tyr Ser Gly Ala Ala Val Leu Lys
                245                 250                 255

Ser Ser Gln Asn Lys Asp Glu Ala Lys Lys Phe Val Ala Phe Leu Ala
            260                 265                 270

Ser Lys Glu Gly Gln Arg Ala Leu Thr Ala Val Arg Ala Glu Tyr Pro
        275                 280                 285

Leu Asn Pro His Val Val Ser Thr Phe Asn Leu Glu Pro Ile Ala Lys
    290                 295                 300

Leu Glu Ala Pro Gln Val Ser Ala Thr Thr Val Ser Glu Lys Glu His
305                 310                 315                 320

Ala Thr Arg Leu Leu Glu Gln Ala Gly Met Lys
                325                 330


<210> SEQ ID NO 10
<211> LENGTH: 911
<212> TYPE: PRT
<213> ORGANISM: Neisseria meningitidis (group B)

<400> SEQUENCE: 10

Met Gln Gln Gln His Leu Phe Arg Leu Asn Ile Leu Cys Leu Ser Leu
  1               5                  10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
     50                  55                  60

Ala Asp Thr Leu Ser Lys Glu Gln Val Leu Asp Ile Arg Asp Leu Thr
 65                  70                  75                  80

Arg Tyr Asp Pro Gly Ile Ala Val Val Glu Gln Gly Arg Gly Ala Ser
                 85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Glu Tyr Ala
                245                 250                 255
```

-continued

```
Tyr Phe Ile Val Glu Asp Glu Cys Glu Gly Lys Asn Tyr Glu Thr Cys
            260                 265                 270

Lys Ser Lys Pro Lys Lys Asp Val Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Ser Lys Gln Ala Gly Ser Leu Pro Gly Asn Gly
        355                 360                 365

Lys Tyr Ala Gly Asn His Lys Tyr Gly Gly Leu Phe Thr Asn Gly Glu
    370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Asp Ser Asn Leu Arg His
            500                 505                 510

Gln Asp Tyr Tyr Tyr Gln His Ala Asn Arg Ala Tyr Ser Ser Lys Thr
        515                 520                 525

Pro Pro Lys Thr Ala Asn Pro Asn Gly Asp Lys Ser Lys Pro Tyr Trp
    530                 535                 540

Val Ser Ile Gly Gly Gly Asn Val Val Thr Gly Gln Ile Cys Leu Phe
545                 550                 555                 560

Gly Asn Asn Thr Tyr Thr Asp Cys Thr Pro Arg Ser Ile Asn Gly Lys
                565                 570                 575

Ser Tyr Tyr Ala Ala Val Arg Asp Asn Val Arg Leu Gly Arg Trp Ala
            580                 585                 590

Asp Val Gly Ala Gly Leu Arg Tyr Asp Tyr Arg Ser Thr His Ser Asp
        595                 600                 605

Asp Gly Ser Val Ser Thr Gly Thr His Arg Thr Leu Ser Trp Asn Ala
    610                 615                 620

Gly Ile Val Leu Lys Pro Ala Asp Trp Leu Asp Leu Thr Tyr Arg Thr
625                 630                 635                 640

Ser Thr Gly Phe Arg Leu Pro Ser Phe Ala Glu Met Tyr Gly Trp Arg
                645                 650                 655

Ser Gly Val Gln Ser Lys Ala Val Lys Ile Asp Pro Glu Lys Ser Phe
            660                 665                 670
```

-continued

```
Asn Lys Glu Ala Gly Ile Val Phe Lys Gly Asp Phe Gly Asn Leu Glu
        675                 680                 685

Ala Ser Trp Phe Asn Asn Ala Tyr Arg Asp Leu Ile Val Arg Gly Tyr
    690                 695                 700

Glu Ala Gln Ile Lys Asn Gly Lys Glu Glu Ala Lys Gly Asp Pro Ala
705                 710                 715                 720

Tyr Leu Asn Ala Gln Ser Ala Arg Ile Thr Gly Ile Asn Ile Leu Gly
                725                 730                 735

Lys Ile Asp Trp Asn Gly Val Trp Asp Lys Leu Pro Glu Gly Trp Tyr
            740                 745                 750

Ser Thr Phe Ala Tyr Asn Arg Val His Val Arg Asp Ile Lys Lys Arg
        755                 760                 765

Ala Asp Arg Thr Asp Ile Gln Ser His Leu Phe Asp Ala Ile Gln Pro
    770                 775                 780

Ser Arg Tyr Val Val Gly Leu Gly Tyr Asp Gln Pro Glu Gly Lys Trp
785                 790                 795                 800

Gly Val Asn Gly Met Leu Thr Tyr Ser Lys Ala Lys Glu Ile Thr Glu
                805                 810                 815

Leu Leu Gly Ser Arg Ala Leu Leu Asn Gly Asn Ser Arg Asn Thr Lys
            820                 825                 830

Ala Thr Ala Arg Arg Thr Arg Pro Trp Tyr Ile Val Asp Val Ser Gly
        835                 840                 845

Tyr Tyr Thr Ile Lys Lys His Phe Thr Leu Arg Ala Gly Val Tyr Asn
    850                 855                 860

Leu Leu Asn Tyr Arg Tyr Val Thr Trp Glu Asn Val Arg Gln Thr Ala
865                 870                 875                 880

Gly Gly Ala Val Asn Gln His Lys Asn Val Gly Val Tyr Asn Arg Tyr
                885                 890                 895

Ala Ala Pro Gly Arg Asn Tyr Thr Phe Ser Leu Glu Met Lys Phe
            900                 905                 910


<210> SEQ ID NO 11
<211> LENGTH: 943
<212> TYPE: PRT
<213> ORGANISM: Neisseria meningitidis (group B)

<400> SEQUENCE: 11

Met Asn Lys Lys His Gly Phe Gln Leu Thr Leu Thr Ala Leu Ala Val
  1               5                  10                  15

Ala Ala Ala Phe Pro Ser Tyr Ala Ala Asn Pro Glu Thr Ala Ala Pro
             20                  25                  30

Asp Ala Ala Gln Thr Gln Ser Leu Lys Glu Val Thr Val Arg Ala Ala
         35                  40                  45

Lys Val Gly Arg Arg Ser Lys Glu Ala Thr Gly Leu Gly Lys Ile Val
     50                  55                  60

Lys Thr Ser Glu Thr Leu Asn Lys Glu Gln Val Leu Gly Ile Arg Asp
 65                  70                  75                  80

Leu Thr Arg Tyr Asp Pro Gly Val Ala Val Val Glu Gln Gly Asn Gly
                 85                  90                  95

Ala Ser Gly Gly Tyr Ser Ile Arg Gly Val Asp Lys Asn Arg Val Ala
            100                 105                 110

Val Ser Val Asp Gly Val Ala Gln Ile Gln Ala Phe Thr Val Gln Gly
        115                 120                 125

Ser Leu Ser Gly Tyr Gly Gly Arg Gly Gly Ser Gly Ala Ile Asn Glu
    130                 135                 140
```

-continued

```
Ile Glu Tyr Glu Asn Ile Ser Thr Val Glu Ile Asp Lys Gly Ala Gly
145                 150                 155                 160

Ser Ser Asp His Gly Ser Gly Ala Leu Gly Gly Ala Val Ala Phe Arg
                165                 170                 175

Thr Lys Glu Ala Ala Asp Leu Ile Ser Asp Gly Lys Ser Trp Gly Ile
            180                 185                 190

Gln Ala Lys Thr Ala Tyr Gly Ser Lys Asn Arg Gln Phe Met Lys Ser
        195                 200                 205

Leu Gly Ala Gly Phe Ser Lys Asp Gly Trp Glu Gly Leu Leu Ile Arg
    210                 215                 220

Thr Glu Arg Gln Gly Arg Glu Thr His Pro His Gly Asp Ile Ala Asp
225                 230                 235                 240

Gly Val Ala Tyr Gly Ile Asn Arg Leu Asp Ala Phe Arg Gln Thr Tyr
                245                 250                 255

Gly Ile Lys Lys Pro Ser Glu Gly Gly Glu Tyr Phe Leu Ala Glu Gly
            260                 265                 270

Glu Ser Glu Leu Lys Pro Val Ala Lys Val Ala Gly Asn Gly Asn Tyr
        275                 280                 285

Leu Asn Asn Gln Leu Asn Arg Trp Val Lys Glu Arg Ile Glu Gln Asn
    290                 295                 300

Gln Pro Leu Ser Ala Glu Glu Glu Ala Met Val Arg Glu Ala Gln Ala
305                 310                 315                 320

Arg His Glu Asn Leu Ser Ala Gln Ala Tyr Thr Gly Gly Gly Arg Ile
                325                 330                 335

Leu Pro Asp Pro Met Asp Tyr Arg Ser Gly Ser Trp Leu Ala Lys Leu
            340                 345                 350

Gly Tyr Arg Phe Gly Gly Arg His Tyr Val Gly Gly Val Phe Glu Asp
        355                 360                 365

Thr Lys Gln Arg Tyr Asp Ile Arg Asp Met Thr Glu Lys Gln Tyr Tyr
    370                 375                 380

Gly Thr Asp Glu Ala Lys Lys Phe Arg Asp Lys Ser Gly Val Tyr Asp
385                 390                 395                 400

Gly Asp Asp Phe Arg Asp Gly Leu Tyr Phe Val Pro Asn Ile Glu Glu
                405                 410                 415

Trp Lys Gly Asp Gln Lys Leu Ile Arg Gly Ile Gly Leu Lys Tyr Ser
            420                 425                 430

Arg Thr Lys Phe Ile Asp Glu His His Arg Arg Arg Arg Met Gly Leu
        435                 440                 445

Leu Tyr Arg Tyr Glu Asn Glu Lys Tyr Ser Asp Asn Trp Ala Asp Lys
    450                 455                 460

Ala Val Leu Ser Phe Asp Lys Gln Gly Val Ala Thr Asp Asn Asn Thr
465                 470                 475                 480

Leu Lys Leu Asn Cys Ala Val Tyr Pro Ala Val Asp Lys Ser Cys Arg
                485                 490                 495

Ala Ser Ala Asp Lys Pro Tyr Ser Tyr Asp Ser Ser Asp Arg Phe His
            500                 505                 510

Tyr Arg Glu Gln His Asn Val Leu Asn Ala Ser Phe Glu Lys Ser Leu
        515                 520                 525

Lys Asn Lys Trp Thr Lys His His Leu Thr Leu Gly Phe Gly Tyr Asp
    530                 535                 540

Ala Ser Asn Ala Ile Ser Arg Pro Glu Gln Leu Ser His Asn Ala Ala
545                 550                 555                 560
```

```
Arg Ile Ser Glu Tyr Ser Asp Tyr Thr Asp Lys Gly Asp Lys Tyr Leu
                565                 570                 575

Leu Gly Lys Pro Glu Val Val Glu Gly Ser Val Cys Gly Tyr Ile Glu
            580                 585                 590

Thr Leu Arg Ser Arg Lys Cys Val Pro Arg Lys Ile Asn Gly Ser Asn
        595                 600                 605

Ile His Ile Ser Leu Asn Asp Arg Phe Ser Ile Gly Lys Tyr Phe Asp
    610                 615                 620

Phe Ser Ser Gly Gly Arg Tyr Asp Arg Lys Asn Phe Thr Thr Ser Glu
625                 630                 635                 640

Glu Leu Val Arg Ser Gly Arg Tyr Val Asp Arg Ser Trp Asn Ser Gly
                645                 650                 655

Ile Val Phe Lys Pro Asn Arg His Phe Ser Leu Ser Tyr Arg Ala Ser
            660                 665                 670

Ser Gly Phe Arg Thr Pro Ser Phe Gln Glu Leu Phe Gly Ile Asp Ile
        675                 680                 685

Tyr His Asp Tyr Pro Lys Gly Trp Gln Arg Pro Ala Leu Lys Ser Glu
    690                 695                 700

Lys Ala Ala Asn Arg Glu Ile Gly Leu Gln Trp Lys Gly Asp Phe Gly
705                 710                 715                 720

Phe Leu Glu Ile Ser Ser Phe Arg Asn Arg Tyr Thr Asp Met Ile Ala
                725                 730                 735

Val Ala Asp His Lys Thr Lys Leu Pro Asn Gln Ala Gly Gln Leu Thr
            740                 745                 750

Glu Ile Asp Ile Arg Asp Tyr Tyr Asn Ala Gln Asn Met Ser Leu Gln
        755                 760                 765

Gly Val Asn Ile Leu Gly Lys Ile Asp Trp Asn Gly Val Tyr Gly Lys
    770                 775                 780

Leu Pro Glu Gly Leu Tyr Thr Thr Leu Ala Tyr Asn Arg Ile Lys Pro
785                 790                 795                 800

Lys Ser Val Ser Asn Arg Pro Gly Leu Ser Leu Arg Ser Tyr Ala Leu
                805                 810                 815

Asp Ala Val Gln Pro Ser Arg Tyr Val Leu Gly Phe Gly Tyr Asp Gln
            820                 825                 830

Pro Glu Gly Lys Trp Gly Ala Asn Ile Met Leu Thr Tyr Ser Lys Gly
        835                 840                 845

Lys Asn Pro Asp Glu Leu Ala Tyr Leu Ala Gly Asp Gln Lys Arg Tyr
    850                 855                 860

Ser Thr Lys Arg Ala Ser Ser Ser Trp Ser Thr Ala Asp Val Ser Ala
865                 870                 875                 880

Tyr Leu Asn Leu Lys Lys Arg Leu Thr Leu Arg Ala Ala Ile Tyr Asn
                885                 890                 895

Ile Gly Asn Tyr Arg Tyr Val Thr Trp Glu Ser Leu Arg Gln Thr Ala
            900                 905                 910

Glu Ser Thr Ala Asn Arg His Gly Gly Asp Ser Asn Tyr Gly Arg Tyr
        915                 920                 925

Ala Ala Pro Gly Arg Asn Phe Ser Leu Ala Leu Glu Met Lys Phe
    930                 935                 940
```

<210> SEQ ID NO 12
<211> LENGTH: 791
<212> TYPE: PRT
<213> ORGANISM: Neisseria meningitidis (group B)

<400> SEQUENCE: 12

-continued

```
Met Lys Pro Leu Gln Met Leu Pro Ile Ala Ala Leu Val Gly Ser Ile
 1               5                  10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
 65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Asn
    210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr His Ser Phe
                245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
        275                 280                 285

Asn Leu Thr Ala Ser Ser Trp Arg Glu Ala Asp Asp Val Asn Arg Arg
    290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Val Asn Asn Lys Gly Ser Phe Pro Met Asp Tyr Ser Thr Trp Thr Arg
            340                 345                 350

Asn Tyr Asn Gln Lys Asp Leu Asp Glu Ile Tyr Asn Arg Ser Met Asp
        355                 360                 365

Thr Arg Phe Lys Arg Phe Thr Leu Arg Leu Asp Ser His Pro Leu Gln
    370                 375                 380

Leu Gly Gly Gly Arg His Arg Leu Ser Phe Lys Thr Phe Val Ser Arg
385                 390                 395                 400

Arg Asp Phe Glu Asn Leu Asn Arg Asp Asp Tyr Tyr Phe Ser Gly Arg
                405                 410                 415
```

-continued

```
Val Val Arg Thr Thr Ser Ser Ile Gln His Pro Val Lys Thr Thr Asn
            420                 425                 430

Tyr Gly Phe Ser Leu Ser Asp Gln Ile Gln Trp Asn Asp Val Phe Ser
        435                 440                 445

Ser Arg Ala Gly Ile Arg Tyr Asp His Thr Lys Met Thr Pro Gln Glu
    450                 455                 460

Leu Asn Ala Glu Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Asn
                485                 490                 495

Gln Ala Trp Arg Val Gly Tyr Asp Ile Thr Ser Gly Tyr Arg Val Pro
            500                 505                 510

Asn Ala Ser Glu Val Tyr Phe Thr Tyr Asn His Gly Ser Gly Asn Trp
        515                 520                 525

Leu Pro Asn Pro Asn Leu Lys Ala Glu Arg Ser Thr Thr His Thr Leu
    530                 535                 540

Ser Leu Gln Gly Arg Ser Glu Lys Gly Met Leu Asp Ala Asn Leu Tyr
545                 550                 555                 560

Gln Ser Asn Tyr Arg Asn Phe Leu Ser Glu Glu Gln Lys Leu Thr Thr
                565                 570                 575

Ser Gly Thr Pro Gly Cys Thr Glu Glu Asn Ala Tyr Tyr Gly Ile Cys
            580                 585                 590

Ser Asp Pro Tyr Lys Glu Lys Leu Asp Trp Gln Met Lys Asn Ile Asp
        595                 600                 605

Lys Ala Arg Ile Arg Gly Ile Glu Leu Thr Gly Arg Leu Asn Val Asp
    610                 615                 620

Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
            660                 665                 670

Lys Trp Gly Val Phe Ser Arg Leu Thr Tyr Leu Gly Ala Lys Lys Val
        675                 680                 685

Lys Asp Ala Gln Tyr Thr Val Tyr Glu Asn Lys Gly Trp Gly Thr Pro
    690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Leu Phe Asn Arg Lys Tyr Thr Thr Trp Asp
            740                 745                 750

Ser Leu Arg Gly Leu Tyr Ser Tyr Ser Thr Thr Asn Ala Val Asp Arg
        755                 760                 765

Asp Gly Lys Gly Leu Asp Arg Tyr Arg Ala Pro Gly Arg Asn Tyr Ala
    770                 775                 780

Val Ser Leu Glu Trp Lys Phe
785                 790
```

<210> SEQ ID NO 13
<211> LENGTH: 465
<212> TYPE: PRT
<213> ORGANISM: Neisseria meningitidis (group B)

<400> SEQUENCE: 13

-continued

```
Met Ser Gln Gly Lys Ile Val Gln Ile Ile Gly Ala Val Val Asp Val
  1               5                  10                  15

Glu Phe Pro Arg Asp Met Ile Pro Arg Val Tyr Asp Ala Leu Lys Leu
             20                  25                  30

Asp Glu Asn Gly Leu Thr Leu Glu Val Gln Gln Leu Leu Gly Asp Gly
         35                  40                  45

Val Val Arg Ala Ile Ala Met Gly Ser Ser Asp Gly Leu Lys Arg Gly
     50                  55                  60

Met Thr Val Ser Asn Thr Gly Ala Pro Ile Thr Val Pro Val Gly Lys
 65                  70                  75                  80

Gly Thr Leu Gly Arg Ile Val Asp Val Leu Gly Thr Pro Val Asp Glu
                 85                  90                  95

Ala Gly Pro Ile Asp Thr Asp Lys Ser Arg Ala Ile His Gln Ala Ala
            100                 105                 110

Pro Lys Phe Asp Glu Leu Ser Ser Thr Thr Glu Leu Leu Glu Thr Gly
        115                 120                 125

Ile Lys Val Ile Asp Leu Leu Cys Pro Phe Ala Lys Gly Gly Lys Val
    130                 135                 140

Gly Leu Phe Gly Gly Ala Gly Val Gly Lys Thr Val Asn Met Met Glu
145                 150                 155                 160

Leu Ile Asn Asn Ile Ala Lys Ala His Ser Gly Leu Ser Val Phe Ala
                165                 170                 175

Gly Val Gly Glu Arg Thr Arg Glu Gly Asn Asp Phe Tyr His Glu Met
            180                 185                 190

Lys Asp Ser Asn Val Leu Asp Lys Val Ala Met Val Tyr Gly Gln Met
        195                 200                 205

Asn Glu Pro Pro Gly Asn Arg Leu Arg Val Ala Leu Thr Gly Leu Thr
    210                 215                 220

Met Ala Glu Tyr Phe Arg Asp Glu Lys Asp Glu Asn Gly Lys Gly Arg
225                 230                 235                 240

Asp Val Leu Phe Phe Val Asp Asn Ile Tyr Arg Tyr Thr Leu Ala Gly
                245                 250                 255

Thr Glu Val Ser Ala Leu Leu Gly Arg Met Pro Ser Ala Val Gly Tyr
            260                 265                 270

Gln Pro Thr Leu Ala Glu Glu Met Gly Arg Leu Gln Glu Arg Ile Thr
        275                 280                 285

Ser Thr Gln Thr Gly Ser Ile Thr Ser Ile Gln Ala Val Tyr Val Pro
    290                 295                 300

Ala Asp Asp Leu Thr Asp Pro Ser Pro Ala Thr Thr Phe Ala His Leu
305                 310                 315                 320

Asp Ala Thr Val Val Leu Ser Arg Asp Ile Ala Ser Leu Gly Ile Tyr
                325                 330                 335

Pro Ala Val Asp Pro Leu Asp Ser Thr Ser Arg Gln Leu Asp Pro Met
            340                 345                 350

Val Leu Gly Gln Glu His Tyr Asp Val Ala Arg Gly Val Gln Ser Thr
        355                 360                 365

Leu Gln Lys Tyr Lys Glu Leu Arg Asp Ile Ile Ala Ile Leu Gly Met
    370                 375                 380

Asp Glu Leu Ser Asp Glu Asp Lys Leu Thr Val Met Arg Ala Arg Lys
385                 390                 395                 400

Ile Gln Arg Phe Leu Ser Gln Pro Phe His Val Ala Glu Val Phe Thr
                405                 410                 415
```

-continued

```
Gly Ser Pro Gly Lys Tyr Val Ala Leu Arg Asp Thr Ile Ala Gly Phe
            420                 425                 430

Lys Ala Ile Leu Asn Gly Glu Tyr Asp His Leu Pro Glu Gln Ala Phe
        435                 440                 445

Tyr Met Val Gly Ser Ile Glu Glu Ala Val Glu Lys Ala Lys Thr Leu
    450                 455                 460

Asn
465


<210> SEQ ID NO 14
<211> LENGTH: 515
<212> TYPE: PRT
<213> ORGANISM: Neisseria meningitidis (group B)

<400> SEQUENCE: 14

Met Gln Leu Asn Pro Ala Glu Ile Ser Asp Leu Ile Lys Ala Lys Ile
  1               5                  10                  15

Glu Asn Leu Ser Val Asn Ala Glu Val Arg Thr Cys Gly Thr Val Ile
             20                  25                  30

Ser Val Thr Asp Gly Ile Val Arg Ile His Gly Leu Ser Asp Ala Met
         35                  40                  45

Gln Gly Glu Met Leu Glu Phe Pro Gly Asn Thr Phe Gly Leu Ala Met
     50                  55                  60

Asn Leu Glu Arg Asp Ser Val Gly Ala Val Val Leu Gly Glu Tyr Glu
 65                  70                  75                  80

His Ile Lys Glu Gly Asp Thr Val Thr Cys Thr Gly Arg Ile Leu Glu
                 85                  90                  95

Val Pro Val Gly Arg Glu Leu Val Gly Arg Val Val Asp Ala Leu Gly
            100                 105                 110

Arg Pro Ile Asp Gly Lys Gly Pro Ile Asn Thr Thr Leu Thr Ala Pro
        115                 120                 125

Ile Glu Lys Ile Ala Pro Gly Val Ile Ala Arg Lys Ser Val Asp Gln
    130                 135                 140

Pro Met Gln Thr Gly Leu Lys Ala Ile Asp Ser Met Val Pro Val Gly
145                 150                 155                 160

Arg Gly Gln Arg Glu Leu Ile Ile Gly Asp Arg Gln Thr Gly Lys Thr
                165                 170                 175

Ala Val Ala Leu Asp Ala Ile Val Asn Gln Lys Gly Thr Gly Val Ile
            180                 185                 190

Cys Ile Tyr Val Ala Ile Gly Gln Lys Ala Ser Ser Ile Ala Asn Val
        195                 200                 205

Val Arg Lys Leu Glu Glu His Gly Ala Met Glu His Thr Ile Val Val
    210                 215                 220

Ala Ala Thr Ala Ser Glu Ala Ala Ala Leu Gln Tyr Ile Ala Pro Tyr
225                 230                 235                 240

Ser Gly Cys Thr Met Gly Glu Phe Phe Arg Asp Arg Gly Glu Asp Ala
                245                 250                 255

Leu Ile Val Tyr Asp Asp Leu Ser Lys Gln Ala Val Ala Tyr Arg Gln
            260                 265                 270

Ile Ser Leu Leu Leu Arg Arg Pro Pro Gly Arg Glu Ala Tyr Pro Gly
        275                 280                 285

Asp Val Phe Tyr Leu His Ser Arg Leu Leu Glu Arg Ala Ala Arg Val
    290                 295                 300

Asn Glu His Glu Val Glu Lys Leu Thr Asn Gly Glu Val Lys Gly Lys
305                 310                 315                 320
```

```
Thr Gly Ser Leu Thr Ala Leu Pro Ile Ile Glu Thr Gln Ala Gly Asp
                325                 330                 335

Val Ser Ala Phe Val Pro Thr Asn Val Ile Ser Ile Thr Asp Gly Gln
            340                 345                 350

Ile Phe Leu Glu Thr Asp Leu Phe Asn Ala Gly Ile Arg Pro Ala Ile
        355                 360                 365

Asn Ala Gly Ile Ser Val Ser Arg Val Gly Gly Ala Ala Gln Thr Lys
    370                 375                 380

Val Ile Lys Lys Leu Gly Gly Gly Ile Arg Leu Ala Leu Ala Gln Tyr
385                 390                 395                 400

Arg Glu Leu Ala Ala Phe Ser Gln Phe Ala Ser Asp Leu Asp Glu Ala
                405                 410                 415

Thr Arg Lys Gln Leu Glu His Gly Glu Val Val Thr Glu Leu Met Lys
            420                 425                 430

Gln Lys Gln Phe Ser Thr Leu Asn Thr Ala Glu Met Ala Leu Thr Leu
        435                 440                 445

Trp Ala Ile Asn Asn Gly Ser Tyr Ser Asp Val Pro Val Ala Lys Ala
    450                 455                 460

Leu Ala Phe Glu Ser Glu Phe Leu Ser Phe Val Arg Thr Gln His Pro
465                 470                 475                 480

Glu Val Leu Glu Ala Val Asn Ala Ser Gly Ala Met Ser Asp Glu Ser
                485                 490                 495

Glu Lys Thr Leu Glu Ala Ala Met Lys Ser Phe Lys Ser Ser Tyr Ala
            500                 505                 510

Tyr Gln Ala
        515


<210> SEQ ID NO 15
<211> LENGTH: 558
<212> TYPE: PRT
<213> ORGANISM: Neisseria meningitidis (group B)

<400> SEQUENCE: 15

Met Ser Gln Gln Tyr Val Tyr Ser Met Leu Arg Val Ser Lys Val Val
  1               5                  10                  15

Pro Pro Gln Lys Thr Ile Ile Lys Asp Ile Ser Leu Ser Phe Phe Pro
            20                  25                  30

Gly Ala Lys Ile Gly Leu Leu Gly Leu Asn Gly Ala Gly Lys Ser Thr
        35                  40                  45

Val Leu Arg Ile Met Ala Gly Val Asp Lys Glu Phe Glu Gly Glu Ala
    50                  55                  60

Val Pro Met Gly Gly Ile Lys Ile Gly Tyr Leu Pro Gln Glu Pro Glu
 65                  70                  75                  80

Leu Asp Pro Glu Lys Thr Val Arg Glu Glu Val Glu Ser Gly Leu Gly
                85                  90                  95

Glu Val Ala Ala Ala Gln Lys Arg Leu Glu Glu Val Tyr Ala Glu Tyr
            100                 105                 110

Ala Asn Pro Asp Ala Asp Phe Asp Ala Leu Ala Glu Glu Gln Gly Arg
        115                 120                 125

Leu Glu Ala Ile Ile Ala Ala Gly Ser Ser Thr Gly Gly Gly Ala Glu
    130                 135                 140

His Glu Leu Glu Ile Ala Ala Asp Ala Leu Arg Leu Pro Glu Trp Asp
145                 150                 155                 160

Ala Lys Ile Asp Asn Leu Ser Gly Gly Glu Lys Arg Arg Val Ala Leu
```

-continued

```
                165                 170                 175

Cys Lys Leu Leu Leu Ser Lys Pro Asp Met Leu Leu Leu Asp Glu Pro
            180                 185                 190

Thr Asn His Leu Asp Ala Glu Ser Val Glu Trp Leu Glu Gln Phe Leu
        195                 200                 205

Val Arg Phe Pro Gly Thr Val Val Ala Val Thr His Asp Arg Tyr Phe
    210                 215                 220

Leu Asp Asn Ala Ala Glu Trp Ile Leu Glu Leu Asp Arg Gly His Gly
225                 230                 235                 240

Ile Pro Trp Lys Gly Asn Tyr Ser Ser Trp Leu Glu Gln Lys Glu Lys
                245                 250                 255

Arg Leu Glu Asn Glu Ala Lys Ser Glu Ala Ala Arg Val Lys Ala Met
            260                 265                 270

Lys Gln Glu Leu Glu Trp Val Arg Gln Asn Ala Lys Gly Arg Gln Ala
        275                 280                 285

Lys Ser Lys Ala Arg Leu Ala Arg Phe Glu Glu Met Ser Asn Tyr Glu
    290                 295                 300

Tyr Gln Lys Arg Asn Glu Thr Gln Glu Ile Phe Ile Pro Val Ala Glu
305                 310                 315                 320

Arg Leu Gly Asn Glu Val Ile Glu Phe Val Asn Val Ser Lys Ser Phe
                325                 330                 335

Gly Asp Lys Val Leu Ile Asp Asp Leu Ser Phe Lys Val Pro Ala Gly
            340                 345                 350

Ala Ile Val Gly Ile Ile Gly Pro Asn Gly Ala Gly Lys Ser Thr Leu
        355                 360                 365

Phe Lys Met Ile Ser Gly Lys Glu Gln Pro Asp Ser Gly Glu Val Lys
    370                 375                 380

Ile Gly Gln Thr Val Lys Met Ser Leu Ile Asp Gln Ser Arg Glu Gly
385                 390                 395                 400

Leu Gln Asn Asp Lys Thr Val Phe Asp Asn Ile Ala Glu Gly Arg Asp
                405                 410                 415

Ile Leu Gln Val Gly Gln Phe Glu Ile Pro Ala Arg Gln Tyr Leu Gly
            420                 425                 430

Arg Phe Asn Phe Lys Gly Ser Asp Gln Ser Lys Ile Ala Gly Gln Leu
        435                 440                 445

Ser Gly Gly Glu Arg Gly Arg Leu His Leu Ala Lys Thr Leu Leu Ser
    450                 455                 460

Gly Gly Asn Val Leu Leu Leu Asp Glu Pro Ser Asn Asp Leu Asp Val
465                 470                 475                 480

Glu Thr Leu Arg Ala Leu Glu Asp Ala Leu Leu Glu Phe Ala Gly Ser
                485                 490                 495

Val Met Val Ile Ser His Asp Arg Trp Phe Leu Asp Arg Ile Ala Thr
            500                 505                 510

His Ile Leu Ala Cys Glu Gly Asp Ser Lys Trp Val Phe Phe Asp Gly
        515                 520                 525

Asn Tyr Gln Glu Tyr Glu Ala Asp Lys Lys Arg Arg Leu Gly Glu Glu
    530                 535                 540

Gly Ala Lys Pro Lys Arg Ile Lys Tyr Lys Pro Val Thr Arg
545                 550                 555
```

<210> SEQ ID NO 16
<211> LENGTH: 241
<212> TYPE: PRT
<213> ORGANISM: Neisseria meningitidis (group B)

<400> SEQUENCE: 16

```
Ala Ser Glu Asp Gly Ser Arg Ser Pro Tyr Tyr Val Gln Ala Asp Leu
  1               5                  10                  15

Ala Tyr Ala Ala Glu Arg Ile Thr His Asp Tyr Pro Lys Ala Thr Gly
             20                  25                  30

Ala Asn Asn Thr Ser Thr Val Ser Asp Tyr Phe Arg Asn Ile Arg Ala
         35                  40                  45

His Ser Ile His Pro Arg Val Ser Val Gly Tyr Asp Phe Gly Gly Trp
     50                  55                  60

Arg Ile Ala Ala Asp Tyr Ala Ser Tyr Arg Lys Trp Asn Asn Asn Lys
 65                  70                  75                  80

Tyr Ser Val Asn Thr Lys Glu Leu Gln Lys Asn Asn Ser Ser Gly Ile
                 85                  90                  95

Trp Gln Glu Leu Lys Thr Glu Asn Gln Glu Asn Gly Thr Phe His Ala
            100                 105                 110

Ala Ser Ser Leu Gly Leu Ser Ala Ile Tyr Asp Phe Lys Leu Asn Asp
        115                 120                 125

Lys Phe Asp Lys Phe Lys Pro Tyr Ile Gly Ala Arg Val Ala Tyr Gly
    130                 135                 140

His Val Lys His Gln Val His Ser Val Arg Lys Glu Thr Thr Thr Thr
145                 150                 155                 160

Phe Ser Pro Pro Ala Gln Gly Ala Thr Val Pro Gly Lys Ile Val Gln
                165                 170                 175

Gly Pro Thr Asn Lys Pro Ala Tyr His Glu Ser Asn Ser Ile Ser Ser
            180                 185                 190

Leu Gly Leu Gly Val Ile Ala Gly Val Gly Phe Asp Ile Thr Pro Lys
        195                 200                 205

Leu Thr Leu Asp Thr Gly Tyr Arg Tyr His Asn Trp Gly Arg Leu Glu
    210                 215                 220

Asn Thr Arg Phe Lys Thr His Glu Val Ser Leu Gly Met Arg Tyr His
225                 230                 235                 240

Phe
```

<210> SEQ ID NO 17
<211> LENGTH: 371
<212> TYPE: PRT
<213> ORGANISM: Neisseria meningitidis (group B)

<400> SEQUENCE: 17

```
Met Arg Leu Phe Lys Ser Leu Lys Asn Pro Lys Lys Thr Asp Ala Lys
  1               5                  10                  15

Leu Pro Lys Lys Ser Ser Gly Leu Asn Asn Arg Ala Ala Ile Gly Ile
             20                  25                  30

Asp Ile Asp Gln His Ser Ile Lys Met Val Gln Leu Ser Gly Arg Ser
         35                  40                  45

Leu Asn Gln Ile Gln Leu Glu Lys Tyr Val Ile Ala Lys Leu Pro Lys
     50                  55                  60

Asn Ile Ile Gln Gly Asn Lys Val Gln Asn Tyr Asp Gln Leu Val Thr
 65                  70                  75                  80

Tyr Leu Gln Gln Ala Tyr Ala Lys Leu Gly Thr Ser Cys Lys Asn Ile
                 85                  90                  95

Ile Ala Ser Val Pro Gln Asn Leu Ala Thr Ile Glu Gln Leu Thr Tyr
            100                 105                 110
```

```
Thr Asp Lys Asp Ala Glu Leu Asp Leu Gln Gly Phe Val Glu Ser Ser
        115                 120                 125

Ile Ser Glu Val Ser Ser Ile Ser Leu Glu Glu Ala Asn Tyr Asp Tyr
    130                 135                 140

Gln Val Leu Ser Gln Ser Ala Ala Gly Glu Ala Val Leu Ala Val Ala
145                 150                 155                 160

Ser Arg Lys Asp Glu Ile Glu Pro Leu Ile Asp Ala Phe Asn Ala Ala
                165                 170                 175

Gly Met Lys Leu Ser Ala Leu Asp Val Asp Ile Phe Gly Gln Tyr Asn
            180                 185                 190

Ala Tyr Ala Leu Trp Ile Asn His Phe Ala Pro Glu Leu Ala Ala Glu
        195                 200                 205

Lys Val Ala Ile Phe Gly Val Tyr Ala Ala Gln Thr Tyr Ala Leu Val
    210                 215                 220

Ile Gln Asp Gly Lys Ile Leu Tyr Lys Gln Glu Thr Ser Val Ser Glu
225                 230                 235                 240

Glu Gln Leu Asn Gln Leu Ile Gln Arg Thr Tyr Gln Val Thr Glu Glu
                245                 250                 255

Lys Ala Glu Glu Ile Ile Asn Ser Pro Gln Lys Pro Ser Asp Tyr Gln
            260                 265                 270

Glu Ser Val Ala Asn Tyr Phe Asn Gln Gln Ile Thr Gln Glu Ile Gln
        275                 280                 285

Arg Val Leu Gln Phe Tyr Tyr Thr Thr Gln Thr Ala Asp Asp Met Thr
    290                 295                 300

Asp Ile Lys His Ile Leu Leu Thr Gly Glu Ala Ala Arg Gln Glu Gly
305                 310                 315                 320

Ile Ala Gln Thr Val Ala Ser Gln Thr Asn Ala Asp Val Gln Cys Val
                325                 330                 335

His Pro Ala Arg Tyr Phe Ala Asp Asn Leu Lys Thr Asp Lys Gln Gln
            340                 345                 350

Phe Glu Leu Asp Ala Pro Thr Leu Thr Arg Ala Phe Gly Leu Ala Val
        355                 360                 365

Arg Gly Leu
    370


<210> SEQ ID NO 18
<211> LENGTH: 761
<212> TYPE: PRT
<213> ORGANISM: Neisseria meningitidis (group B)

<400> SEQUENCE: 18

Met Asn Thr Lys Leu Thr Lys Ile Ile Ser Gly Leu Phe Val Ala Thr
  1               5                  10                  15

Ala Ala Phe Gln Thr Ala Ser Ala Gly Asn Ile Thr Asp Ile Lys Val
             20                  25                  30

Ser Ser Leu Pro Asn Lys Gln Lys Ile Val Lys Val Ser Phe Asp Lys
         35                  40                  45

Glu Ile Val Asn Pro Thr Gly Phe Val Thr Ser Ser Pro Ala Arg Ile
     50                  55                  60

Ala Leu Asp Phe Glu Gln Thr Gly Ile Ser Met Asp Gln Gln Val Leu
 65                  70                  75                  80

Glu Tyr Ala Asp Pro Leu Leu Ser Lys Ile Ser Ala Ala Gln Asn Ser
                 85                  90                  95

Ser Arg Ala Arg Leu Val Leu Asn Leu Asn Lys Pro Gly Gln Tyr Asn
            100                 105                 110
```

-continued

```
Thr Glu Val Arg Gly Asn Lys Val Trp Ile Phe Ile Asn Glu Ser Asp
        115                 120                 125

Asp Thr Val Ser Ala Pro Ala Arg Pro Ala Val Lys Ala Ala Pro Ala
    130                 135                 140

Ala Pro Ala Lys Gln Gln Ala Ala Ala Pro Ser Thr Lys Ser Ala Val
145                 150                 155                 160

Ser Val Ser Lys Pro Phe Thr Pro Ala Lys Gln Gln Ala Ala Ala Pro
                165                 170                 175

Phe Thr Glu Ser Val Val Ser Val Ser Ala Pro Phe Ser Pro Ala Lys
            180                 185                 190

Gln Gln Ala Ala Ala Ser Ala Lys Gln Gln Thr Ala Ala Pro Ala Lys
        195                 200                 205

Gln Gln Ala Ala Thr Pro Ala Lys Gln Thr Asn Ile Asp Phe Arg Lys
    210                 215                 220

Asp Gly Lys Asn Ala Gly Ile Ile Glu Leu Ala Ala Leu Gly Phe Ala
225                 230                 235                 240

Gly Gln Pro Asp Ile Ser Gln Gln His Asp His Ile Ile Val Thr Leu
                245                 250                 255

Lys Asn His Thr Leu Pro Thr Thr Leu Gln Arg Ser Leu Asp Val Ala
            260                 265                 270

Asp Phe Lys Thr Pro Val Gln Lys Val Thr Leu Lys Arg Leu Asn Asn
        275                 280                 285

Asp Thr Gln Leu Ile Ile Thr Thr Ala Gly Asn Trp Glu Leu Val Asn
    290                 295                 300

Lys Ser Ala Ala Pro Gly Tyr Phe Thr Phe Gln Val Leu Pro Lys Lys
305                 310                 315                 320

Gln Asn Leu Glu Ser Gly Gly Val Asn Asn Ala Pro Lys Thr Phe Thr
                325                 330                 335

Gly Arg Lys Ile Ser Leu Asp Phe Gln Asp Val Glu Ile Arg Thr Ile
            340                 345                 350

Leu Gln Ile Leu Ala Lys Glu Ser Gly Met Asn Ile Val Ala Ser Asp
        355                 360                 365

Ser Val Asn Gly Lys Met Thr Leu Ser Leu Lys Asp Val Pro Trp Asp
    370                 375                 380

Gln Ala Leu Asp Leu Val Met Gln Ala Arg Asn Leu Asp Met Arg Gln
385                 390                 395                 400

Gln Gly Asn Ile Val Asn Ile Ala Pro Arg Asp Glu Leu Leu Ala Lys
                405                 410                 415

Asp Lys Ala Phe Leu Gln Ala Glu Lys Asp Ile Ala Asp Leu Gly Ala
            420                 425                 430

Leu Tyr Ser Gln Asn Phe Gln Leu Lys Tyr Lys Asn Val Glu Glu Phe
        435                 440                 445

Arg Ser Ile Leu Arg Leu Asp Asn Ala Asp Thr Thr Gly Asn Arg Asn
    450                 455                 460

Thr Leu Val Ser Gly Arg Gly Ser Val Leu Ile Asp Pro Ala Thr Asn
465                 470                 475                 480

Thr Leu Ile Val Thr Asp Thr Arg Ser Val Ile Glu Lys Phe Arg Lys
                485                 490                 495

Leu Ile Asp Glu Leu Asp Val Pro Ala Gln Gln Val Met Ile Glu Ala
            500                 505                 510

Arg Ile Val Glu Ala Ala Asp Gly Phe Ser Arg Asp Leu Gly Val Lys
        515                 520                 525
```

-continued

```
Phe Gly Ala Thr Gly Lys Lys Lys Leu Lys Asn Asp Thr Ser Ala Phe
    530                 535                 540

Gly Trp Gly Val Asn Ser Gly Phe Gly Gly Asp Asp Lys Trp Gly Ala
545                 550                 555                 560

Glu Thr Lys Ile Asn Leu Pro Ile Thr Ala Ala Ala Asn Ser Ile Ser
                565                 570                 575

Leu Val Arg Ala Ile Ser Ser Gly Ala Leu Asn Leu Glu Leu Ser Ala
            580                 585                 590

Ser Glu Ser Leu Ser Lys Thr Lys Thr Leu Ala Asn Pro Arg Val Leu
        595                 600                 605

Thr Gln Asn Arg Lys Glu Ala Lys Ile Glu Ser Gly Tyr Glu Ile Pro
    610                 615                 620

Phe Thr Val Thr Ser Ile Ala Asn Gly Gly Ser Ser Thr Asn Thr Glu
625                 630                 635                 640

Leu Lys Lys Ala Val Leu Gly Leu Thr Val Thr Pro Asn Ile Thr Pro
                645                 650                 655

Asp Gly Gln Ile Ile Met Thr Val Lys Ile Asn Lys Asp Ser Pro Ala
            660                 665                 670

Gln Cys Ala Ser Gly Asn Gln Thr Ile Leu Cys Ile Ser Thr Lys Asn
        675                 680                 685

Leu Asn Thr Gln Ala Met Val Glu Asn Gly Gly Thr Leu Ile Val Gly
    690                 695                 700

Gly Ile Tyr Glu Glu Asp Asn Gly Asn Thr Leu Thr Lys Val Pro Leu
705                 710                 715                 720

Leu Gly Asp Ile Pro Val Ile Gly Asn Leu Phe Lys Thr Arg Gly Lys
                725                 730                 735

Lys Thr Asp Arg Arg Glu Leu Leu Ile Phe Ile Thr Pro Arg Ile Met
            740                 745                 750

Gly Thr Ala Gly Asn Ser Leu Arg Tyr
        755                 760


<210> SEQ ID NO 19
<211> LENGTH: 758
<212> TYPE: PRT
<213> ORGANISM: Neisseria meningitidis (group B)

<400> SEQUENCE: 19

Met Ser Glu Pro Ile Gln Pro Thr Ser Leu Ser Leu Gly Ser Thr Cys
  1               5                  10                  15

Leu Phe Cys Ser Asn Glu Ser Gly Ser Pro Glu Arg Thr Glu Ala Ala
             20                  25                  30

Val Gln Gly Ser Gly Glu Ala Ser Ile Pro Glu Asp Tyr Thr Arg Ile
         35                  40                  45

Val Ala Asp Arg Met Glu Gly Gln Ser Gln Val Gln Val Arg Ala Glu
     50                  55                  60

Gly Asn Val Val Val Glu Arg Asn Arg Thr Thr Leu Asn Thr Asp Trp
 65                  70                  75                  80

Ala Asp Tyr Asp Gln Ser Gly Asp Thr Val Thr Ala Gly Asp Arg Phe
                 85                  90                  95

Ala Leu Gln Gln Asp Gly Thr Leu Ile Arg Gly Glu Thr Leu Thr Tyr
            100                 105                 110

Asn Leu Glu Gln Gln Thr Gly Glu Ala His Asn Val Arg Met Glu Ile
        115                 120                 125

Glu Gln Gly Gly Arg Arg Leu Gln Ser Val Ser Arg Thr Ala Glu Met
    130                 135                 140
```

-continued

```
Leu Gly Glu Gly His Tyr Lys Leu Thr Glu Thr Gln Phe Asn Thr Cys
145                 150                 155                 160

Ser Ala Gly Asp Ala Gly Trp Tyr Val Lys Ala Ala Ser Val Glu Ala
                165                 170                 175

Asp Arg Glu Lys Gly Ile Gly Val Ala Lys His Ala Ala Phe Val Phe
            180                 185                 190

Gly Gly Val Pro Ile Phe Tyr Thr Pro Trp Ala Asp Phe Pro Leu Asp
        195                 200                 205

Gly Asn Arg Lys Ser Gly Leu Leu Val Pro Ser Leu Ser Ala Gly Ser
    210                 215                 220

Asp Gly Val Ser Leu Ser Val Pro Tyr Tyr Phe Asn Leu Ala Pro Asn
225                 230                 235                 240

Leu Asp Ala Thr Phe Ala Pro Ser Val Ile Gly Glu Arg Gly Ala Val
                245                 250                 255

Phe Asp Gly Gln Val Arg Tyr Leu Arg Pro Asp Tyr Ala Gly Gln Ser
            260                 265                 270

Asp Leu Thr Trp Leu Pro His Asp Lys Lys Ser Gly Arg Asn Asn Arg
        275                 280                 285

Tyr Gln Ala Lys Trp Gln His Arg His Asp Ile Ser Asp Thr Leu Gln
    290                 295                 300

Ala Gly Val Asp Phe Asn Gln Val Ser Asp Ser Gly Tyr Tyr Arg Asp
305                 310                 315                 320

Phe Tyr Gly Asn Lys Glu Ile Ala Gly Asn Val Asn Leu Asn Arg Arg
                325                 330                 335

Val Trp Leu Asp Tyr Gly Gly Arg Ala Ala Gly Gly Ser Leu Asn Ala
            340                 345                 350

Gly Leu Ser Val Leu Lys Tyr Gln Thr Leu Ala Asn Gln Ser Gly Tyr
        355                 360                 365

Lys Asp Lys Pro Tyr Ala Leu Met Pro Arg Leu Ser Val Glu Trp Arg
    370                 375                 380

Lys Asn Thr Gly Arg Ala Gln Ile Gly Val Ser Ala Gln Phe Thr Arg
385                 390                 395                 400

Phe Ser His Asp Ser Arg Gln Asp Gly Ser Arg Leu Val Val Tyr Pro
                405                 410                 415

Asp Ile Lys Trp Asp Phe Ser Asn Ser Trp Gly Tyr Val Arg Pro Lys
            420                 425                 430

Leu Gly Leu His Ala Thr Tyr Tyr Ser Leu Asn Arg Phe Gly Ser Gln
        435                 440                 445

Glu Ala Arg Arg Val Ser Arg Thr Leu Pro Ile Val Asn Ile Asp Ser
    450                 455                 460

Gly Ala Thr Phe Glu Arg Asn Thr Arg Met Phe Gly Gly Glu Val Leu
465                 470                 475                 480

Gln Thr Leu Glu Pro Arg Leu Phe Tyr Asn Tyr Ile Pro Ala Lys Ser
                485                 490                 495

Gln Asn Asp Leu Pro Asn Phe Asp Ser Ser Glu Ser Ser Phe Gly Tyr
            500                 505                 510

Gly Gln Leu Phe Arg Glu Asn Leu Tyr Tyr Gly Asn Asp Arg Ile Asn
        515                 520                 525

Thr Ala Asn Ser Leu Ser Ala Ala Val Gln Ser Arg Ile Leu Asp Gly
    530                 535                 540

Ala Thr Gly Glu Glu Arg Phe Arg Ala Gly Ile Gly Gln Lys Phe Tyr
545                 550                 555                 560
```

-continued

```
Phe Lys Asp Asp Ala Val Met Leu Asp Gly Ser Val Gly Lys Lys Pro
                565                 570                 575

Arg Asn Arg Ser Asp Trp Val Ala Phe Ala Ser Gly Ser Ile Gly Ser
            580                 585                 590

Arg Phe Ile Leu Asp Ser Ser Ile His Tyr Asn Gln Asn Asp Lys Arg
        595                 600                 605

Ala Glu Asn Tyr Ala Val Gly Ala Ser Tyr Arg Pro Ala Gln Gly Lys
    610                 615                 620

Val Leu Asn Ala Arg Tyr Lys Tyr Gly Arg Asn Glu Lys Ile Tyr Leu
625                 630                 635                 640

Lys Ser Asp Gly Ser Tyr Phe Tyr Asp Lys Leu Ser Gln Leu Asp Leu
                645                 650                 655

Ser Ala Gln Trp Pro Leu Thr Arg Asn Leu Ser Ala Val Val Arg Tyr
            660                 665                 670

Asn Tyr Gly Phe Glu Ala Lys Lys Pro Ile Glu Val Leu Ala Gly Ala
        675                 680                 685

Glu Tyr Lys Ser Ser Cys Gly Cys Trp Gly Ala Gly Val Tyr Ala Gln
    690                 695                 700

Arg Tyr Val Thr Gly Glu Asn Thr Tyr Lys Asn Ala Val Phe Phe Ser
705                 710                 715                 720

Leu Gln Leu Lys Asp Leu Ser Ser Val Gly Arg Asn Pro Ala Asp Arg
                725                 730                 735

Met Asp Val Ala Val Pro Gly Tyr Ile Thr Ala His Ser Leu Ser Ala
            740                 745                 750

Gly Arg Asn Lys Arg Pro
        755


<210> SEQ ID NO 20
<211> LENGTH: 174
<212> TYPE: PRT
<213> ORGANISM: Neisseria meningitidis (group B)

<400> SEQUENCE: 20

Met Lys Lys Ala Leu Ala Thr Leu Ile Ala Leu Ala Leu Pro Ala Ala
  1               5                  10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
     50                  55                  60

Tyr Thr Arg Tyr Lys Asn Tyr Lys Ala Pro Ser Thr Asp Phe Lys Leu
 65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
                165                 170
```

```
<210> SEQ ID NO 21
<211> LENGTH: 535
<212> TYPE: PRT
<213> ORGANISM: Neisseria meningitidis (group B)

<400> SEQUENCE: 21

Met Ser Ile Val Glu Ile Lys Val Pro Asp Ile Gly Gly His Glu Asn
  1               5                  10                  15

Val Asp Ile Ile Ala Val Glu Val Lys Ala Gly Asp Thr Ile Ala Val
             20                  25                  30

Asp Asp Thr Leu Ile Thr Leu Glu Thr Asp Lys Ala Thr Met Asp Val
         35                  40                  45

Pro Ala Asp Ala Ala Gly Val Val Lys Glu Val Lys Val Lys Val Gly
     50                  55                  60

Asp Lys Ile Ser Glu Gly Gly Val Ile Leu Thr Val Glu Thr Gly Ala
 65                  70                  75                  80

Ala Ala Ala Glu Ala Ala Pro Ala Ala Ala Glu Ala Gln Pro Ala Pro
                 85                  90                  95

Ala Ala Ala Pro Ala Ala Ala Gly Gly Ala Thr Val Gln Val Ala Val
            100                 105                 110

Pro Asp Ile Gly Gly His Thr Asp Val Asp Val Ile Ala Val Glu Ile
        115                 120                 125

Lys Val Gly Asp Thr Val Ala Glu Asp Asp Thr Leu Ile Thr Leu Glu
    130                 135                 140

Thr Asp Lys Ala Thr Met Asp Val Pro Cys Thr Ala Ala Gly Val Val
145                 150                 155                 160

Lys Ala Val Phe Leu Lys Val Gly Asp Lys Val Ser Glu Gly Ser Ala
                165                 170                 175

Ile Ile Glu Val Glu Thr Val Gly Ser Ala Ala Ala Ala Pro Ala Gln
            180                 185                 190

Ala Ala Gln Ala Ala Ala Pro Ala Ala Ala Pro Pro Pro Thr Ala Ala
        195                 200                 205

Ala Ala Pro Ala Ala Ala Pro Ala Pro Ser Ala Pro Ala Ala Ala Lys
    210                 215                 220

Ile Asp Glu Ala Ala Phe Ala Lys Ala His Ala Gly Pro Ser Ala Arg
225                 230                 235                 240

Lys Leu Ala Arg Glu Leu Gly Val Asp Leu Gly Gln Val Lys Gly Thr
                245                 250                 255

Gly Leu Lys Gly Arg Ile Met Gly Asp Asp Ile Lys Ala Phe Val Lys
            260                 265                 270

Ser Val Met Gln Gly Gly Ala Ala Lys Pro Ala Ala Ala Ser Ala Ser
        275                 280                 285

Leu Gly Gly Gly Leu Asp Leu Leu Pro Trp Pro Lys Val Asp Phe Ser
    290                 295                 300

Lys Phe Gly Asn Val Glu Val Lys Glu Leu Ser Arg Ile Lys Lys Ile
305                 310                 315                 320

Ser Gly Gln Asn Leu Ser Arg Asn Trp Val Val Ile Pro His Val Thr
                325                 330                 335

Val His Glu Glu Ala Asp Met Thr Glu Leu Glu Glu Phe Arg Lys Gln
            340                 345                 350

Leu Asn Lys Glu Trp Glu Arg Glu Gly Val Lys Leu Ser Pro Leu Ala
        355                 360                 365

Phe Ile Ile Lys Ala Ser Val Ser Ala Leu Lys Ala Phe Pro Glu Phe
```

-continued

```
    370                 375                 380

Asn Ala Ser Leu Asp Gly Asp Asn Leu Val Leu Lys Asn Tyr Phe Asn
385                 390                 395                 400

Ile Gly Phe Ala Ala Asp Thr Pro Asn Gly Leu Val Val Pro Val Ile
                405                 410                 415

Lys Asp Val Asp Gln Lys Gly Leu Lys Gln Ile Ser Gln Glu Leu Thr
            420                 425                 430

Glu Leu Ser Lys Lys Ala Arg Glu Gly Lys Leu Lys Pro Gln Glu Met
        435                 440                 445

Gln Gly Ala Cys Phe Thr Ile Ser Ser Leu Gly Gly Ile Gly Gly Thr
    450                 455                 460

Gly Phe Thr Pro Ile Val Asn Ala Pro Glu Val Ala Ile Leu Gly Val
465                 470                 475                 480

Cys Lys Ser Gln Ile Lys Pro Val Trp Asn Gly Lys Glu Phe Ala Pro
                485                 490                 495

Arg Leu Met Cys Pro Leu Ser Leu Ser Phe Asp His Arg Val Ile Asp
            500                 505                 510

Gly Ala Ala Gly Met Arg Phe Thr Val Phe Leu Ala Lys Leu Leu Lys
        515                 520                 525

Asp Phe Arg Arg Ile Thr Leu
    530                 535


<210> SEQ ID NO 22
<211> LENGTH: 394
<212> TYPE: PRT
<213> ORGANISM: Neisseria meningitidis (group B)

<400> SEQUENCE: 22

Met Ala Lys Glu Lys Phe Glu Arg Ser Lys Pro His Val Asn Val Gly
  1               5                  10                  15

Thr Ile Gly His Val Asp His Gly Lys Thr Thr Leu Thr Ala Ala Leu
            20                  25                  30

Thr Thr Ile Leu Ala Lys Lys Phe Gly Gly Ala Ala Lys Ala Tyr Asp
        35                  40                  45

Gln Ile Asp Asn Ala Pro Glu Glu Lys Ala Arg Gly Ile Thr Ile Asn
     50                  55                  60

Thr Ser His Val Glu Tyr Glu Thr Glu Thr Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Cys Ser Ala Ala Asp Gly Pro
            100                 105                 110

Met Pro Gln Thr Arg Glu His Ile Leu Leu Ala Arg Gln Val Gly Val
        115                 120                 125

Pro Tyr Ile Ile Val Phe Met Asn Lys Cys Asp Met Val Asp Asp Ala
    130                 135                 140

Glu Leu Leu Glu Leu Val Glu Met Glu Ile Arg Asp Leu Leu Ser Ser
145                 150                 155                 160

Tyr Asp Phe Pro Gly Asp Asp Cys Pro Ile Val Gln Gly Ser Ala Leu
                165                 170                 175

Lys Ala Leu Glu Gly Asp Ala Ala Tyr Glu Glu Lys Ile Phe Glu Leu
            180                 185                 190

Ala Ala Ala Leu Asp Ser Tyr Ile Pro Thr Pro Glu Arg Ala Val Asp
        195                 200                 205
```

-continued

```
Lys Pro Phe Leu Leu Pro Ile Glu Asp Val Phe Ser Ile Ser Gly Arg
    210                 215                 220

Gly Thr Val Val Thr Gly Arg Val Glu Arg Gly Ile Ile His Val Gly
225                 230                 235                 240

Asp Glu Ile Glu Ile Val Gly Leu Lys Glu Thr Gln Lys Thr Thr Cys
                245                 250                 255

Thr Gly Val Glu Met Phe Arg Lys Leu Leu Asp Glu Gly Gln Ala Gly
            260                 265                 270

Asp Asn Val Gly Val Leu Leu Arg Gly Thr Lys Arg Glu Asp Val Glu
        275                 280                 285

Arg Gly Gln Val Leu Ala Lys Pro Gly Thr Ile Thr Pro His Thr Lys
    290                 295                 300

Phe Lys Ala Glu Val Tyr Val Leu Ser Lys Glu Glu Gly Gly Arg His
305                 310                 315                 320

Thr Pro Phe Phe Ala Asn Tyr Arg Pro Gln Phe Tyr Phe Arg Thr Thr
                325                 330                 335

Asp Val Thr Gly Ala Val Thr Leu Glu Glu Gly Val Glu Met Val Met
            340                 345                 350

Pro Gly Glu Asn Val Thr Ile Thr Val Glu Leu Ile Ala Pro Ile Ala
        355                 360                 365

Met Glu Glu Gly Leu Arg Phe Ala Ile Arg Glu Gly Gly Arg Thr Val
    370                 375                 380

Gly Ala Gly Val Val Ser Ser Val Ile Ala
385                 390


<210> SEQ ID NO 23
<211> LENGTH: 701
<212> TYPE: PRT
<213> ORGANISM: Neisseria meningitidis (group B)

<400> SEQUENCE: 23

Met Ala Arg Lys Thr Pro Ile Ser Leu Tyr Arg Asn Ile Gly Ile Ser
  1               5                  10                  15

Ala His Ile Asp Ala Gly Lys Thr Thr Thr Thr Glu Arg Ile Leu Phe
             20                  25                  30

Tyr Thr Gly Leu Thr His Lys Leu Gly Glu Val His Asp Gly Ala Ala
         35                  40                  45

Thr Thr Asp Tyr Met Glu Gln Glu Gln Glu Arg Gly Ile Thr Ile Thr
     50                  55                  60

Ser Ala Ala Val Thr Ser Tyr Trp Ser Gly Met Ala Lys Gln Phe Pro
 65                  70                  75                  80

Glu His Arg Phe Asn Ile Ile Asp Thr Pro Gly His Val Asp Phe Thr
                 85                  90                  95

Val Glu Val Glu Arg Ser Met Arg Val Leu Asp Gly Ala Val Met Val
            100                 105                 110

Tyr Cys Ala Val Gly Gly Val Gln Pro Gln Ser Glu Thr Val Trp Arg
        115                 120                 125

Gln Ala Asn Lys Tyr Gln Val Pro Arg Leu Ala Phe Val Asn Lys Met
    130                 135                 140

Asp Arg Gln Gly Ala Asn Phe Phe Arg Val Val Glu Gln Met Lys Thr
145                 150                 155                 160

Arg Leu Arg Ala Asn Pro Val Pro Ile Val Ile Pro Val Gly Ala Glu
                165                 170                 175

Asp Asn Phe Ser Gly Val Val Asp Leu Leu Lys Met Lys Ser Ile Ile
            180                 185                 190
```

-continued

```
Trp Asn Glu Val Asp Lys Gly Thr Thr Phe Thr Tyr Gly Asp Ile Pro
        195                 200                 205

Ala Glu Leu Val Glu Thr Ala Glu Glu Trp Arg Gln Asn Met Ile Glu
    210                 215                 220

Ala Ala Ala Glu Ala Ser Glu Glu Leu Met Asp Lys Tyr Leu Gly Gly
225                 230                 235                 240

Asp Glu Leu Thr Glu Glu Glu Ile Val Gly Ala Leu Arg Gln Arg Thr
                245                 250                 255

Leu Ala Gly Glu Ile Gln Pro Met Leu Cys Gly Ser Ala Phe Lys Asn
            260                 265                 270

Lys Gly Val Gln Arg Met Leu Asp Ala Val Val Glu Leu Leu Pro Ala
        275                 280                 285

Pro Thr Asp Ile Pro Pro Val Gln Gly Val Asn Pro Asn Thr Glu Glu
    290                 295                 300

Ala Asp Ser Arg Gln Ala Ser Asp Glu Glu Lys Phe Ser Ala Leu Ala
305                 310                 315                 320

Phe Lys Met Leu Asn Asp Lys Tyr Val Gly Gln Leu Thr Phe Ile Arg
                325                 330                 335

Val Tyr Ser Gly Val Val Lys Ser Gly Asp Thr Val Leu Asn Ser Val
            340                 345                 350

Lys Gly Thr Arg Glu Arg Ile Gly Arg Leu Val Gln Met Thr Ala Ala
        355                 360                 365

Asp Arg Thr Glu Ile Glu Glu Val Arg Ala Gly Asp Ile Ala Ala Ala
    370                 375                 380

Ile Gly Leu Lys Asp Val Thr Thr Gly Glu Thr Leu Cys Ala Glu Ser
385                 390                 395                 400

Ala Pro Ile Ile Leu Glu Arg Met Glu Phe Pro Glu Pro Val Ile His
                405                 410                 415

Ile Ala Val Glu Pro Lys Thr Lys Ala Asp Gln Glu Lys Met Gly Ile
            420                 425                 430

Ala Leu Asn Arg Leu Ala Lys Glu Asp Pro Ser Phe Arg Val Arg Thr
        435                 440                 445

Asp Glu Glu Ser Gly Gln Thr Ile Ile Ser Gly Met Gly Glu Leu His
    450                 455                 460

Leu Glu Ile Ile Val Asp Arg Met Lys Arg Glu Phe Gly Val Glu Ala
465                 470                 475                 480

Asn Ile Gly Ala Pro Gln Val Ala Tyr Arg Glu Thr Ile Arg Lys Ala
                485                 490                 495

Val Lys Ala Glu Tyr Lys His Ala Lys Gln Ser Gly Gly Lys Gly Gln
            500                 505                 510

Tyr Gly His Val Val Ile Glu Met Glu Pro Met Glu Pro Gly Gly Glu
        515                 520                 525

Gly Tyr Glu Phe Ile Asp Glu Ile Lys Gly Gly Val Ile Pro Arg Glu
    530                 535                 540

Phe Ile Pro Ser Val Asp Lys Gly Ile Arg Asp Thr Leu Pro Asn Gly
545                 550                 555                 560

Ile Val Ala Gly Tyr Pro Val Val Asp Val Arg Ile Arg Leu Val Phe
                565                 570                 575

Gly Ser Tyr His Asp Val Asp Ser Ser Gln Leu Ala Phe Glu Leu Ala
            580                 585                 590

Ala Ser Gln Ala Phe Lys Glu Gly Met Arg Gln Ala Ser Pro Ala Leu
        595                 600                 605
```

-continued

```
Leu Glu Pro Ile Met Ala Val Glu Val Glu Thr Pro Glu Glu Tyr Met
    610                 615                 620

Gly Asp Val Met Gly Asp Leu Asn Arg Arg Arg Gly Val Val Leu Gly
625                 630                 635                 640

Met Asp Asp Asp Gly Ile Gly Gly Lys Lys Val Arg Ala Glu Val Pro
                645                 650                 655

Leu Ala Glu Met Phe Gly Tyr Ser Thr Asp Leu Arg Ser Ala Thr Gln
            660                 665                 670

Gly Arg Ala Thr Tyr Ser Met Glu Phe Lys Lys Tyr Ser Glu Ala Pro
        675                 680                 685

Ala His Ile Ala Ala Ala Val Thr Glu Ala Arg Lys Gly
    690                 695                 700


<210> SEQ ID NO 24
<211> LENGTH: 334
<212> TYPE: PRT
<213> ORGANISM: Neisseria meningitidis (group B)

<400> SEQUENCE: 24

Met Ser Ile Lys Val Ala Ile Asn Gly Phe Gly Arg Ile Gly Arg Leu
  1               5                  10                  15

Ala Leu Arg Gln Ile Glu Lys Ala His Asp Ile Glu Val Val Ala Val
             20                  25                  30

Asn Asp Leu Thr Pro Ala Glu Met Leu Leu His Leu Phe Lys Tyr Asp
         35                  40                  45

Ser Thr Gln Gly Arg Phe Gln Gly Thr Ala Glu Leu Lys Asp Asp Ala
     50                  55                  60

Ile Val Val Asn Gly Lys Glu Ile Lys Val Phe Ala Asn Pro Asn Pro
 65                  70                  75                  80

Glu Glu Leu Pro Trp Gly Glu Leu Gly Val Asp Val Ile Leu Glu Cys
                 85                  90                  95

Thr Gly Phe Phe Thr Asn Lys Thr Lys Ala Glu Ala His Ile Arg Ala
            100                 105                 110

Gly Ala Arg Lys Val Val Ile Ser Ala Pro Gly Gly Asn Asp Val Lys
        115                 120                 125

Thr Val Val Tyr Gly Val Asn Gln Asp Ile Leu Asp Gly Ser Glu Thr
    130                 135                 140

Val Ile Ser Ala Ala Ser Cys Thr Thr Asn Cys Leu Ala Pro Met Ala
145                 150                 155                 160

Ala Val Leu Gln Lys Glu Phe Gly Val Val Glu Gly Leu Met Thr Thr
                165                 170                 175

Ile His Ala Tyr Thr Gly Asp Gln Asn Thr Leu Asp Ala Pro His Arg
            180                 185                 190

Lys Gly Asp Leu Arg Arg Ala Arg Ala Ala Ala Leu Asn Ile Val Pro
        195                 200                 205

Asn Ser Thr Gly Ala Ala Lys Ala Ile Gly Leu Val Ile Pro Glu Leu
    210                 215                 220

Asn Gly Lys Leu Asp Gly Ser Ala Gln Arg Val Pro Val Ala Ser Gly
225                 230                 235                 240

Ser Leu Thr Glu Leu Val Ser Ile Leu Glu Arg Pro Val Thr Lys Glu
                245                 250                 255

Glu Ile Asn Ala Ala Met Lys Ala Ala Ala Ser Glu Ser Tyr Gly Tyr
            260                 265                 270

Asn Glu Asp Gln Ile Val Ser Ser Asp Val Val Gly Ile Glu Tyr Gly
        275                 280                 285
```

```
Ser Leu Phe Asp Ala Thr Gln Thr Arg Val Met Thr Val Gly Gly Lys
    290                 295                 300

Gln Leu Val Lys Thr Val Ala Trp Tyr Asp Asn Glu Met Ser Tyr Thr
305                 310                 315                 320

Cys Gln Leu Val Arg Thr Leu Glu Tyr Phe Ala Gly Lys Ile
                325                 330


<210> SEQ ID NO 25
<211> LENGTH: 348
<212> TYPE: PRT
<213> ORGANISM: Neisseria meningitidis (group B)

<400> SEQUENCE: 25

Met Lys Met Gln Ala Val Val Val Asn Lys Asn Val Ala Gly Asp Val
  1               5                  10                  15

Glu Val Ile Glu Arg Glu Val Arg Pro Leu Glu Tyr Gly Glu Ala Leu
             20                  25                  30

Val Glu Val Glu Tyr Cys Gly Val Cys His Thr Asp Leu His Val Ala
         35                  40                  45

Ala Gly Asp Tyr Gly Glu Lys Pro Gly Arg Val Leu Gly His Glu Gly
     50                  55                  60

Ile Gly Leu Val Lys Glu Val Ala Asp Gly Val Lys Asn Leu Lys Val
 65                  70                  75                  80

Gly Asp Arg Val Ser Ile Ala Trp Leu Phe Gln Ser Cys Gly Ser Cys
                 85                  90                  95

Glu Tyr Cys Asn Thr Gly Arg Glu Thr Leu Cys Arg Ser Val Leu Asn
            100                 105                 110

Ala Gly Tyr Thr Ala Asp Gly Gly Met Ala Thr His Cys Ile Val Ser
        115                 120                 125

Ala Asp Tyr Ala Val Lys Val Pro Glu Gly Leu Asp Pro Ala Gln Ala
    130                 135                 140

Ser Ser Ile Thr Cys Ala Gly Val Thr Thr Tyr Lys Ala Ile Lys Val
145                 150                 155                 160

Ser Gly Val Arg Pro Gly Gln Trp Ile Ala Ile Tyr Gly Ala Gly Gly
                165                 170                 175

Leu Gly Asn Leu Gly Val Gln Tyr Ala Lys Lys Val Phe Gly Ala His
            180                 185                 190

Val Val Ala Ile Asp Ile Asn Asp Asp Lys Leu Ala Phe Ala Lys Glu
        195                 200                 205

Thr Gly Ala Asp Leu Val Val Asn Ala Ala Lys Glu Asp Ala Ala Lys
    210                 215                 220

Val Ile Gln Glu Lys Thr Gly Gly Ala His Ala Ala Val Val Thr Ala
225                 230                 235                 240

Val Ser Ala Ala Ala Phe Asn Ser Ala Val Asn Cys Val Arg Ala Gly
                245                 250                 255

Gly Arg Val Val Ala Ile Gly Leu Pro Pro Glu Ser Met Asp Leu Ser
            260                 265                 270

Ile Pro Arg Leu Val Leu Asp Gly Ile Glu Val Val Gly Ser Leu Val
        275                 280                 285

Gly Thr Arg Lys Asp Leu Glu Glu Ala Phe Gln Phe Gly Ala Glu Gly
    290                 295                 300

Leu Val Val Pro Lys Val Gln Leu Arg Ala Leu Asp Glu Ala Pro Ala
305                 310                 315                 320

Ile Phe Gln Glu Met Arg Glu Gly Lys Ile Thr Gly Arg Met Val Ile
```

-continued

```
                325                 330                 335

Asp Met Lys Lys Glu Cys Gly Cys Gly His His His
            340                 345


<210> SEQ ID NO 26
<211> LENGTH: 1201
<212> TYPE: PRT
<213> ORGANISM: Neisseria meningitidis (group B)

<400> SEQUENCE: 26

Met Phe His Phe Ala Phe Pro Ala Gln Thr Ala Leu Arg Gln Ala Ile
  1               5                  10                  15

Thr Asp Ala Tyr Arg Arg Asn Glu Ile Glu Ala Val Gln Asp Met Leu
            20                  25                  30

Gln Arg Ala Gln Met Ser Asp Glu Glu Arg Asn Ala Ala Ser Glu Leu
        35                  40                  45

Ala Arg Arg Leu Val Thr Gln Val Arg Ala Gly Arg Thr Lys Ala Gly
     50                  55                  60

Gly Val Asp Ala Leu Met His Glu Phe Ser Leu Ser Ser Glu Glu Gly
 65                  70                  75                  80

Ile Ala Leu Met Cys Leu Ala Glu Ala Leu Leu Arg Ile Pro Asp Asn
                 85                  90                  95

Ala Thr Arg Asp Arg Leu Ile Ala Asp Lys Ile Ser Asp Gly Asn Trp
            100                 105                 110

Lys Ser His Leu Asn Asn Ser Pro Ser Leu Phe Val Asn Ala Ala Ala
        115                 120                 125

Trp Gly Leu Leu Ile Thr Gly Lys Leu Thr Ala Thr Asn Asp Lys Gln
    130                 135                 140

Met Ser Ser Ala Leu Ser Arg Leu Ile Ser Lys Gly Gly Ala Pro Leu
145                 150                 155                 160

Ile Arg Gln Gly Val Asn Tyr Ala Met Arg Leu Leu Gly Lys Gln Phe
                165                 170                 175

Val Thr Gly Gln Thr Ile Glu Glu Ala Leu Gln Asn Gly Lys Glu Arg
            180                 185                 190

Glu Lys Met Gly Tyr Arg Phe Ser Phe Asp Met Leu Gly Glu Ala Ala
        195                 200                 205

Tyr Thr Gln Ala Asp Ala Asp Arg Tyr Tyr Arg Asp Tyr Val Glu Ala
    210                 215                 220

Ile His Ala Ile Gly Lys Asp Ala Ala Gly Gln Gly Val Tyr Glu Gly
225                 230                 235                 240

Asn Gly Ile Ser Val Lys Leu Ser Ala Ile His Pro Arg Tyr Ser Arg
                245                 250                 255

Thr Gln His Gly Arg Val Met Gly Glu Leu Leu Pro Arg Leu Lys Glu
            260                 265                 270

Leu Phe Leu Leu Gly Lys Lys Tyr Asp Ile Gly Ile Asn Ile Asp Ala
        275                 280                 285

Glu Glu Ala Asn Arg Leu Glu Leu Ser Leu Asp Leu Met Glu Ala Leu
    290                 295                 300

Val Ser Asp Pro Asp Leu Ala Gly Tyr Lys Gly Ile Gly Phe Val Val
305                 310                 315                 320

Gln Ala Tyr Gln Lys Arg Cys Pro Phe Val Ile Asp Tyr Leu Ile Asp
                325                 330                 335

Leu Ala Arg Arg Asn Asn Gln Lys Leu Met Ile Arg Leu Val Lys Gly
            340                 345                 350
```

-continued

```
Ala Tyr Trp Asp Ser Glu Ile Lys Trp Ala Gln Val Asp Gly Leu Asn
        355                 360                 365

Gly Tyr Pro Thr Tyr Thr Arg Lys Val His Thr Asp Ile Ser Tyr Leu
    370                 375                 380

Ala Cys Ala Arg Lys Leu Leu Ser Ala Gln Asp Ala Val Phe Pro Gln
385                 390                 395                 400

Phe Ala Thr His Asn Ala Tyr Thr Leu Gly Ala Ile Tyr Gln Met Gly
                405                 410                 415

Lys Gly Lys Asp Phe Glu His Gln Cys Leu His Gly Met Gly Glu Thr
            420                 425                 430

Leu Tyr Asp Gln Val Val Gly Pro Gln Asn Leu Gly Arg Arg Val Arg
        435                 440                 445

Val Tyr Ala Pro Val Gly Thr His Glu Thr Leu Leu Ala Tyr Leu Val
    450                 455                 460

Arg Arg Leu Leu Glu Asn Gly Ala Asn Ser Ser Phe Val Asn Gln Ile
465                 470                 475                 480

Val Asp Glu Asn Ile Ser Ile Asp Thr Leu Ile Arg Ser Pro Phe Asp
                485                 490                 495

Thr Ile Ala Glu Gln Gly Ile His Leu His Asn Ala Leu Pro Leu Pro
            500                 505                 510

Arg Asp Leu Tyr Gly Lys Cys Arg Leu Asn Ser Gln Gly Val Asp Leu
        515                 520                 525

Ser Asn Glu Asn Val Leu Gln Gln Leu Gln Glu Gln Met Asn Lys Ala
    530                 535                 540

Ala Ala Gln Asp Phe His Ala Ala Ser Ile Val Asn Gly Lys Ala Arg
545                 550                 555                 560

Asp Val Gly Glu Ala Gln Pro Ile Lys Asn Pro Ala Asp His Asp Asp
                565                 570                 575

Ile Val Gly Thr Val Ser Phe Ala Asp Ala Ala Leu Ala Gln Glu Ala
            580                 585                 590

Val Gly Ala Ala Val Ala Ala Phe Pro Glu Trp Ser Ala Thr Pro Ala
        595                 600                 605

Ala Glu Arg Ala Ala Cys Leu Arg Arg Phe Ala Asp Leu Leu Glu Gln
    610                 615                 620

His Thr Pro Ala Leu Met Met Leu Ala Val Arg Glu Ala Gly Lys Thr
625                 630                 635                 640

Leu Asn Asn Ala Ile Ala Glu Val Arg Glu Ala Val Asp Phe Cys Arg
                645                 650                 655

Tyr Tyr Ala Asn Glu Ala Glu His Thr Leu Pro Gln Asp Ala Lys Ala
            660                 665                 670

Val Gly Ala Ile Val Ala Ile Ser Pro Trp Asn Phe Pro Leu Ala Ile
        675                 680                 685

Phe Thr Gly Glu Val Val Ser Ala Leu Ala Ala Gly Asn Thr Val Ile
    690                 695                 700

Ala Lys Pro Ala Glu Gln Thr Ser Leu Ile Ala Gly Tyr Ala Val Ser
705                 710                 715                 720

Leu Met His Glu Ala Gly Ile Pro Thr Ser Ala Leu Gln Leu Val Leu
                725                 730                 735

Gly Ala Gly Asp Val Gly Ala Ala Leu Thr Asn Asp Ala Arg Ile Gly
            740                 745                 750

Gly Val Ile Phe Thr Gly Ser Thr Glu Val Ala Arg Leu Ile Asn Lys
        755                 760                 765

Ala Leu Ala Lys Arg Gly Asp Asn Pro Val Leu Ile Ala Glu Thr Gly
```

-continued

```
    770                 775                 780

Gly Gln Asn Ala Met Ile Val Asp Ser Thr Ala Leu Ala Glu Gln Val
785                 790                 795                 800

Cys Ala Asp Val Leu Asn Ser Ala Phe Asp Ser Ala Gly Gln Arg Cys
                805                 810                 815

Ser Ala Leu Arg Ile Leu Cys Val Gln Glu Asp Val Ala Asp Arg Met
            820                 825                 830

Leu Asp Met Ile Lys Gly Ala Met Asp Glu Leu Val Val Gly Lys Pro
        835                 840                 845

Ile Gln Leu Thr Thr Asp Val Gly Pro Val Ile Asp Ala Glu Ala Gln
    850                 855                 860

Gln Asn Leu Leu Asn His Ile Asn Lys Met Lys Gly Val Ala Lys Ser
865                 870                 875                 880

Tyr His Glu Val Lys Thr Ala Ala Asp Val Asp Ser Lys Lys Ser Thr
                885                 890                 895

Phe Val Arg Pro Ile Leu Phe Glu Leu Asn Asn Leu Asn Glu Leu Gln
            900                 905                 910

Arg Glu Val Phe Gly Pro Val Leu His Val Val Arg Tyr Arg Ala Asp
        915                 920                 925

Glu Leu Asp Asn Val Ile Asp Gln Ile Asn Ser Lys Gly Tyr Ala Leu
    930                 935                 940

Thr His Gly Val His Ser Arg Ile Glu Gly Thr Val Arg His Ile Arg
945                 950                 955                 960

Ser Arg Ile Glu Ala Gly Asn Val Tyr Val Asn Arg Asn Ile Val Gly
                965                 970                 975

Ala Val Val Gly Val Gln Pro Phe Gly Gly His Gly Leu Ser Gly Thr
            980                 985                 990

Gly Pro Lys Ala Gly Gly Ser Phe Tyr Leu Gln Lys Leu Thr Arg Ala
        995                 1000                1005

Gly Glu Trp Val Ala Pro Thr Leu Ser Gln Ile Gly Gln Ala Asp Glu
    1010                1015                1020

Ala Ala Leu Lys Arg Leu Glu Ala Leu Val His Lys Leu Pro Phe Asn
1025                1030                1035                1040

Ala Glu Glu Lys Lys Ala Ala Ala Ala Ala Leu Gly His Ala Arg Ile
                1045                1050                1055

Arg Thr Leu Arg Arg Ala Glu Thr Val Leu Thr Gly Pro Thr Gly Glu
            1060                1065                1070

Arg Asn Ser Ile Ser Trp His Ala Pro Lys Arg Val Trp Ile His Gly
        1075                1080                1085

Gly Ser Thr Val Gln Ala Phe Ala Ala Leu Thr Glu Leu Ala Ala Ser
    1090                1095                1100

Gly Ile Gln Ala Val Val Glu Pro Asp Ser Pro Leu Ala Ser Tyr Thr
1105                1110                1115                1120

Ala Asp Leu Glu Gly Leu Leu Leu Val Asn Gly Lys Pro Glu Thr Ala
                1125                1130                1135

Gly Ile Ser His Val Ala Ala Leu Ser Pro Leu Asp Ser Ala Arg Lys
            1140                1145                1150

Gln Glu Leu Ala Ala His Asp Gly Ala Leu Ile Arg Ile Leu Pro Ser
        1155                1160                1165

Glu Asn Gly Leu Asp Ile Leu Gln Val Phe Glu Glu Ile Ser Cys Ser
    1170                1175                1180

Val Asn Thr Thr Ala Ala Gly Gly Asn Ala Ser Leu Met Ala Val Ala
1185                1190                1195                1200
```

```
Asp

<210> SEQ ID NO 27
<211> LENGTH: 482
<212> TYPE: PRT
<213> ORGANISM: Neisseria meningitidis (group B)

<400> SEQUENCE: 27

Met Asn Gly Asp Ile Gly Val Ile Gly Leu Ala Val Met Gly Gln Asn
  1               5                  10                  15

Leu Ile Leu Asn Met Asn Asp Cys Gly Phe Lys Val Val Ala Tyr Asn
             20                  25                  30

Arg Thr Thr Ala Lys Val Asp Glu Phe Leu Asn Gly Ala Ala Lys Gly
         35                  40                  45

Thr Asn Ile Ile Gly Ala Tyr Ser Leu Gln Asp Leu Val Asp Lys Leu
     50                  55                  60

Glu Lys Pro Arg Lys Ile Met Met Met Val Arg Ala Gly Ser Val Val
 65                  70                  75                  80

Asp Glu Phe Ile Glu Gln Leu Leu Pro Leu Leu Glu Glu Gly Asp Ile
                 85                  90                  95

Leu Ile Asp Gly Gly Asn Ala Asn Tyr Pro Asp Thr Thr Arg Arg Thr
            100                 105                 110

His Tyr Leu Ala Glu Lys Gly Ile Leu Phe Val Gly Ala Gly Val Ser
        115                 120                 125

Gly Gly Glu Glu Gly Ala Arg Arg Gly Pro Ser Ile Met Pro Gly Gly
    130                 135                 140

Asp Lys Arg Ala Trp Asp Ala Val Lys Pro Ile Phe Gln Ala Ile Ala
145                 150                 155                 160

Ala Lys Thr Ser Gln Gly Glu Pro Cys Cys Asp Trp Val Gly Lys Asp
                165                 170                 175

Gly Ala Gly His Phe Val Lys Met Val His Asn Gly Ile Glu Tyr Gly
            180                 185                 190

Asp Met Gln Leu Ile Cys Glu Ala Tyr Gln Phe Met Lys Asp Gly Leu
        195                 200                 205

Gly Leu Ser Tyr Asp Glu Met Tyr Arg Val Phe Ala Glu Trp Asn Lys
    210                 215                 220

Thr Glu Leu Asp Ser Tyr Leu Ile Glu Ile Thr Ala Ala Ile Leu Gly
225                 230                 235                 240

Tyr Lys Asp Glu Gly Gly Glu Pro Leu Val Glu Lys Ile Leu Asp Thr
                245                 250                 255

Ala Gly Gln Lys Gly Thr Gly Lys Trp Thr Gly Ile Asn Ala Leu Asp
            260                 265                 270

Leu Gly Ile Pro Leu Thr Leu Ile Ser Glu Ala Val Phe Ala Arg Cys
        275                 280                 285

Val Ser Ser Phe Lys Glu Gln Arg Val Gln Thr Gly Lys Leu Phe Ala
    290                 295                 300

Arg Thr Val Thr Pro Val Glu Gly Gly Lys Gln Glu Trp Val Glu Ala
305                 310                 315                 320

Leu Arg Gln Ala Leu Leu Ala Ser Lys Ile Ile Ser Tyr Ala Gln Gly
                325                 330                 335

Phe Met Leu Ile Arg Glu Ala Gly Glu Ser Tyr Gly Trp Asp Leu Asp
            340                 345                 350

Tyr Gly Asn Thr Ala Leu Leu Trp Arg Glu Gly Cys Ile Ile Arg Ser
        355                 360                 365
```

```
Ala Phe Leu Ser Asn Ile Arg Asp Ala Tyr Glu Asn Asn Pro Asp Leu
    370                 375                 380

Val Phe Leu Gly Ala Asp Pro Tyr Phe Lys Asn Ile Leu Glu Asn Cys
385                 390                 395                 400

Leu Pro Ala Trp Arg Lys Val Val Ala Lys Ala Val Glu Cys Gly Ile
                405                 410                 415

Pro Met Pro Cys Met Ala Ser Ala Ile Thr Phe Leu Asp Gly Tyr Thr
            420                 425                 430

Thr Glu Arg Leu Pro Ala Asn Leu Leu Gln Ala Gln Arg Asp Tyr Phe
        435                 440                 445

Gly Ala His Thr Tyr Glu Arg Thr Asp Lys Pro Arg Gly Glu Phe Phe
    450                 455                 460

His Thr Asn Trp Thr Gly Lys Gly Gly Asp Thr Ala Ser Thr Thr Tyr
465                 470                 475                 480

Asp Ile


<210> SEQ ID NO 28
<211> LENGTH: 245
<212> TYPE: PRT
<213> ORGANISM: Neisseria meningitidis (group B)

<400> SEQUENCE: 28

Met Ala Leu Gln Asp Arg Thr Gly Gln Lys Val Pro Ser Val Val Phe
  1               5                  10                  15

Arg Thr Arg Val Gly Asp Thr Trp Lys Asp Val Ser Thr Asp Asp Leu
            20                  25                  30

Phe Lys Gly Lys Lys Val Val Val Phe Ser Leu Pro Gly Ala Phe Thr
        35                  40                  45

Pro Thr Cys Ser Ser Ser His Leu Pro Arg Tyr Asn Glu Leu Phe Gly
     50                  55                  60

Ala Phe Lys Glu Asn Gly Val Asp Ala Ile Tyr Cys Val Ser Val Asn
 65                  70                  75                  80

Asp Thr Phe Val Met Asn Ala Trp Ala Ala Glu Glu Glu Ser Asp Asn
                 85                  90                  95

Ile Tyr Met Ile Pro Asp Gly Asn Gly Glu Phe Thr Glu Gly Met Gly
            100                 105                 110

Met Leu Val Gly Lys Glu Asp Leu Gly Phe Gly Lys Arg Ser Trp Arg
        115                 120                 125

Tyr Ser Met Leu Val Asn Asp Gly Val Val Glu Lys Met Phe Ile Glu
    130                 135                 140

Pro Glu Glu Pro Gly Asp Pro Phe Lys Val Ser Asp Ala Asp Thr Met
145                 150                 155                 160

Leu Gln Phe Val Ala Pro Asp Trp Lys Ala Gln Glu Ser Val Ala Ile
                165                 170                 175

Phe Thr Lys Pro Gly Cys Gln Phe Cys Ala Lys Ala Lys Gln Ala Leu
            180                 185                 190

Gln Asp Lys Gly Leu Ser Tyr Glu Glu Ile Val Leu Gly Lys Asp Ala
        195                 200                 205

Thr Val Thr Ser Val Arg Ala Ile Thr Gly Lys Met Thr Ala Pro Gln
    210                 215                 220

Val Phe Ile Gly Gly Lys Tyr Ile Gly Gly Ser Glu Asp Leu Glu Ala
225                 230                 235                 240

Tyr Leu Ala Lys Asn
                245
```

-continued

<210> SEQ ID NO 29
<211> LENGTH: 488
<212> TYPE: PRT
<213> ORGANISM: Neisseria meningitidis (group B)

<400> SEQUENCE: 29

Met Ala Glu Ala Thr Asp Val Val Leu Val Gly Gly Gly Ile Met Ser
1 5 10 15

Ala Thr Leu Gly Val Leu Leu Lys Glu Leu Glu Pro Ser Trp Glu Ile
20 25 30

Thr Leu Ile Glu Arg Leu Glu Asp Val Ala Leu Glu Ser Ser Asn Ala
35 40 45

Trp Asn Asn Ala Gly Thr Gly His Ser Ala Leu Cys Glu Leu Asn Tyr
50 55 60

Ala Pro Leu Gly Ala Asn Gly Ile Ile Asp Pro Ala Arg Ala Leu Asn
65 70 75 80

Ile Ala Glu Gln Phe His Val Ser Arg Gln Phe Trp Ala Thr Leu Val
85 90 95

Ala Glu Gly Lys Leu Glu Asp Asn Ser Phe Ile Asn Ala Val Pro His
100 105 110

Met Ser Leu Val Met Asn Glu Asp His Cys Ser Tyr Leu Gln Lys Arg
115 120 125

Tyr Asp Ala Phe Lys Thr Gln Lys Leu Phe Glu Asn Met Glu Phe Ser
130 135 140

Thr Asp Arg Asn Lys Ile Ser Asp Trp Ala Pro Leu Met Met Arg Gly
145 150 155 160

Arg Asp Glu Asn Gln Pro Val Ala Ala Asn Tyr Ser Ala Glu Gly Thr
165 170 175

Asp Val Asp Phe Gly Arg Leu Thr Arg Gln Met Val Lys Tyr Leu Gln
180 185 190

Gly Lys Gly Val Lys Thr Glu Phe Asn Arg His Val Glu Asp Ile Lys
195 200 205

Arg Glu Ser Asp Gly Ala Trp Val Leu Lys Thr Ala Asp Thr Arg Asn
210 215 220

Pro Asp Gly Gln Leu Thr Leu Arg Thr Arg Phe Leu Phe Leu Gly Ala
225 230 235 240

Gly Gly Gly Ala Leu Thr Leu Leu Gln Lys Ser Gly Ile Pro Glu Gly
245 250 255

Lys Gly Tyr Gly Gly Phe Pro Val Ser Gly Leu Phe Phe Arg Asn Ser
260 265 270

Asn Pro Glu Thr Ala Glu Gln His Asn Ala Lys Val Tyr Gly Gln Ala
275 280 285

Ser Val Gly Ala Pro Pro Met Ser Val Pro His Leu Asp Thr Arg Asn
290 295 300

Val Asp Gly Lys Arg His Leu Met Phe Gly Pro Tyr Ala Gly Phe Arg
305 310 315 320

Ser Asn Phe Leu Lys Gln Gly Ser Leu Met Asp Leu Pro Leu Ser Ile
325 330 335

His Met Asp Asn Leu Tyr Pro Met Leu Cys Ala Gly Trp Ala Asn Met
340 345 350

Pro Leu Thr Lys Tyr Leu Leu Gly Glu Leu Arg Lys Thr Lys Glu Glu
355 360 365

Arg Phe Ala Ser Leu Leu Glu Tyr Tyr Pro Glu Ala Asn Pro Asp Asp

-continued

```
    370                 375                 380

Trp Glu Leu Ile Thr Ala Gly Gln Arg Val Gln Ile Ile Lys Lys Asp
385                 390                 395                 400

Ser Glu Lys Gly Gly Val Leu Gln Phe Gly Thr Glu Ile Val Ala His
                405                 410                 415

Ala Asp Gly Ser Leu Ala Ala Leu Leu Gly Ala Ser Pro Gly Ala Ser
            420                 425                 430

Thr Ala Val Pro Leu Met Ile Arg Leu Met His Gln Cys Phe Pro Glu
        435                 440                 445

Arg Ala Pro Ser Trp Glu Asp Arg Leu Lys Glu Leu Val Pro Gly Tyr
    450                 455                 460

Gly Ile Lys Leu Asn Glu Asn Pro Glu Arg Ala Asp Glu Ile Ile Ala
465                 470                 475                 480

Tyr Thr Ala Lys Val Leu Asp Ile
                485


<210> SEQ ID NO 30
<211> LENGTH: 602
<212> TYPE: PRT
<213> ORGANISM: Neisseria meningitidis (group B)

<400> SEQUENCE: 30

Met Arg Thr Asn Tyr Cys Gly Leu Ile Ser Glu Gln Tyr Leu Asp Gln
  1               5                  10                  15

Thr Val Thr Val Lys Gly Trp Val His Arg Arg Arg Asp His Gly Gly
             20                  25                  30

Val Ile Phe Ile Asp Leu Arg Asp Arg Glu Gly Ile Val Gln Val Val
         35                  40                  45

Ile Asp Pro Asp Thr Pro Glu Ala Phe Ala Ala Ala Asp Ser Ala Arg
     50                  55                  60

Asn Glu Tyr Val Leu Ser Ile Thr Gly Arg Val Arg Asn Arg Pro Glu
 65                  70                  75                  80

Gly Thr Thr Asn Asp Lys Met Ile Ser Gly Lys Ile Glu Ile Leu Ala
                 85                  90                  95

Lys Glu Ile Glu Val Leu Asn Ala Ala Ala Thr Pro Pro Phe Gln Ile
            100                 105                 110

Asp Asp Glu Asn Ile Ser Glu Asn Val Arg Leu Thr Asn Arg Val Ile
        115                 120                 125

Asp Leu Arg Arg Pro Val Met Gln Arg Asn Leu Arg Leu Arg Tyr Gln
    130                 135                 140

Val Ala Met Gly Val Arg Arg Tyr Leu Asp Ala Gln Gly Phe Ile Asp
145                 150                 155                 160

Ile Glu Thr Pro Met Leu Thr Arg Ser Thr Pro Glu Gly Ala Arg Asp
                165                 170                 175

Tyr Leu Val Pro Ser Arg Val His Pro Gly Glu Phe Phe Ala Leu Pro
            180                 185                 190

Gln Ser Pro Gln Leu Phe Lys Gln Leu Leu Met Val Ala Gly Phe Asp
        195                 200                 205

Arg Tyr Tyr Gln Ile Thr Lys Cys Phe Arg Asp Glu Asp Leu Arg Ala
    210                 215                 220

Asp Arg Gln Pro Glu Phe Thr Gln Ile Asp Leu Glu Thr Ser Phe Leu
225                 230                 235                 240

Asn Glu Asp Glu Ile Met Asp Ile Thr Glu Gly Met Ala Lys Gln Val
                245                 250                 255
```

-continued

```
Phe Lys Asp Ala Leu Gly Val Asp Leu Gly Asp Phe Pro Arg Met Pro
            260                 265                 270

Tyr Ser Glu Ala Met Phe Tyr Tyr Gly Ser Asp Lys Pro Asp Met Arg
        275                 280                 285

Ile Asn Leu Lys Phe Thr Glu Leu Thr Asp Leu Met Lys Thr Glu Glu
    290                 295                 300

Phe Lys Val Phe Arg Gly Ala Ala Asp Met Lys Gly Gly Arg Val Val
305                 310                 315                 320

Ala Leu Arg Val Pro Asn Gly Ala Lys Phe Ser Arg Lys Glu Ile Asp
                325                 330                 335

Glu Tyr Thr Lys Phe Val Gly Ile Tyr Gly Ala Lys Gly Leu Ala Tyr
            340                 345                 350

Ile Lys Val Asn Asp Val Gly Asn Leu Ser Asn Gly Glu Asp Ser Gly
        355                 360                 365

Leu Gln Ser Pro Ile Val Lys Phe Leu Ser Glu Asn Ala Leu Lys Glu
    370                 375                 380

Ile Ile Ala Arg Thr Gly Ala Gln Asn Gly Asp Ile Ile Phe Phe Gly
385                 390                 395                 400

Ala Asp Lys Thr Lys Val Val Asn Glu Ala Ile Gly Ala Leu Arg Ile
                405                 410                 415

Lys Val Gly Leu Glu His Gly Lys Asp Asn Gly Tyr Phe Thr Asp Glu
            420                 425                 430

Trp Lys Pro Leu Trp Val Val Asp Phe Pro Met Phe Glu Tyr Asp Glu
        435                 440                 445

Glu Ala Asp Arg Tyr Val Ala Val His His Pro Phe Thr Ala Pro Lys
    450                 455                 460

Glu Gly His Glu Asp Leu Met Val Ser Asp Pro Ala Asn Cys Leu Ala
465                 470                 475                 480

Arg Ala Tyr Asp Met Val Leu Asn Gly Trp Glu Ile Gly Gly Gly Ser
                485                 490                 495

Ile Arg Ile His Arg Ala Asp Val Gln Glu Lys Val Phe Ala Ala Leu
            500                 505                 510

Lys Ile Ser Pro Glu Glu Gln Gln Glu Lys Phe Gly Phe Leu Leu Asp
        515                 520                 525

Asn Leu Lys Phe Gly Ala Pro Pro His Gly Gly Leu Ala Phe Gly Leu
    530                 535                 540

Asp Arg Leu Val Thr Leu Met Thr Gly Ala Glu Ser Ile Arg Asp Val
545                 550                 555                 560

Ile Ala Phe Pro Lys Thr Gln Arg Ala Gln Cys Leu Leu Thr Asn Ala
                565                 570                 575

Pro Asn Ser Val Asp Asp Lys Gln Leu Arg Glu Leu Ser Leu Arg Leu
            580                 585                 590

Arg Gln Lys Ala Ala Glu Thr Lys Glu Ala
        595                 600


<210> SEQ ID NO 31
<211> LENGTH: 794
<212> TYPE: PRT
<213> ORGANISM: Neisseria meningitidis (group B)

<400> SEQUENCE: 31

Met Ala Asp Asn Tyr Val Ile Trp Phe Glu Asn Leu Arg Met Thr Asp
  1               5                  10                  15

Val Glu Arg Val Gly Gly Lys Asn Ala Ser Leu Gly Glu Met Ile Ser
             20                  25                  30
```

-continued

```
Gln Leu Thr Glu Lys Gly Val Arg Val Pro Gly Gly Phe Ala Thr Thr
        35                  40                  45

Ala Glu Ala Tyr Arg Ala Phe Leu Ala His Asn Gly Leu Ser Glu Arg
    50                  55                  60

Ile Ser Ala Ala Leu Ala Lys Leu Asp Val Glu Asp Val Ala Glu Leu
65                  70                  75                  80

Ala Arg Val Gly Lys Glu Ile Arg Gln Trp Ile Leu Asp Thr Pro Phe
                85                  90                  95

Pro Glu Gln Leu Asp Ala Glu Ile Glu Ala Ala Trp Asn Lys Met Val
            100                 105                 110

Ala Asp Ala Gly Gly Ala Asp Ile Ser Val Ala Val Arg Ser Ser Ala
        115                 120                 125

Thr Ala Glu Asp Leu Pro Asp Ala Ser Phe Ala Gly Gln Gln Glu Thr
    130                 135                 140

Phe Leu Asn Ile Asn Gly Leu Asp Asn Val Lys Glu Ala Met His His
145                 150                 155                 160

Val Phe Ala Ser Leu Tyr Asn Asp Arg Ala Ile Ser Tyr Arg Val His
                165                 170                 175

Lys Gly Phe Glu His Asp Ile Val Ala Leu Ser Ala Gly Val Gln Arg
            180                 185                 190

Met Val Arg Ser Asp Ser Gly Ala Ser Gly Val Met Phe Thr Leu Asp
        195                 200                 205

Thr Glu Ser Gly Tyr Asp Gln Val Val Phe Val Thr Ser Ser Tyr Gly
    210                 215                 220

Leu Gly Glu Asn Val Val Gln Gly Ala Val Asn Pro Asp Glu Phe Tyr
225                 230                 235                 240

Val Phe Lys Pro Thr Leu Lys Ala Gly Lys Pro Ala Ile Leu Arg Lys
                245                 250                 255

Thr Met Gly Ser Lys His Ile Lys Met Ile Phe Thr Asp Lys Ala Glu
            260                 265                 270

Ala Gly Lys Ser Val Thr Asn Val Asp Val Pro Glu Glu Asp Arg Asn
        275                 280                 285

Arg Phe Ser Ile Thr Asp Glu Glu Ile Thr Glu Leu Ala His Tyr Ala
    290                 295                 300

Leu Thr Ile Glu Lys His Tyr Gly Arg Pro Met Asp Ile Glu Trp Gly
305                 310                 315                 320

Arg Asp Gly Leu Asp Gly Lys Leu Tyr Ile Leu Gln Ala Arg Pro Glu
                325                 330                 335

Thr Val Lys Ser Gln Glu Glu Gly Asn Arg Asn Leu Arg Arg Phe Ala
            340                 345                 350

Ile Asn Gly Asp Lys Thr Val Leu Cys Glu Gly Arg Ala Ile Gly Gln
        355                 360                 365

Lys Val Gly Gln Gly Lys Val Arg Leu Ile Lys Asp Ala Ser Glu Met
    370                 375                 380

Asp Ser Val Glu Ala Gly Asp Val Leu Val Thr Asp Met Thr Asp Pro
385                 390                 395                 400

Asp Trp Glu Pro Val Met Lys Arg Ala Ser Ala Ile Val Thr Asn Arg
                405                 410                 415

Gly Gly Arg Thr Cys His Ala Ala Ile Ile Ala Arg Glu Leu Gly Ile
            420                 425                 430

Pro Ala Val Val Gly Cys Gly Asn Ala Thr Glu Leu Leu Lys Asn Gly
        435                 440                 445
```

-continued

```
Gln Glu Val Thr Val Ser Cys Ala Glu Gly Asp Thr Gly Phe Ile Tyr
    450                 455                 460

Ala Gly Leu Leu Asp Val Gln Ile Thr Asp Val Ala Leu Asp Asn Met
465                 470                 475                 480

Pro Lys Ala Pro Val Lys Val Met Met Asn Val Gly Asn Pro Glu Leu
                485                 490                 495

Ala Phe Ser Phe Ala Asn Leu Pro Ser Glu Gly Ile Gly Leu Ala Arg
            500                 505                 510

Met Glu Phe Ile Ile Asn Arg Gln Ile Gly Ile His Pro Lys Ala Leu
        515                 520                 525

Leu Glu Phe Asp Lys Gln Asp Asp Glu Leu Lys Ala Glu Ile Thr Arg
    530                 535                 540

Arg Ile Ala Gly Tyr Ala Ser Pro Val Asp Phe Tyr Val Asp Lys Ile
545                 550                 555                 560

Ala Glu Gly Val Ala Thr Leu Ala Ala Ser Val Tyr Pro Arg Lys Thr
                565                 570                 575

Ile Val Arg Met Ser Asp Phe Lys Ser Asn Glu Tyr Ala Asn Leu Val
            580                 585                 590

Gly Gly Asn Val Tyr Glu Pro His Glu Glu Asn Pro Met Leu Gly Phe
        595                 600                 605

Arg Gly Ala Ala Arg Tyr Val Ala Asp Asn Phe Lys Asp Cys Phe Ala
    610                 615                 620

Leu Glu Cys Lys Ala Leu Lys Arg Val Arg Asp Glu Met Gly Leu Thr
625                 630                 635                 640

Asn Val Glu Ile Met Ile Pro Phe Val Arg Thr Leu Gly Glu Ala Glu
                645                 650                 655

Ala Val Val Lys Ala Leu Lys Glu Asn Gly Leu Glu Arg Gly Lys Asn
            660                 665                 670

Gly Leu Arg Leu Ile Met Met Cys Glu Leu Pro Ser Asn Ala Val Leu
        675                 680                 685

Ala Glu Gln Phe Leu Gln Tyr Phe Asp Gly Phe Ser Ile Gly Ser Asn
    690                 695                 700

Asp Met Thr Gln Leu Thr Leu Gly Leu Asp Arg Asp Ser Gly Leu Val
705                 710                 715                 720

Ser Glu Ser Phe Asp Glu Arg Asn Pro Ala Val Lys Val Met Leu His
                725                 730                 735

Leu Ala Ile Ser Ala Cys Arg Lys Gln Asn Lys Tyr Val Gly Ile Cys
            740                 745                 750

Gly Gln Gly Pro Ser Asp His Pro Asp Phe Ala Lys Trp Leu Val Glu
        755                 760                 765

Glu Gly Ile Glu Ser Val Ser Leu Asn Pro Asp Thr Val Ile Glu Thr
    770                 775                 780

Trp Leu Tyr Leu Ala Asn Glu Leu Asn Lys
785                 790


<210> SEQ ID NO 32
<211> LENGTH: 427
<212> TYPE: PRT
<213> ORGANISM: Neisseria meningitidis (group B)

<400> SEQUENCE: 32

Met Ser Lys Ser Ile Lys Leu Asn Val Pro Gly Gln Ala Gly Leu Glu
  1               5                  10                  15

Leu Pro Val Leu Glu Ala Ser Ile Gly His Asp Val Val Asp Ile Arg
             20                  25                  30
```

```
Gly Leu Thr Lys Asn Thr Gly Leu Phe Ser Phe Asp Pro Gly Phe Val
        35                  40                  45

Ser Thr Ala Ser Cys Glu Ser Lys Ile Thr Tyr Ile Asp Gly Asp Gln
    50                  55                  60

Gly Leu Leu Tyr Tyr Arg Gly Tyr Pro Ile Glu Gln Leu Ala Glu Lys
65                  70                  75                  80

Ser Asp Tyr Leu Glu Val Cys Tyr Leu Leu Ile Tyr Gly Glu Leu Pro
                85                  90                  95

Thr Pro Glu Gln Lys Ala Glu Phe Asp Asn Thr Val Arg Arg His Thr
            100                 105                 110

Met Val His Glu Gln Leu Thr Trp Phe Phe Arg Gly Phe Arg Arg Asp
        115                 120                 125

Ala His Pro Met Ala Met Met Val Gly Val Val Gly Ala Leu Ser Ala
    130                 135                 140

Phe Tyr Gln Asp Ser Leu Asp Ile Ser Asn Pro Glu His Arg Lys Ile
145                 150                 155                 160

Ala Ile Tyr Arg Leu Ile Ser Lys Ile Pro Thr Ile Ala Ala Met Cys
                165                 170                 175

Tyr Arg Tyr Ser Asn Gly Leu Pro Phe Asn Tyr Pro Lys Asn Asn Leu
            180                 185                 190

Ser Tyr Ser Glu Asn Phe Leu His Met Met Phe Ala Thr Pro Cys Glu
        195                 200                 205

Asp Tyr Lys Pro Asn Pro Val Leu Ala Arg Ala Leu Asp Arg Ile Phe
    210                 215                 220

Ile Leu His Ala Asp His Glu Gln Asn Ala Ser Thr Ser Thr Val Arg
225                 230                 235                 240

Leu Ala Gly Ser Ser Gly Ala Asn Pro Phe Ala Cys Ile Ala Ala Gly
                245                 250                 255

Ile Ala Cys Leu Trp Gly Ala Ser His Gly Gly Ala Asn Glu Ala Val
            260                 265                 270

Leu Lys Met Leu Asp Glu Ile Gly Asp Val Ser Asn Val Ala Ala Tyr
        275                 280                 285

Met Glu Gly Val Lys Gln Arg Lys Tyr Arg Leu Met Gly Phe Gly His
    290                 295                 300

Arg Val Tyr Arg Asn Met Asp Pro Arg Ala Ser Ile Met Arg Glu Thr
305                 310                 315                 320

Cys Tyr Glu Val Leu Lys Glu Leu Gly Leu Glu Asp Ser Pro Lys Phe
                325                 330                 335

Lys Leu Ala Met Glu Leu Glu Gln Ile Ala Leu Lys Asp Pro Phe Phe
            340                 345                 350

Ile Glu Arg Lys Leu Tyr Pro Asn Val Asp Phe Tyr Ser Gly Ile Val
        355                 360                 365

Leu Ser Ala Leu Gly Ile Pro Thr Glu Met Phe Thr Val Ile Phe Ala
    370                 375                 380

Leu Ser Arg Ser Val Gly Trp Ile Ser His Trp His Glu Met Ile Ser
385                 390                 395                 400

Asp Pro Ser Leu Lys Ile Gly Arg Pro Arg Gln Leu Tyr Thr Gly Ser
                405                 410                 415

Glu Arg Arg Asp Tyr Val Pro Pro Gly Glu Arg
            420                 425
```

<210> SEQ ID NO 33
<211> LENGTH: 348

-continued

```
<212> TYPE: PRT
<213> ORGANISM: Neisseria meningitidis (group B)

<400> SEQUENCE: 33

Met Ser Asp Asp Lys Ser Lys Ala Leu Ala Ala Ala Leu Ala Gln Ile
  1               5                  10                  15

Glu Lys Ser Phe Gly Lys Gly Ala Ile Met Lys Met Asp Gly Ser Gln
             20                  25                  30

Gln Glu Glu Asn Leu Glu Val Ile Ser Thr Gly Ser Leu Gly Leu Asp
         35                  40                  45

Leu Ala Leu Gly Val Gly Gly Leu Pro Arg Gly Arg Ile Val Glu Ile
     50                  55                  60

Phe Gly Pro Glu Ser Ser Gly Lys Thr Thr Leu Cys Leu Glu Ala Val
 65                  70                  75                  80

Ala Gln Cys Gln Lys Asn Gly Gly Val Cys Ala Phe Val Asp Ala Glu
                 85                  90                  95

His Ala Phe Asp Pro Val Tyr Ala Arg Lys Leu Gly Val Lys Val Glu
            100                 105                 110

Glu Leu Tyr Leu Ser Gln Pro Asp Thr Gly Glu Gln Ala Leu Glu Ile
        115                 120                 125

Cys Asp Thr Leu Val Arg Ser Gly Gly Ile Asp Met Val Val Val Asp
    130                 135                 140

Ser Val Ala Ala Leu Val Pro Lys Ala Glu Ile Glu Gly Asp Met Gly
145                 150                 155                 160

Asp Ser His Val Gly Leu Gln Ala Arg Leu Met Ser Gln Ala Leu Arg
                165                 170                 175

Lys Leu Thr Gly His Ile Lys Lys Thr Asn Thr Leu Val Val Phe Ile
            180                 185                 190

Asn Gln Ile Arg Met Lys Ile Gly Val Met Phe Gly Ser Pro Glu Thr
        195                 200                 205

Thr Thr Gly Gly Asn Ala Leu Lys Phe Tyr Ser Ser Val Arg Leu Asp
    210                 215                 220

Ile Arg Arg Thr Gly Ser Ile Lys Lys Gly Glu Glu Val Leu Gly Asn
225                 230                 235                 240

Glu Thr Arg Val Lys Val Ile Lys Asn Lys Val Ala Pro Pro Phe Arg
                245                 250                 255

Gln Ala Glu Phe Asp Ile Leu Tyr Gly Glu Gly Ile Ser Trp Glu Gly
            260                 265                 270

Glu Leu Ile Asp Ile Gly Val Lys Asn Asp Ile Ile Asn Lys Ser Gly
        275                 280                 285

Ala Trp Tyr Ser Tyr Asn Gly Ala Lys Ile Gly Gln Gly Lys Asp Asn
    290                 295                 300

Val Arg Val Trp Leu Lys Glu Asn Pro Glu Val Ala Asn Glu Ile Asp
305                 310                 315                 320

Ala Lys Ile Arg Ala Leu Asn Gly Val Glu Met His Ile Thr Glu Gly
                325                 330                 335

Thr Gln Asp Glu Thr Asp Gly Glu Arg Pro Glu Glu
            340                 345


<210> SEQ ID NO 34
<211> LENGTH: 758
<212> TYPE: PRT
<213> ORGANISM: Neisseria meningitidis (group B)

<400> SEQUENCE: 34
```

-continued

```
Met Thr Thr Leu His Phe Ser Gly Phe Pro Arg Val Gly Ala Phe Arg
  1               5                  10                  15

Glu Leu Lys Phe Ala Gln Glu Lys Tyr Trp Arg Lys Glu Ile Ser Glu
             20                  25                  30

Gln Glu Leu Leu Ala Val Ala Lys Asp Leu Arg Glu Lys Asn Trp Lys
         35                  40                  45

His Gln Val Ala Ala Asn Ala Asp Phe Val Ala Val Gly Asp Phe Thr
     50                  55                  60

Phe Tyr Asp His Ile Leu Asp Leu Gln Val Ala Thr Gly Ala Ile Pro
 65                  70                  75                  80

Ala Arg Phe Gly Phe Asp Ser Gln Asn Leu Ser Leu Glu Gln Phe Phe
                 85                  90                  95

Gln Leu Ala Arg Gly Asn Lys Asp Gln Phe Ala Ile Glu Met Thr Lys
            100                 105                 110

Trp Phe Asp Thr Asn Tyr His Tyr Leu Val Pro Glu Phe His Ala Asp
        115                 120                 125

Thr Glu Phe Lys Ala Asn Ala Lys His Tyr Val Gln Gln Leu Gln Glu
    130                 135                 140

Ala Gln Ala Leu Gly Leu Lys Ala Lys Pro Thr Val Val Gly Pro Leu
145                 150                 155                 160

Thr Phe Leu Trp Val Gly Lys Glu Lys Gly Ala Val Glu Phe Asp Arg
                165                 170                 175

Leu Ser Leu Leu Pro Lys Leu Leu Pro Val Tyr Val Glu Ile Leu Thr
            180                 185                 190

Ala Leu Val Glu Ala Gly Ala Glu Trp Ile Gln Ile Asp Glu Pro Ala
        195                 200                 205

Leu Ala Val Asp Leu Pro Lys Glu Trp Val Glu Ala Tyr Lys Asp Val
    210                 215                 220

Tyr Ala Thr Leu Ser Lys Val Ser Ala Lys Ile Leu Leu Ser Thr Tyr
225                 230                 235                 240

Phe Gly Ser Val Ala Glu His Ala Ala Leu Leu Lys Ala Leu Pro Val
                245                 250                 255

Asp Gly Leu His Ile Asp Leu Val Arg Ala Pro Glu Gln Leu Asp Ala
            260                 265                 270

Phe Ala Asp Tyr Asp Lys Val Leu Ser Ala Gly Val Ile Asp Gly Arg
        275                 280                 285

Asn Ile Trp Arg Ala Asn Leu Asn Lys Val Leu Glu Thr Val Glu Pro
    290                 295                 300

Leu Gln Ala Lys Leu Gly Asp Arg Leu Trp Ile Ser Ser Ser Cys Ser
305                 310                 315                 320

Leu Leu His Thr Pro Phe Asp Leu Ser Val Glu Glu Lys Leu Lys Ala
                325                 330                 335

Asn Lys Pro Asp Leu Tyr Ser Trp Leu Ala Phe Thr Leu Gln Lys Thr
            340                 345                 350

Gln Glu Leu Arg Val Leu Lys Ala Ala Leu Asn Glu Gly Arg Asp Ser
        355                 360                 365

Val Ala Glu Glu Leu Ala Ala Ser Gln Ala Ala Ala Asp Ser Arg Ala
    370                 375                 380

Asn Ser Ser Glu Ile His Arg Ala Asp Val Ala Lys Arg Leu Ala Asp
385                 390                 395                 400

Leu Pro Ala Asn Ala Asp Gln Arg Lys Ser Pro Phe Ala Asp Arg Ile
                405                 410                 415

Lys Ala Gln Gln Ala Trp Leu Asn Leu Pro Leu Leu Pro Thr Thr Asn
```

```
            420                 425                 430

Ile Gly Ser Phe Pro Gln Thr Thr Glu Ile Arg Gln Ala Arg Ser Ala
        435                 440                 445

Phe Lys Lys Gly Glu Leu Ser Ala Ala Asp Tyr Glu Ala Ala Met Lys
    450                 455                 460

Lys Glu Ile Ala Leu Val Val Glu Glu Gln Glu Lys Leu Asp Leu Asp
465                 470                 475                 480

Val Leu Val His Gly Glu Ala Glu Arg Asn Asp Met Val Glu Tyr Phe
                485                 490                 495

Gly Glu Leu Leu Ser Gly Phe Ala Phe Thr Gln Tyr Gly Trp Val Gln
            500                 505                 510

Ser Tyr Gly Ser Arg Cys Val Lys Pro Pro Ile Ile Phe Gly Asp Val
        515                 520                 525

Ser Arg Pro Glu Ala Met Thr Val Ala Trp Ser Thr Tyr Ala Gln Ser
    530                 535                 540

Leu Thr Lys Arg Pro Met Lys Gly Met Leu Thr Gly Pro Val Thr Ile
545                 550                 555                 560

Leu Gln Trp Ser Phe Val Arg Asn Asp Ile Pro Arg Ser Thr Val Cys
                565                 570                 575

Lys Gln Ile Ala Leu Ala Leu Asn Asp Glu Val Leu Asp Leu Glu Lys
            580                 585                 590

Ala Gly Ile Lys Val Ile Gln Ile Asp Glu Pro Ala Ile Arg Glu Gly
        595                 600                 605

Leu Pro Leu Lys Arg Ala Asp Trp Asp Ala Tyr Leu Asn Trp Ala Gly
    610                 615                 620

Glu Ser Phe Arg Leu Ser Ser Ala Gly Cys Glu Asp Ser Thr Gln Ile
625                 630                 635                 640

His Thr His Met Cys Tyr Ser Glu Phe Asn Asp Ile Leu Pro Ala Ile
                645                 650                 655

Ala Ala Met Asp Ala Asp Val Ile Thr Ile Glu Thr Ser Arg Ser Asp
            660                 665                 670

Met Glu Leu Leu Thr Ala Phe Gly Glu Phe Gln Tyr Pro Asn Asp Ile
        675                 680                 685

Gly Pro Gly Val Tyr Asp Ile His Ser Pro Arg Val Pro Thr Glu Ala
    690                 695                 700

Glu Val Glu His Leu Leu Arg Lys Ala Ile Glu Val Val Pro Val Glu
705                 710                 715                 720

Arg Leu Trp Val Asn Pro Asp Cys Gly Leu Lys Thr Arg Gly Trp Lys
                725                 730                 735

Glu Thr Leu Glu Gln Leu Gln Val Met Met Asn Val Thr Arg Lys Leu
            740                 745                 750

Arg Ala Glu Leu Ala Lys
        755


<210> SEQ ID NO 35
<211> LENGTH: 382
<212> TYPE: PRT
<213> ORGANISM: Neisseria meningitidis (group B)

<400> SEQUENCE: 35

Met Pro Thr Met Gly Ala Glu Met Asn Thr Arg Asn Met Arg Tyr Ile
  1               5                  10                  15

Leu Leu Thr Gly Leu Leu Pro Met Ala Ser Ala Phe Gly Glu Thr Ala
             20                  25                  30
```

-continued

```
Leu Gln Cys Ala Ala Leu Thr Asp Asn Val Thr Arg Leu Ala Cys Tyr
        35                  40                  45

Asp Arg Ile Phe Ala Ala Gln Leu Pro Ser Ser Ala Gly Gln Glu Gly
    50                  55                  60

Gln Glu Ser Lys Ala Val Leu Asn Leu Thr Glu Thr Val Arg Ser Ser
 65                  70                  75                  80

Leu Asp Lys Gly Glu Ala Val Ile Val Val Glu Lys Gly Gly Asp Ala
                85                  90                  95

Leu Pro Ala Asp Ser Ala Gly Glu Thr Ala Asp Ile Tyr Thr Pro Leu
            100                 105                 110

Ser Leu Met Tyr Asp Leu Asp Lys Asn Asp Leu Arg Gly Leu Leu Gly
        115                 120                 125

Val Arg Glu His Asn Pro Met Tyr Leu Met Pro Leu Trp Tyr Asn Asn
    130                 135                 140

Ser Pro Asn Tyr Ala Pro Gly Ser Pro Thr Arg Gly Thr Thr Val Gln
145                 150                 155                 160

Glu Lys Phe Gly Gln Gln Lys Arg Ala Glu Thr Lys Leu Gln Val Ser
                165                 170                 175

Phe Lys Ser Lys Ile Ala Glu Asp Leu Phe Lys Thr Arg Ala Asp Leu
            180                 185                 190

Trp Phe Gly Tyr Thr Gln Arg Ser Asp Trp Gln Ile Tyr Asn Gln Gly
        195                 200                 205

Arg Lys Ser Ala Pro Phe Arg Asn Thr Asp Tyr Lys Pro Glu Ile Phe
    210                 215                 220

Leu Thr Gln Pro Val Lys Ala Asp Leu Pro Phe Gly Gly Arg Leu Arg
225                 230                 235                 240

Met Leu Gly Ala Gly Phe Val His Gln Ser Asn Gly Gln Ser Arg Pro
                245                 250                 255

Glu Ser Arg Ser Trp Asn Arg Ile Tyr Ala Met Ala Gly Met Glu Trp
            260                 265                 270

Gly Lys Leu Thr Val Ile Pro Arg Val Trp Val Arg Ala Phe Asp Gln
        275                 280                 285

Ser Gly Asp Lys Asn Asp Asn Pro Asp Ile Ala Asp Tyr Met Gly Tyr
    290                 295                 300

Gly Asp Val Lys Leu Gln Tyr Arg Leu Asn Asp Arg Gln Asn Val Tyr
305                 310                 315                 320

Ser Val Leu Arg Tyr Asn Pro Lys Thr Gly Tyr Gly Ala Ile Glu Ala
                325                 330                 335

Ala Tyr Thr Phe Pro Ile Lys Gly Lys Leu Lys Gly Val Val Arg Gly
            340                 345                 350

Phe His Gly Tyr Gly Glu Ser Leu Ile Asp Tyr Asn His Lys Gln Asn
        355                 360                 365

Gly Ile Gly Ile Gly Leu Met Phe Asn Asp Leu Asp Gly Ile
    370                 375                 380
```

<210> SEQ ID NO 36
<211> LENGTH: 456
<212> TYPE: PRT
<213> ORGANISM: Neisseria meningitidis (group B)

<400> SEQUENCE: 36

```
Met Ile Asn Pro Ile Ala Ser Leu Ser Pro Leu Asp Gly Arg Tyr Ala
  1               5                  10                  15

Gln Ser Val Glu Ala Leu Arg Pro Ile Phe Ser Glu Tyr Gly Leu Met
            20                  25                  30
```

```
Lys Ala Arg Val Lys Val Glu Leu Asn Trp Leu Lys Ala Leu Ala Ala
        35                  40                  45

Glu Pro Lys Ile Ala Glu Val Pro Pro Phe Ser Ala Glu Thr Leu Ala
    50                  55                  60

Glu Ile Asp Thr Val Ile Glu Asn Phe Ser Leu Glu Asp Ala Ala Ala
 65                  70                  75                  80

Val Lys Ala Ile Glu Ala Thr Thr Asn His Asp Val Lys Ala Ile Glu
                 85                  90                  95

Tyr Trp Leu Lys Lys Arg Phe Ala Glu Val Pro Glu Val Ala Ala Val
            100                 105                 110

Ser Glu Phe Ile His Phe Ala Cys Thr Ser Glu Asp Ile Asn Asn Leu
        115                 120                 125

Ser His Ala Leu Met Leu Gln Glu Ala Arg Glu Ala Val Leu Leu Pro
    130                 135                 140

Lys Leu Ala Glu Ile Ile Glu Lys Leu Thr Ala Met Ala His Asp Leu
145                 150                 155                 160

Ala Ala Val Pro Met Met Ser Arg Thr His Gly Gln Pro Ala Thr Pro
                165                 170                 175

Thr Thr Leu Gly Lys Glu Thr Ala Asn Val Val Tyr Arg Leu Gln Arg
            180                 185                 190

Gln Phe Lys Asn Leu Gln Ala Gln Glu Phe Leu Gly Lys Ile Asn Gly
        195                 200                 205

Ala Val Gly Asn Tyr Asn Ala His Met Val Ala Tyr Pro Asp Val Asp
    210                 215                 220

Trp Glu Thr His Cys Arg Asn Phe Val Glu Ile Ser Leu Gly Leu Thr
225                 230                 235                 240

Phe Asn Pro Tyr Thr Ile Gln Ile Glu Pro His Asp Tyr Met Ala Glu
                245                 250                 255

Phe Phe Gln Thr Leu Ser Arg Ile Asn Thr Ile Leu Ile Asp Phe Asn
            260                 265                 270

Arg Asp Val Trp Gly Tyr Ile Ser Leu Gly Tyr Phe Lys Gln Lys Val
        275                 280                 285

Lys Ala Gly Glu Val Gly Ser Ser Thr Met Pro His Lys Val Asn Pro
    290                 295                 300

Ile Asp Phe Glu Asn Ser Glu Gly Asn Leu Gly Met Ala Asn Ala Val
305                 310                 315                 320

Leu Gly Phe Leu Ser Glu Lys Leu Pro Ile Ser Arg Trp Gln Arg Asp
                325                 330                 335

Leu Thr Asp Ser Thr Val Leu Arg Asn Met Gly Val Gly Val Gly Tyr
            340                 345                 350

Ala Val Leu Gly Phe Ala Ala His Leu Arg Gly Leu Asn Lys Leu Glu
        355                 360                 365

Pro Asn Pro Ala Ala Leu Ala Ala Asp Leu Asp Ala Thr Trp Glu Leu
    370                 375                 380

Leu Ala Glu Pro Ile Gln Thr Val Met Arg Arg Tyr Gly Val Ala Asn
385                 390                 395                 400

Pro Tyr Glu Lys Leu Lys Asp Leu Thr Arg Gly Lys Gly Gly Ile Thr
                405                 410                 415

Pro Glu Val Leu Lys Gly Phe Ile Gly Leu Leu Glu Ile Pro Ala Glu
            420                 425                 430

Ala Lys Ala Lys Leu Leu Glu Leu Thr Pro Ala Leu Tyr Val Gly Lys
        435                 440                 445
```

-continued

```
Ala Glu Ala Leu Ala Lys Arg Ile
    450                 455


<210> SEQ ID NO 37
<211> LENGTH: 415
<212> TYPE: PRT
<213> ORGANISM: Neisseria meningitidis (group B)

<400> SEQUENCE: 37

Met Ser Gln Arg Arg Val Val Ile Thr Gly Leu Gly Gln Val Ser Pro
  1               5                  10                  15

Val Gly Asn Thr Val Ala Glu Ala Trp Asp Thr Leu Leu Thr Gly Lys
             20                  25                  30

Ser Gly Ile Gly Ala Ile Thr Arg Phe Asp Thr Ser Asp Ile Asn Ser
         35                  40                  45

Arg Val Ala Gly Glu Val Arg Gly Phe Asp Ile Gly Gln Tyr Ile Ser
     50                  55                  60

Ala Lys Glu Ala Arg Arg Met Asp Val Phe Ile His Tyr Gly Ile Ala
 65                  70                  75                  80

Ala Ala Leu Gln Ala Ile Ala Asp Ser Gly Leu Asp Asp Val Glu Asn
                 85                  90                  95

Leu Asp Lys Asp Arg Ile Gly Val Asn Ile Gly Ser Gly Ile Gly Gly
            100                 105                 110

Leu Pro Gly Ile Glu Val Thr Gly Lys Ala Val Ile Glu Gly Gly Ala
        115                 120                 125

Arg Lys Ile Asn Pro Phe Phe Ile Pro Gly Ser Leu Ile Asn Leu Ile
    130                 135                 140

Ser Gly His Val Thr Ile Leu Lys Gly Tyr Arg Gly Pro Ser Tyr Gly
145                 150                 155                 160

Met Val Ser Ala Cys Thr Thr Gly Ala His Ala Ile Gly Asp Ser Leu
                165                 170                 175

Arg Met Ile Lys Tyr Gly Asp Ala Asp Ile Met Val Ala Gly Gly Ala
            180                 185                 190

Glu Gly Ala Ile Ser Thr Leu Gly Val Gly Gly Phe Ala Ala Met Lys
        195                 200                 205

Ala Leu Ser Thr Arg Asn Asp Asp Pro Ala Thr Ala Ser Arg Pro Trp
    210                 215                 220

Asp Lys Gly Arg Asp Gly Phe Val Ile Gly Glu Gly Ala Gly Ile Leu
225                 230                 235                 240

Val Leu Glu Glu Leu Glu His Ala Lys Lys Arg Gly Ala Lys Ile Tyr
                245                 250                 255

Ala Glu Ile Val Gly Phe Gly Met Ser Ser Asp Ala Tyr His Ile Thr
            260                 265                 270

Ala Pro Asn Glu Glu Gly Pro Ala Leu Ala Val Thr Arg Ala Leu Lys
        275                 280                 285

Asp Ala Gly Ile Asn Pro Glu Asp Val Asp Tyr Val Asn Ala His Gly
    290                 295                 300

Thr Ser Thr Pro Leu Gly Asp Ala Asn Glu Thr Lys Ala Leu Lys Arg
305                 310                 315                 320

Ala Phe Gly Glu His Ala Tyr Lys Thr Val Val Ser Ser Thr Lys Ser
                325                 330                 335

Met Thr Gly His Leu Leu Gly Ala Ala Gly Gly Val Glu Ala Val Tyr
            340                 345                 350

Ser Ile Leu Ala Ile His Asp Gly Lys Ile Pro Pro Thr Ile Asn Ile
        355                 360                 365
```

-continued

```
Phe Glu Gln Asp Val Glu Ala Gly Cys Asp Leu Asp Tyr Cys Ala Asn
    370                 375                 380

Glu Ala Arg Asp Ala Glu Ile Asp Val Ala Ile Ser Asn Ser Phe Gly
385                 390                 395                 400

Phe Gly Gly Thr Asn Gly Thr Leu Val Phe Lys Arg Phe Lys Gly
                405                 410                 415


<210> SEQ ID NO 38
<211> LENGTH: 861
<212> TYPE: PRT
<213> ORGANISM: Neisseria meningitidis (group B)

<400> SEQUENCE: 38

Met Leu Glu Ala Tyr Arg Lys Ala Ala Ala Glu Arg Ala Ala Leu Gly
  1               5                  10                  15

Ile Pro Ala Leu Pro Leu Thr Ala Gln Gln Thr Ala Asp Leu Val Glu
            20                  25                  30

Leu Leu Lys Ser Pro Pro Ala Gly Glu Gly Glu Phe Leu Val Glu Leu
        35                  40                  45

Leu Ala His Arg Val Pro Pro Gly Val Asp Asp Ala Ala Lys Val Lys
     50                  55                  60

Ala Ser Phe Leu Ala Ala Val Ala Glu Gly Ser Ala Ser Ser Pro Leu
 65                  70                  75                  80

Ile Ser Pro Glu Tyr Ala Thr Glu Leu Leu Gly Thr Met Leu Gly Gly
                 85                  90                  95

Tyr Asn Ile His Ala Leu Ile Glu Leu Leu Asp Asp Asp Lys Leu Ala
            100                 105                 110

Pro Ile Ala Ala Lys Gly Phe Lys His Thr Leu Leu Met Phe Asp Ser
        115                 120                 125

Phe His Asp Val Gln Glu Lys Ala Glu Lys Gly Asn Lys Tyr Ala Gln
    130                 135                 140

Glu Val Leu Gln Ser Trp Ala Asp Ala Glu Trp Phe Ala Ser Arg Ala
145                 150                 155                 160

Lys Val Pro Glu Lys Ile Thr Val Thr Val Phe Lys Val Asp Gly Glu
                165                 170                 175

Thr Asn Thr Asp Asp Leu Ser Pro Ala Pro Asp Ala Trp Ser Arg Pro
            180                 185                 190

Asp Ile Pro Leu His Ala Leu Ala Met Leu Lys Asn Pro Arg Asp Gly
        195                 200                 205

Ile Thr Pro Asp Lys Pro Gly Glu Val Gly Pro Ile Lys Leu Leu Glu
    210                 215                 220

Glu Leu Lys Ala Lys Gly His Pro Val Ala Tyr Val Gly Asp Val Val
225                 230                 235                 240

Gly Thr Gly Ser Ser Arg Lys Ser Ala Thr Asn Ser Val Ile Trp His
                245                 250                 255

Thr Gly Glu Asp Ile Pro Phe Val Pro Asn Lys Arg Phe Gly Gly Val
            260                 265                 270

Cys Leu Gly Gly Lys Ile Ala Pro Ile Phe Phe Asn Thr Gln Glu Asp
        275                 280                 285

Ser Gly Ala Leu Pro Ile Glu Val Asp Val Ser Ala Leu Lys Met Gly
    290                 295                 300

Asp Val Val Asp Ile Leu Pro Tyr Glu Gly Lys Ile Val Lys Asn Gly
305                 310                 315                 320

Glu Thr Val Ala Glu Phe Glu Leu Lys Ser Gln Val Leu Leu Asp Glu
```

-continued

```
                325                 330                 335

Val Gln Ala Gly Gly Arg Ile Asn Leu Ile Ile Gly Arg Gly Leu Thr
            340                 345                 350

Ala Lys Ala Arg Glu Ala Leu Lys Leu Pro Ala Ser Thr Ala Phe Arg
        355                 360                 365

Leu Pro Gln Ala Pro Ala Glu Ser Lys Ala Gly Phe Thr Leu Ala Gln
    370                 375                 380

Lys Met Val Gly Arg Ala Cys Gly Leu Pro Glu Gly Gln Gly Val Arg
385                 390                 395                 400

Pro Gly Thr Tyr Cys Glu Pro Arg Met Thr Thr Val Gly Ser Gln Asp
                405                 410                 415

Thr Thr Gly Pro Met Thr Arg Asp Glu Leu Lys Asp Leu Ala Cys Leu
            420                 425                 430

Gly Phe Ser Ala Asp Met Val Met Gln Ser Phe Cys His Thr Ala Ala
        435                 440                 445

Tyr Pro Lys Pro Val Asp Val Lys Thr His Lys Glu Leu Pro Ala Phe
    450                 455                 460

Ile Ser Thr Arg Gly Gly Val Ser Leu Arg Pro Gly Asp Gly Val Ile
465                 470                 475                 480

His Ser Trp Leu Asn Arg Leu Leu Leu Pro Asp Thr Val Gly Thr Gly
                485                 490                 495

Gly Asp Ser His Thr Arg Phe Pro Ile Gly Ile Ser Phe Pro Ala Gly
            500                 505                 510

Ser Gly Leu Val Ala Phe Ala Ala Ala Thr Gly Val Met Pro Leu Asp
        515                 520                 525

Met Pro Glu Ser Val Leu Val Arg Phe Ser Gly Lys Leu Gln Pro Gly
    530                 535                 540

Val Thr Leu Arg Asp Leu Val Asn Ala Ile Pro Leu Tyr Ala Ile Lys
545                 550                 555                 560

Gln Gly Leu Leu Thr Val Ala Lys Ala Gly Lys Lys Asn Ile Phe Ser
                565                 570                 575

Gly Arg Ile Leu Glu Ile Glu Gly Leu Pro Asp Leu Lys Val Glu Gln
            580                 585                 590

Ala Phe Glu Leu Thr Asp Ala Ser Ala Glu Arg Ser Ala Ala Gly Cys
        595                 600                 605

Thr Val Lys Leu Asn Lys Glu Pro Ile Ile Glu Tyr Met Lys Ser Asn
    610                 615                 620

Val Val Leu Met Lys Asn Met Ile Ala Asn Gly Tyr Gln Asp Pro Arg
625                 630                 635                 640

Thr Leu Glu Arg Arg Ile Lys Ala Met Glu Lys Trp Leu Ala Asn Pro
                645                 650                 655

Glu Leu Leu Glu Ala Asp Lys Asp Ala Glu Tyr Ala Ala Val Ile Glu
            660                 665                 670

Ile Asn Met Asp Asp Ile Lys Glu Pro Ile Ile Ala Cys Pro Asn Asp
        675                 680                 685

Pro Asp Asp Val Cys Phe Met Ser Glu Arg Ser Gly Thr Lys Ile Asp
    690                 695                 700

Glu Val Phe Ile Gly Ser Cys Met Thr Asn Ile Gly His Phe Arg Ala
705                 710                 715                 720

Ala Ser Lys Leu Leu Glu Gly Lys Ser Asp Ile Pro Val Arg Leu Trp
                725                 730                 735

Val Ala Pro Pro Thr Lys Met Asp Ala Lys Glu Leu Ser Asp Glu Gly
            740                 745                 750
```

```
His Tyr Gly Val Leu Gly Arg Ala Gly Ala Arg Met Glu Met Pro Gly
        755                 760                 765

Cys Ser Leu Cys Met Gly Asn Gln Ala Gln Val His Glu Gly Ala Thr
    770                 775                 780

Val Met Ser Thr Ser Thr Arg Asn Phe Pro Asn Arg Leu Gly Lys Asn
785                 790                 795                 800

Thr Phe Val Tyr Leu Gly Ser Ala Glu Leu Ala Ala Ile Cys Ser Lys
                805                 810                 815

Leu Gly Lys Ile Pro Thr Val Glu Glu Tyr Gln Ala Asn Ile Gly Ile
            820                 825                 830

Ile Asn Glu Gln Gly Asp Lys Ile Tyr Arg Tyr Met Asn Phe Asn Glu
        835                 840                 845

Ile Asp Ser Tyr Asn Glu Val Ala Glu Thr Val Asn Val
    850                 855                 860


<210> SEQ ID NO 39
<211> LENGTH: 388
<212> TYPE: PRT
<213> ORGANISM: Neisseria meningitidis (group B)

<400> SEQUENCE: 39

Met Asn Leu His Glu Tyr Gln Ala Lys Glu Leu Leu Ala Ser Tyr Gly
  1               5                  10                  15

Leu Pro Val Gln Gly Gly Ile Leu Ala His Asn Gly Glu Glu Ala Ala
             20                  25                  30

Ala Ala Tyr Asp Lys Leu Gly Gly Lys Phe Ala Val Val Lys Ala Gln
         35                  40                  45

Val His Ala Gly Gly Arg Gly Lys Ala Gly Gly Val Lys Val Val Lys
     50                  55                  60

Ser Arg Glu Glu Ala Lys Glu Val Ala Glu Ser Leu Ile Gly Thr Asn
 65                  70                  75                  80

Leu Val Thr Tyr Gln Thr Asp Ala Asn Gly Gln Pro Val Asn Ser Val
                 85                  90                  95

Leu Val Cys Glu Asp Met Tyr Pro Val Gln Thr Glu Leu Tyr Leu Gly
            100                 105                 110

Ala Val Val Asp Arg Ser Thr Arg Arg Ile Thr Phe Met Ala Ser Thr
        115                 120                 125

Glu Gly Gly Val Glu Ile Glu Lys Val Ala Ala Glu Thr Pro Glu Lys
    130                 135                 140

Ile Phe Lys Val Thr Val Asp Pro Leu Val Gly Leu Gln Pro Cys Gln
145                 150                 155                 160

Ala Arg Glu Val Ala Phe Gln Leu Gly Leu Lys Asp Lys Gln Ile Asn
                165                 170                 175

Glu Phe Val Lys Leu Met Thr Gly Ala Tyr Lys Ala Phe Val Glu Asn
            180                 185                 190

Asp Phe Ala Leu Phe Glu Val Asn Pro Leu Ala Val Arg Glu Asn Gly
        195                 200                 205

Ala Leu Ala Cys Val Asp Gly Lys Ile Gly Ile Asp Ser Asn Ala Leu
    210                 215                 220

Tyr Arg Leu Pro Lys Ile Ala Glu Leu Arg Asp Lys Ser Gln Glu Asn
225                 230                 235                 240

Glu Arg Glu Leu Lys Ala Ser Glu Phe Asp Leu Asn Tyr Val Ala Leu
                245                 250                 255

Glu Gly Asn Ile Gly Cys Met Val Asn Gly Ala Gly Leu Ala Met Ala
```

```
            260                 265                 270

Thr Met Asp Ile Ile Lys Leu Lys Gly Gly Gln Pro Ala Asn Phe Leu
        275                 280                 285

Asp Val Gly Gly Gly Ala Thr Lys Asp Arg Val Val Glu Ala Phe Lys
    290                 295                 300

Leu Ile Leu Glu Asp Lys Ser Val Gln Gly Val Leu Ile Asn Ile Phe
305                 310                 315                 320

Gly Gly Ile Val Arg Cys Asp Met Ile Ala Glu Ala Ile Val Ala Ala
                325                 330                 335

Val Lys Glu Ile Asn Val Asn Val Pro Val Val Val Arg Leu Glu Gly
            340                 345                 350

Asn Asn Ala Glu Leu Gly Ala Lys Ile Leu Asn Glu Ser Gly Leu Lys
        355                 360                 365

Leu Thr Ser Ala Asp Gly Leu Asn Asp Ala Ala Glu Lys Ile Val Ala
    370                 375                 380

Ala Val Asn Ala
385


<210> SEQ ID NO 40
<211> LENGTH: 435
<212> TYPE: PRT
<213> ORGANISM: Neisseria meningitidis (group B)

<400> SEQUENCE: 40

Met Lys Pro Val Asn Ile Gly Leu Leu Gly Leu Gly Thr Val Gly Gly
  1               5                  10                  15

Gly Thr Ala Ala Val Leu Arg Asp Asn Ala Glu Glu Ile Ser Arg Arg
            20                  25                  30

Leu Gly Arg Glu Ile Arg Ile Ser Ala Val Cys Asp Leu Ser Glu Glu
        35                  40                  45

Lys Ala Arg Gln Thr Cys Pro Ser Ala Ala Phe Val Lys Asp Pro Phe
    50                  55                  60

Glu Leu Val Ala Arg Glu Asp Val Asp Val Val Val Glu Leu Phe Gly
 65                  70                  75                  80

Gly Thr Gly Ile Ala Lys Asp Ala Val Leu Lys Ala Ile Glu Asn Gly
                85                  90                  95

Lys His Ile Val Thr Ala Asn Lys Lys Leu Leu Ala Glu Tyr Gly Asn
            100                 105                 110

Glu Ile Phe Pro Leu Ala Glu Lys Gln Asn Val Ile Val Gln Phe Glu
        115                 120                 125

Ala Ala Val Ala Gly Gly Ile Pro Ile Ile Lys Ala Leu Arg Glu Gly
    130                 135                 140

Leu Ala Ala Asn Arg Ile Lys Ser Ile Ala Gly Ile Ile Asn Gly Thr
145                 150                 155                 160

Ser Asn Phe Ile Leu Ser Glu Met Arg Glu Lys Gly Ser Ala Phe Ala
                165                 170                 175

Asp Val Leu Lys Glu Ala Gln Ala Leu Gly Tyr Ala Glu Ala Asp Pro
            180                 185                 190

Thr Phe Asp Ile Glu Gly Asn Asp Ala Gly His Lys Ile Thr Ile Met
        195                 200                 205

Ser Ala Leu Ala Phe Gly Thr Pro Met Asn Phe Ser Ala Cys Tyr Leu
    210                 215                 220

Glu Gly Ile Ser Lys Leu Asp Ser Arg Asp Ile Lys Tyr Ala Glu Glu
225                 230                 235                 240
```

-continued

```
Leu Gly Tyr Arg Ile Lys Leu Leu Gly Ile Thr Arg Lys Thr Gly Lys
                245                 250                 255

Gly Ile Glu Leu Arg Val His Pro Thr Leu Ile Pro Glu Ser Arg Leu
            260                 265                 270

Leu Ala Asn Val Asn Gly Val Met Asn Ala Val Arg Val Asn Ala Asp
        275                 280                 285

Met Val Gly Glu Thr Leu Tyr Tyr Gly Ala Gly Ala Gly Ala Leu Pro
    290                 295                 300

Thr Ala Ser Ala Val Val Ala Asp Ile Ile Asp Ile Ala Arg Leu Val
305                 310                 315                 320

Glu Ala Asp Thr Ala His Arg Val Pro His Leu Ala Phe Gln Pro Ala
                325                 330                 335

Gln Val Gln Ala Gln Thr Ile Leu Pro Met Asp Glu Ile Thr Ser Ser
            340                 345                 350

Tyr Tyr Leu Arg Val Gln Ala Lys Asp Glu Pro Gly Thr Leu Gly Gln
        355                 360                 365

Ile Ala Ala Leu Leu Ala Gln Glu Asn Val Ser Ile Glu Ala Leu Ile
    370                 375                 380

Gln Lys Gly Val Ile Asp Gln Thr Thr Ala Glu Ile Val Ile Leu Thr
385                 390                 395                 400

His Ser Thr Val Glu Lys His Ile Lys Ser Ala Ile Ala Ala Ile Glu
                405                 410                 415

Ala Leu Asp Cys Val Glu Lys Pro Ile Thr Met Ile Arg Met Glu Ser
            420                 425                 430

Leu His Asp
        435
```

<210> SEQ ID NO 41
<211> LENGTH: 201
<212> TYPE: PRT
<213> ORGANISM: Neisseria meningitidis (group B)

<400> SEQUENCE: 41

```
Met Met Thr Leu Tyr Ser Gly Ile Thr Cys Pro Phe Ser His Arg Cys
  1               5                  10                  15

Arg Phe Val Leu Tyr Glu Lys Gly Met Asp Phe Glu Ile Lys Asp Val
            20                  25                  30

Asp Ile Tyr Asn Lys Pro Glu Asp Leu Ala Val Met Asn Pro Tyr Asn
        35                  40                  45

Gln Val Pro Val Leu Val Glu Arg Asp Leu Val Leu His Glu Ser Asn
     50                  55                  60

Ile Ile Asn Glu Tyr Ile Asp Glu Arg Phe Pro His Pro Gln Leu Met
 65                  70                  75                  80

Pro Gly Asp Pro Val Met Arg Gly Arg Gly Arg Leu Val Leu Tyr Arg
                 85                  90                  95

Met Glu Lys Glu Leu Phe Asn His Val Gln Val Leu Glu Asn Pro Ala
            100                 105                 110

Ala Thr Asn Lys Glu Gln Ala Lys Ala Arg Glu Ala Ile Gly Asn Gly
        115                 120                 125

Leu Thr Met Leu Ala Pro Ser Phe Ser Lys Ser Lys Tyr Ile Leu Gly
    130                 135                 140

Glu Asp Phe Ser Met Ile Asp Val Ala Leu Ala Pro Leu Leu Trp Arg
145                 150                 155                 160

Leu Asp His Tyr Asp Val Lys Leu Gly Lys Ser Ala Ala Pro Leu Leu
                165                 170                 175
```

```
Lys Tyr Ala Glu Arg Ile Phe Gln Arg Glu Ala Phe Ile Glu Ala Leu
            180                 185                 190

Thr Pro Ala Glu Lys Ala Met Arg Lys
        195                 200
```

<210> SEQ ID NO 42
<211> LENGTH: 213
<212> TYPE: PRT
<213> ORGANISM: Neisseria meningitidis (group B)

<400> SEQUENCE: 42

```
Met Thr Asp Phe Arg Gln Asp Phe Leu Lys Phe Ser Leu Ala Gln Asn
  1               5                  10                  15

Val Leu Lys Phe Gly Glu Phe Thr Thr Lys Ala Gly Arg Arg Ser Pro
            20                  25                  30

Tyr Phe Phe Asn Ala Gly Leu Phe Asn Asp Gly Leu Ser Thr Leu Gln
        35                  40                  45

Leu Ala Lys Phe Tyr Ala Gln Ser Ile Ile Glu Ser Gly Ile Arg Phe
    50                  55                  60

Asp Met Leu Phe Gly Pro Ala Tyr Lys Gly Ile Ile Leu Ala Ala Ala
 65                  70                  75                  80

Thr Ala Met Met Leu Ala Glu Lys Gly Val Asn Val Pro Phe Ala Tyr
                85                  90                  95

Asn Arg Lys Glu Ala Lys Asp His Gly Glu Gly Gly Val Leu Val Gly
            100                 105                 110

Ala Pro Leu Lys Gly Arg Val Leu Ile Ile Asp Asp Val Ile Ser Ala
        115                 120                 125

Gly Thr Ser Val Arg Glu Ser Ile Lys Leu Ile Glu Ala Glu Gly Ala
    130                 135                 140

Thr Pro Ala Gly Val Ala Ile Ala Leu Asp Arg Met Glu Lys Gly Thr
145                 150                 155                 160

Gly Glu Leu Ser Ala Val Gln Glu Val Glu Lys Gln Tyr Gly Leu Pro
                165                 170                 175

Val Ala Pro Ile Ala Ser Leu Asn Asp Leu Phe Ile Leu Leu Gln Asn
            180                 185                 190

Asn Pro Glu Phe Gly Gln Phe Leu Glu Pro Val Arg Ala Tyr Arg Arg
        195                 200                 205

Gln Tyr Gly Val Glu
    210
```

<210> SEQ ID NO 43
<211> LENGTH: 444
<212> TYPE: PRT
<213> ORGANISM: Neisseria meningitidis (group B)

<400> SEQUENCE: 43

```
Met Thr Asp Leu Asn Thr Leu Phe Ala Asn Leu Lys Gln Arg Asn Pro
  1               5                  10                  15

Asn Gln Glu Pro Phe His Gln Ala Val Glu Glu Val Phe Met Ser Leu
            20                  25                  30

Asp Pro Phe Leu Ala Lys Asn Pro Lys Tyr Thr Gln Gln Ser Leu Leu
        35                  40                  45

Glu Arg Ile Val Glu Pro Glu Arg Val Val Met Phe Arg Val Thr Trp
    50                  55                  60

Gln Asp Asp Lys Gly Gln Val Gln Val Asn Arg Gly Tyr Arg Val Gln
 65                  70                  75                  80
```

-continued

```
Met Ser Ser Ala Ile Gly Pro Tyr Lys Gly Gly Leu Arg Phe His Pro
                85                  90                  95

Thr Val Asp Leu Gly Val Leu Lys Phe Leu Ala Phe Glu Gln Val Phe
            100                 105                 110

Lys Asn Ala Leu Thr Thr Leu Pro Met Gly Gly Gly Lys Gly Gly Ser
        115                 120                 125

Asp Phe Asp Pro Lys Gly Lys Ser Asp Ala Glu Val Met Arg Phe Cys
    130                 135                 140

Gln Ala Phe Met Thr Glu Leu Tyr Arg His Ile Gly Ala Asp Thr Asp
145                 150                 155                 160

Val Pro Ala Gly Asp Ile Gly Val Gly Gly Arg Glu Ile Gly Tyr Leu
                165                 170                 175

Phe Gly Gln Tyr Lys Lys Ile Arg Asn Glu Phe Ser Ser Val Leu Thr
            180                 185                 190

Gly Lys Gly Leu Glu Trp Gly Gly Ser Leu Ile Arg Pro Glu Ala Thr
        195                 200                 205

Gly Tyr Gly Cys Val Tyr Phe Ala Gln Ala Met Leu Gln Thr Arg Asn
    210                 215                 220

Asp Ser Phe Glu Gly Lys Arg Val Leu Ile Ser Gly Ser Gly Asn Val
225                 230                 235                 240

Ala Gln Tyr Ala Ala Glu Lys Ala Ile Gln Leu Gly Ala Lys Val Leu
                245                 250                 255

Thr Val Ser Asp Ser Asn Gly Phe Val Leu Phe Pro Asp Ser Gly Met
            260                 265                 270

Thr Glu Ala Gln Leu Ala Ala Leu Ile Glu Leu Lys Glu Val Arg Arg
        275                 280                 285

Glu Arg Val Ala Thr Tyr Ala Lys Glu Gln Gly Leu Gln Tyr Phe Glu
    290                 295                 300

Lys Gln Lys Pro Trp Gly Val Ala Ala Glu Ile Ala Leu Pro Cys Ala
305                 310                 315                 320

Thr Gln Asn Glu Leu Asp Glu Glu Ala Ala Lys Thr Leu Leu Ala Asn
                325                 330                 335

Gly Cys Tyr Val Val Ala Glu Gly Ala Asn Met Pro Ser Thr Leu Gly
            340                 345                 350

Ala Val Glu Gln Phe Ile Lys Ala Gly Ile Leu Tyr Ala Pro Gly Lys
        355                 360                 365

Ala Ser Asn Ala Gly Gly Val Ala Thr Ser Gly Leu Glu Met Ser Gln
    370                 375                 380

Asn Ala Ile Arg Leu Ser Trp Thr Arg Glu Glu Val Asp Gln Arg Leu
385                 390                 395                 400

Phe Gly Ile Met Gln Ser Ile His Glu Ser Cys Leu Lys Tyr Gly Lys
                405                 410                 415

Val Gly Asp Thr Val Asn Tyr Val Asn Gly Ala Asn Ile Ala Gly Phe
            420                 425                 430

Val Lys Val Ala Asp Ala Met Leu Ala Gln Gly Phe
        435                 440
```

```
<210> SEQ ID NO 44
<211> LENGTH: 1561
<212> TYPE: PRT
<213> ORGANISM: Neisseria meningitidis (group B)

<400> SEQUENCE: 44

Met Lys Thr Lys Arg Phe Lys Ile Asn Ala Ile Ser Leu Ser Ile Phe
```

-continued

```
1               5                   10                  15

Leu Ala Tyr Ala Leu Thr Pro Tyr Ser Glu Ala Ala Leu Val Arg Asp
            20                  25                  30

Asp Val Asp Tyr Gln Ile Phe Arg Asp Phe Ala Glu Asn Lys Gly Lys
        35                  40                  45

Phe Phe Val Gly Ala Thr Asp Leu Ser Val Lys Asn Lys Gln Gly Gln
    50                  55                  60

Asn Ile Gly Asn Ala Leu Ser Asn Val Pro Met Ile Asp Phe Ser Val
65                  70                  75                  80

Ala Asp Val Asn Lys Arg Ile Ala Thr Val Val Asp Pro Gln Tyr Ala
                85                  90                  95

Val Ser Val Lys His Ala Lys Ala Glu Val His Thr Phe Tyr Tyr Gly
            100                 105                 110

Gln Tyr Asn Gly His Asn Asp Val Ala Asp Lys Glu Asn Glu Tyr Arg
        115                 120                 125

Val Val Glu Gln Asn Asn Tyr Glu Pro His Lys Ala Trp Ser Ala Ser
    130                 135                 140

Asn Leu Gly Arg Leu Glu Asp Tyr Asn Met Ala Arg Phe Asn Lys Phe
145                 150                 155                 160

Val Thr Glu Val Ala Pro Ile Ala Pro Thr Asp Ala Gly Gly Gly Leu
                165                 170                 175

Asp Thr Tyr Lys Asp Lys Asn Arg Phe Ser Ser Phe Val Arg Val Gly
            180                 185                 190

Ala Gly Arg Gln Leu Val Tyr Glu Lys Gly Ala Tyr His Gln Glu Gly
        195                 200                 205

Asn Glu Lys Gly Tyr Asp Leu Arg Asp Leu Ser Gln Ala Tyr Arg Tyr
    210                 215                 220

Ala Ile Ala Gly Thr Pro Tyr Lys Asp Ile Asn Ile Asp Gln Thr Met
225                 230                 235                 240

Asn Thr Glu Gly Leu Ile Gly Phe Gly Asn His Asn Thr His Tyr Ser
                245                 250                 255

Ala Glu Glu Leu Lys Gln Ala Leu Ser Gln Asp Ala Leu Thr Asn Tyr
            260                 265                 270

Gly Val Leu Gly Asp Ser Gly Ser Pro Leu Phe Ala Phe Asp Lys Gln
        275                 280                 285

Lys Asn Gln Trp Val Phe Leu Gly Thr Tyr Asp Tyr Trp Ala Gly Tyr
    290                 295                 300

Gly Lys Lys Ser Trp Gln Glu Trp Asn Ile Tyr Lys Lys Glu Phe Ala
305                 310                 315                 320

Asp Lys Ile Lys Gln Arg Asp Asn Ala Gly Thr Ile Lys Gly Tyr Gly
                325                 330                 335

Glu His His Trp Lys Thr Thr Gly Thr Asn Ser His Ile Gly Ser Thr
            340                 345                 350

Ala Val Arg Leu Ala Asn Asn Glu Arg Asp Ala Asn Asn Gly Gln Asn
        355                 360                 365

Val Thr Phe Glu Asn Asn Gly Thr Leu Val Leu Asp Gln Asn Ile Asn
    370                 375                 380

Gln Gly Ala Gly Gly Leu Phe Phe Lys Gly Asp Tyr Thr Val Lys Gly
385                 390                 395                 400

Ala Asn Asn Asp Ile Thr Trp Leu Gly Ala Gly Ile Asp Val Ala Asp
                405                 410                 415

Gly Lys Lys Val Val Trp Gln Val Lys Asn Pro Asn Gly Asp Arg Leu
            420                 425                 430
```

-continued

```
Ala Lys Ile Gly Lys Gly Thr Leu Glu Ile Asn Gly Thr Gly Val Asn
        435                 440                 445

Gln Gly Glu Leu Lys Val Gly Asp Gly Thr Val Ile Leu Asn Gln Lys
    450                 455                 460

Ala Asp Ser Asn Gln Lys Val Ser Ala Phe Ser Gln Val Gly Ile Val
465                 470                 475                 480

Ser Gly Arg Gly Thr Leu Val Leu Asn Ser Ser Asn Gln Ile Asn Pro
                485                 490                 495

Asp Asn Leu Tyr Phe Gly Phe Arg Gly Gly Arg Leu Asp Ala Asn Gly
            500                 505                 510

Asn Asp Leu Thr Phe Glu His Ile Arg Asn Val Asp Glu Gly Ala Arg
        515                 520                 525

Ile Val Asn His Asn Thr Ser His Ala Ser Thr Ile Thr Leu Thr Gly
    530                 535                 540

Lys Ser Leu Ile Thr Asn Pro Asn Ser Leu Ser Val His Ser Ile Gln
545                 550                 555                 560

Asn Asp Tyr Asp Glu Asp Asp Tyr Ser Tyr Tyr Tyr Arg Pro Arg Arg
                565                 570                 575

Pro Ile Pro Gln Gly Lys Asp Leu Tyr Tyr Lys Asn Tyr Arg Tyr Tyr
            580                 585                 590

Ala Leu Lys Ser Gly Gly Ser Val Asn Ala Pro Met Pro Glu Asn Gly
        595                 600                 605

Gln Thr Glu Asn Asn Asp Trp Ile Leu Met Gly Ser Thr Gln Glu Glu
    610                 615                 620

Ala Lys Lys Asn Ala Met Asn His Lys Asn Asn Gln Arg Ile Ser Gly
625                 630                 635                 640

Phe Ser Gly Phe Phe Gly Glu Glu Asn Gly Lys Gly His Asn Gly Ala
                645                 650                 655

Leu Asn Leu Asn Phe Asn Gly Lys Ser Ala Gln Asn Arg Phe Leu Leu
            660                 665                 670

Thr Gly Gly Thr Asn Leu Asn Gly Lys Ile Ser Val Thr Gln Gly Asn
        675                 680                 685

Val Leu Leu Ser Gly Arg Pro Thr Pro His Ala Arg Asp Phe Val Asn
    690                 695                 700

Lys Ser Ser Ala Arg Lys Asp Ala Arg Phe Ser Lys Asn Asn Glu Val
705                 710                 715                 720

Val Phe Glu Asp Asp Trp Ile Asn Arg Thr Phe Lys Ala Ala Glu Ile
                725                 730                 735

Ala Val Asn Gln Ser Ala Ser Phe Ser Ser Gly Arg Asn Val Ser Asn
            740                 745                 750

Ile Thr Ala Asn Ile Thr Ala Thr Asp Asn Ala Lys Val Asn Leu Gly
        755                 760                 765

Tyr Lys Asn Gly Asp Glu Val Cys Val Arg Ser Asp Tyr Thr Gly Tyr
    770                 775                 780

Val Thr Cys Asn Thr Asp Asn Leu Ser Asp Lys Ala Leu Asn Ser Phe
785                 790                 795                 800

Asp Ala Thr Gln Ile Asn Gly Asn Val Asn Leu Asn Gln Asn Ala Ala
                805                 810                 815

Leu Val Leu Gly Lys Ala Ala Leu Trp Gly Gln Ile Gln Gly Gln Gly
            820                 825                 830

Asn Ser Ser Val Ser Leu Asn Gln His Ser Lys Trp His Leu Thr Ser
        835                 840                 845
```

-continued

```
Asp Ser Gln Val His Asn Leu Ser Leu Ala Asp Ser His Ile His Leu
    850                 855                 860

Asn Asn Ala Ser Asp Ala Gln Ser Ala Asn Lys Tyr His Thr Leu Lys
865                 870                 875                 880

Ile Asn His Leu Ser Gly Asn Gly His Phe His Tyr Leu Thr His Leu
                885                 890                 895

Ala Lys Asn Leu Gly Asp Lys Val Leu Val Lys Glu Ser Ala Ser Gly
            900                 905                 910

His Tyr Gln Leu His Val Gln Asp Lys Thr Gly Glu Pro Asn Gln Glu
        915                 920                 925

Gly Leu Asn Leu Phe Asp Ala Ser Ser Val Gln Asp Arg Ser Arg Leu
    930                 935                 940

Ser Val Ser Leu Ala Asn Asn His Val Asp Leu Gly Ala Leu Arg Tyr
945                 950                 955                 960

Thr Ile Lys Thr Glu Asn Gly Ile Thr Arg Leu Tyr Asn Pro Tyr Ala
                965                 970                 975

Glu Asn Arg Arg Arg Val Lys Pro Ala Pro Ser Pro Ala Thr Asn Thr
            980                 985                 990

Ala Ser Gln Ala Gln Thr Asp Ser Ala Gln Ile Ala Lys Pro Gln Asn
        995                 1000                1005

Ile Val Val Ala Pro Pro Ser Pro Gln Ala Asn Gln Ala Glu Glu Ala
    1010                1015                1020

Lys Arg Gln Gln Ala Lys Ala Glu Gln Val Lys Arg Gln Gln Ala Glu
1025                1030                1035                1040

Ala Glu Lys Val Ala His Gln Lys Ala Glu Glu Ala Lys Arg Gln Gln
                1045                1050                1055

Asp Ala Leu Ala Arg Gln Gln Ala Glu Gln Glu Arg Gln Arg Leu Glu
            1060                1065                1070

Ala Glu Arg Gln Ala Ala Glu Ile Ala Lys Gln Lys Ala Glu Ala Glu
        1075                1080                1085

Glu Ala Lys Arg Arg Ala Ala Glu Ile Ala Glu Gln Lys Ala Ala Ala
    1090                1095                1100

Glu Glu Ala Lys Arg Gln Ala Ala Glu Leu Ala Arg Gln Gln Glu Glu
1105                1110                1115                1120

Ala Arg Lys Ala Ala Glu Leu Ala Ala Lys Gln Lys Ala Glu Thr Glu
                1125                1130                1135

Arg Lys Ala Ala Glu Ile Ala Glu Gln Lys Ala Glu Ala Glu Arg Glu
            1140                1145                1150

Ala Ala Glu Leu Ala Lys Gln Lys Ala Glu Glu Glu Gly Arg Gln Ala
        1155                1160                1165

Ala Gln Ser Gln Pro Lys Arg Arg Asn Arg Arg Ala Ile Pro Pro Glu
    1170                1175                1180

Leu Ser Ser Asp Ala Thr Thr Arg Ala Leu Pro Arg Ile Ala Arg Asn
1185                1190                1195                1200

Ser Asn Pro Asp Ala Ser Asp Tyr Glu Glu Ile Pro Leu Asp Ala Leu
                1205                1210                1215

Glu Asp Glu Asp Val Ser Glu Ser Val Asp Thr Ser Asp Lys Gln Pro
            1220                1225                1230

Gln Asp Asn Thr Glu Leu His Glu Lys Val Glu Thr Val Ser Leu Gln
        1235                1240                1245

Pro Arg Ala Ala Gln Pro Arg Ala Gln Ala Ala Ala Gln Pro Gln Ala
    1250                1255                1260

Gln Ala Val Ala Gln Ala Asp Ala Val Ser Thr Asn Thr Asn Ser Ala
```

-continued

```
1265                1270                1275                1280

Leu Ser Asp Ala Met Ala Ser Thr Gln Ser Ile Leu Leu Asp Thr Gly
                1285                1290                1295

Ala Ser Leu Thr Arg His Ile Ala Gln Lys Ser Arg Ala Asp Ala Glu
            1300                1305                1310

Lys Asn Ser Val Trp Met Ser Asn Ile Gly Tyr Gly Arg Asp Tyr Ala
        1315                1320                1325

Ser Ala Gln Tyr Arg Arg Phe Ser Ser Lys Arg Thr Gln Thr Gln Ile
    1330                1335                1340

Gly Ile Asp Arg Ser Leu Ser Glu Asn Met Gln Ile Gly Gly Val Leu
1345                1350                1355                1360

Thr Tyr Ser Asp Ser Gln His Thr Phe Asp Gln Ala Ser Gly Lys Asn
                1365                1370                1375

Thr Phe Val Gln Ala Asn Leu Tyr Gly Lys Tyr Tyr Leu Asn Asp Ala
            1380                1385                1390

Trp Tyr Val Ala Gly Asp Ile Gly Ala Gly Ser Leu Arg Ser Arg Leu
        1395                1400                1405

Gln Thr Gln Gln Lys Ala Asn Phe Asn Arg Thr Ser Ile Gln Thr Gly
    1410                1415                1420

Leu Thr Leu Gly Asn Thr Leu Lys Ile Asn Gln Phe Glu Ile Val Pro
1425                1430                1435                1440

Ser Ala Gly Ile Arg Tyr Ser Arg Leu Ser Ser Ala Asp Tyr Lys Leu
                1445                1450                1455

Gly Asn Asp Ser Val Lys Val Ser Ser Met Ser Val Lys Thr Leu Thr
            1460                1465                1470

Ala Gly Leu Asp Phe Ala Tyr Arg Phe Lys Val Gly Asn Leu Thr Val
        1475                1480                1485

Lys Pro Leu Leu Ser Ala Ala Tyr Phe Ala Asn Tyr Gly Lys Gly Gly
    1490                1495                1500

Val Asn Val Gly Gly Asn Ser Phe Ala Tyr Lys Ala Asp Asn Gln Gln
1505                1510                1515                1520

Gln Tyr Ser Ala Gly Ala Ala Leu Leu Tyr Arg Asn Val Thr Leu Asn
                1525                1530                1535

Val Asn Gly Ser Ile Thr Lys Gly Lys Gln Leu Glu Lys Gln Lys Ser
            1540                1545                1550

Gly Gln Ile Lys Ile Gln Ile Arg Phe
        1555                1560


<210> SEQ ID NO 45
<211> LENGTH: 242
<212> TYPE: PRT
<213> ORGANISM: Neisseria meningitidis (group B)

<400> SEQUENCE: 45

Met Ser Gln Ile Thr Met Arg Gln Met Ile Glu Ala Gly Val His Phe
  1               5                  10                  15

Gly His Gln Thr Arg Phe Trp Asn Pro Lys Met Ala Gln Tyr Ile Phe
            20                  25                  30

Gly Ala Arg Asn Lys Ile His Ile Val Asn Leu Glu Lys Thr Leu Pro
        35                  40                  45

Met Phe Gln Asp Ala Gln Glu Ala Val Arg Arg Leu Val Ala Asn Lys
     50                  55                  60

Gly Thr Val Leu Phe Val Gly Thr Lys Arg Gln Ala Arg Asp Ile Ile
 65                  70                  75                  80
```

-continued

```
Arg Glu Glu Ala Thr Arg Ala Gly Met Pro Phe Val Asp Tyr Arg Trp
                 85                  90                  95

Leu Gly Gly Met Leu Thr Asn Tyr Lys Thr Val Lys Gln Ser Ile Lys
            100                 105                 110

Arg Leu Glu Glu Lys Thr Ala Ala Leu Glu Asn Ala Ala Glu Ser Gly
        115                 120                 125

Phe Ser Lys Lys Glu Ile Leu Glu Met Gln Arg Asp Val Glu Lys Leu
    130                 135                 140

Glu Arg Ser Leu Gly Gly Ile Lys Asn Met Lys Gly Leu Pro Asp Ala
145                 150                 155                 160

Ile Phe Val Ile Asp Thr Gly Tyr Gln Lys Gly Thr Leu Val Glu Ala
                165                 170                 175

Glu Lys Leu Gly Ile Pro Val Ile Ala Val Val Asp Thr Asn Asn Ser
            180                 185                 190

Pro Asp Gly Val Lys Tyr Val Ile Pro Gly Asn Asp Asp Ser Ala Lys
        195                 200                 205

Ala Ile Arg Leu Tyr Cys Arg Gly Ile Ala Asp Ala Val Leu Glu Gly
    210                 215                 220

Lys Asn Gln Ala Leu Gln Glu Thr Val Ala Ala Ala Gln Glu Ala Ala
225                 230                 235                 240

Ala Glu


<210> SEQ ID NO 46
<211> LENGTH: 230
<212> TYPE: PRT
<213> ORGANISM: Neisseria meningitidis (group B)

<400> SEQUENCE: 46

Met Gly Gln Lys Ile Asn Pro Thr Gly Phe Arg Leu Ala Val Thr Lys
  1               5                  10                  15

Asp Trp Ala Ser Lys Trp Phe Ala Lys Ser Thr Asp Phe Ser Thr Val
             20                  25                  30

Leu Lys Gln Asp Ile Asp Val Arg Asn Tyr Leu Arg Gln Lys Leu Ala
         35                  40                  45

Asn Ala Ser Val Gly Arg Val Val Ile Glu Arg Pro Ala Lys Ser Ala
     50                  55                  60

Arg Ile Thr Ile His Ser Ala Arg Pro Gly Val Val Ile Gly Lys Lys
 65                  70                  75                  80

Gly Glu Asp Ile Glu Val Leu Lys Arg Asp Leu Gln Val Leu Met Gly
                 85                  90                  95

Val Pro Val His Val Asn Ile Glu Glu Ile Arg Arg Pro Glu Leu Asp
            100                 105                 110

Ala Gln Ile Ile Ala Asp Gly Ile Ala Gln Gln Leu Glu Lys Arg Val
        115                 120                 125

Gln Phe Arg Arg Ala Met Lys Arg Ala Met Gln Asn Ala Met Arg Ser
    130                 135                 140

Gly Ala Lys Gly Ile Lys Ile Met Thr Ser Gly Arg Leu Asn Gly Ala
145                 150                 155                 160

Asp Ile Ala Arg Ser Glu Trp Tyr Arg Glu Gly Arg Val Pro Leu His
                165                 170                 175

Thr Leu Arg Ala Asn Val Asp Tyr Ala Thr Ser Glu Ala His Thr Thr
            180                 185                 190

Tyr Gly Val Leu Gly Leu Lys Val Trp Val Tyr Thr Glu Gly Asn Ile
        195                 200                 205
```

```
Lys Ser Ser Lys Pro Glu His Glu Ser Lys Gln Arg Lys Ala Gly Arg
    210                 215                 220

Arg Asn Ala Ala Ala Asn
225                 230


<210> SEQ ID NO 47
<211> LENGTH: 172
<212> TYPE: PRT
<213> ORGANISM: Neisseria meningitidis (group B)

<400> SEQUENCE: 47

Met Ala Lys His Glu Ile Glu Glu Arg Gly Asp Gly Leu Ile Glu Lys
  1               5                  10                  15

Met Val Ala Val Asn Arg Val Thr Lys Val Val Lys Gly Gly Arg Ile
             20                  25                  30

Met Ala Phe Ser Ala Leu Thr Val Val Gly Asp Gly Asp Gly Arg Ile
         35                  40                  45

Gly Met Gly Lys Gly Lys Ser Lys Glu Val Pro Val Ala Val Gln Lys
     50                  55                  60

Ala Met Asp Gln Ala Arg Arg Ser Met Ile Lys Val Pro Leu Lys Asn
 65                  70                  75                  80

Gly Thr Ile His His Glu Val Ile Gly Arg His Gly Ala Thr Lys Val
                 85                  90                  95

Phe Met Gln Pro Ala Lys Glu Gly Ser Gly Val Lys Ala Gly Gly Pro
            100                 105                 110

Met Arg Leu Val Phe Asp Ala Met Gly Ile His Asn Ile Ser Ala Lys
        115                 120                 125

Val His Gly Ser Thr Asn Pro Tyr Asn Ile Val Arg Ala Thr Leu Asp
    130                 135                 140

Gly Leu Ser Lys Leu His Thr Pro Ala Asp Ile Ala Ala Lys Arg Gly
145                 150                 155                 160

Leu Thr Val Glu Asp Ile Leu Gly Val Asn His Gly
                165                 170


<210> SEQ ID NO 48
<211> LENGTH: 103
<212> TYPE: PRT
<213> ORGANISM: Neisseria meningitidis (group B)

<400> SEQUENCE: 48

Met Ala Asn Gln Lys Ile Arg Ile Arg Leu Lys Ala Tyr Asp Tyr Ala
  1               5                  10                  15

Leu Ile Asp Arg Ser Ala Gln Glu Ile Val Glu Thr Ala Lys Arg Thr
             20                  25                  30

Gly Ala Val Val Lys Gly Pro Ile Pro Leu Pro Thr Lys Ile Glu Arg
         35                  40                  45

Phe Asn Ile Leu Arg Ser Pro His Val Asn Lys Thr Ser Arg Glu Gln
     50                  55                  60

Leu Glu Ile Arg Thr His Leu Arg Leu Met Asp Ile Val Asp Trp Thr
 65                  70                  75                  80

Asp Lys Thr Thr Asp Ala Leu Met Lys Leu Asp Leu Pro Ala Gly Val
                 85                  90                  95

Asp Val Glu Ile Lys Val Gln
            100


<210> SEQ ID NO 49
<211> LENGTH: 131
```

```
<212> TYPE: PRT
<213> ORGANISM: Neisseria meningitidis (group B)

<400> SEQUENCE: 49

Met Ala Lys Ala Asn Thr Ala Ser Arg Val Arg Lys Lys Val Arg Lys
  1               5                  10                  15

Thr Val Ser Glu Gly Ile Val His Val His Ala Ser Phe Asn Asn Thr
             20                  25                  30

Ile Ile Thr Ile Thr Asp Arg Gln Gly Asn Ala Leu Ser Trp Ala Thr
         35                  40                  45

Ser Gly Gly Ala Gly Phe Lys Gly Ser Arg Lys Ser Thr Pro Phe Ala
     50                  55                  60

Ala Gln Val Ala Ala Glu Ala Ala Gly Lys Val Ala Gln Glu Tyr Gly
 65                  70                  75                  80

Val Lys Asn Leu Glu Val Arg Ile Lys Gly Pro Gly Pro Gly Arg Glu
                 85                  90                  95

Ser Ser Val Arg Ala Leu Asn Ala Leu Gly Phe Lys Ile Thr Ser Ile
            100                 105                 110

Thr Asp Val Thr Pro Leu Pro His Asn Gly Cys Arg Pro Pro Lys Lys
        115                 120                 125

Arg Arg Ile
    130


<210> SEQ ID NO 50
<211> LENGTH: 87
<212> TYPE: PRT
<213> ORGANISM: Neisseria meningitidis (group B)

<400> SEQUENCE: 50

Met Ser Glu Thr Lys Asn Val Arg Thr Leu Gln Gly Lys Val Val Ser
  1               5                  10                  15

Asp Lys Met Asp Lys Thr Val Thr Val Leu Val Glu Arg Lys Val Lys
             20                  25                  30

His Pro Leu Tyr Gly Lys Ile Ile Arg Leu Ser Thr Lys Ile His Ala
         35                  40                  45

His Asp Glu Asn Asn Gln Tyr Gly Ile Gly Asp Val Val Val Ile Ser
     50                  55                  60

Glu Ser Arg Pro Leu Ser Lys Thr Lys Ser Trp Val Val Ser Glu Leu
 65                  70                  75                  80

Val Glu Lys Ala Arg Ser Ile
                 85


<210> SEQ ID NO 51
<211> LENGTH: 122
<212> TYPE: PRT
<213> ORGANISM: Neisseria meningitidis (group B)

<400> SEQUENCE: 51

Met Ile Gln Met Gln Thr Ile Leu Asp Val Ala Asp Asn Ser Gly Ala
  1               5                  10                  15

Arg Arg Val Met Cys Ile Lys Val Leu Gly Gly Ser Lys Arg Arg Tyr
             20                  25                  30

Ala Ser Val Gly Asp Ile Ile Lys Val Ala Val Lys Asp Ala Ala Pro
         35                  40                  45

Arg Gly Arg Val Lys Lys Gly Asp Val Tyr Asn Ala Val Val Val Arg
     50                  55                  60

Thr Ala Lys Gly Val Arg Arg Pro Asp Gly Ala Leu Ile Lys Phe Asp
```

```
 65                  70                  75                  80

Asn Asn Ala Ala Val Leu Leu Asn Asn Lys Leu Glu Pro Leu Gly Thr
                 85                  90                  95

Arg Ile Phe Gly Pro Val Thr Arg Glu Leu Arg Thr Glu Arg Phe Met
            100                 105                 110

Lys Ile Val Ser Leu Ala Pro Glu Val Leu
        115                 120


<210> SEQ ID NO 52
<211> LENGTH: 231
<212> TYPE: PRT
<213> ORGANISM: Neisseria meningitidis (group B)

<400> SEQUENCE: 52

Met Ala Lys Val Ser Lys Arg Leu Lys Ala Leu Arg Ser Ser Val Glu
  1               5                  10                  15

Ala Asn Lys Leu Tyr Ala Ile Asp Glu Ala Ile Ala Leu Val Lys Lys
             20                  25                  30

Ala Ala Thr Ala Lys Phe Asp Glu Ser Val Asp Val Ser Phe Asn Leu
         35                  40                  45

Gly Val Asp Pro Arg Lys Ser Asp Gln Val Ile Arg Gly Ser Val Val
     50                  55                  60

Leu Pro Lys Gly Thr Gly Lys Ile Thr Arg Val Ala Val Phe Thr Gln
 65                  70                  75                  80

Gly Ala Asn Ala Glu Ala Ala Lys Glu Ala Gly Ala Asp Ile Val Gly
                 85                  90                  95

Phe Glu Asp Leu Ala Ala Glu Ile Lys Ala Gly Asn Leu Asn Phe Asp
            100                 105                 110

Val Val Ile Ala Ser Pro Asp Ala Met Arg Ile Val Gly Gln Leu Gly
        115                 120                 125

Thr Ile Leu Gly Pro Arg Gly Leu Met Pro Asn Pro Lys Val Gly Thr
    130                 135                 140

Val Thr Pro Asn Val Ala Glu Ala Val Lys Asn Ala Lys Ala Gly Gln
145                 150                 155                 160

Val Gln Tyr Arg Thr Asp Lys Ala Gly Ile Val His Ala Thr Ile Gly
                165                 170                 175

Arg Ala Ser Phe Ala Glu Ala Asp Leu Lys Glu Asn Phe Asp Ala Leu
            180                 185                 190

Leu Asp Ala Ile Val Lys Ala Lys Pro Ala Ala Ala Lys Gly Gln Tyr
        195                 200                 205

Leu Lys Lys Val Ala Val Ser Ser Thr Met Gly Leu Gly Ile Arg Val
    210                 215                 220

Asp Thr Ser Ser Val Asn Asn
225                 230


<210> SEQ ID NO 53
<211> LENGTH: 177
<212> TYPE: PRT
<213> ORGANISM: Neisseria meningitidis (group B)

<400> SEQUENCE: 53

Met Ser Arg Val Ala Lys Asn Pro Val Thr Val Pro Ala Gly Val Glu
  1               5                  10                  15

Val Lys Phe Gly Ala Glu Ala Leu Val Ile Lys Gly Lys Asn Gly Glu
             20                  25                  30

Leu Ser Phe Pro Leu His Ser Asp Val Ala Ile Glu Phe Asn Asp Gly
```

```
        35                  40                  45

Lys Leu Thr Phe Val Ala Asn Asn Ser Ser Lys Gln Ala Asn Ala Met
    50                  55                  60

Ser Gly Thr Ala Arg Ala Leu Val Ser Asn Met Val Lys Gly Val Ser
65                  70                  75                  80

Glu Gly Phe Glu Lys Arg Leu Gln Leu Ile Gly Val Gly Tyr Arg Ala
                85                  90                  95

Gln Ala Gln Gly Lys Ile Leu Asn Leu Ser Leu Gly Phe Ser His Pro
            100                 105                 110

Ile Val Tyr Glu Met Pro Glu Gly Val Ser Val Gln Thr Pro Ser Gln
        115                 120                 125

Thr Glu Ile Val Leu Thr Gly Ser Asp Lys Gln Val Val Gly Gln Val
    130                 135                 140

Ala Ala Glu Ile Arg Ala Phe Arg Ala Pro Glu Pro Tyr Lys Gly Lys
145                 150                 155                 160

Gly Val Arg Tyr Val Gly Glu Val Val Val Met Lys Glu Ala Lys Lys
                165                 170                 175

Lys


<210> SEQ ID NO 54
<211> LENGTH: 138
<212> TYPE: PRT
<213> ORGANISM: Neisseria meningitidis (group B)

<400> SEQUENCE: 54

Met Leu Gln Pro Thr Arg Leu Lys Tyr Arg Lys Gln Gln Lys Gly Arg
  1               5                  10                  15

Asn Thr Gly Ile Ala Thr Arg Gly Asn Lys Val Ser Phe Gly Glu Phe
            20                  25                  30

Gly Leu Lys Ala Val Gly Arg Gly Arg Leu Thr Ala Arg Gln Ile Glu
        35                  40                  45

Ala Ala Arg Arg Ala Met Thr Arg His Ile Lys Arg Gly Gly Arg Ile
    50                  55                  60

Trp Ile Arg Val Phe Pro Asp Lys Pro Ile Thr Glu Lys Pro Ile Gln
65                  70                  75                  80

Val Arg Met Gly Gly Gly Lys Gly Asn Val Glu Tyr Tyr Ile Ala Glu
                85                  90                  95

Ile Lys Pro Gly Lys Val Leu Tyr Glu Met Asp Gly Val Pro Glu Glu
            100                 105                 110

Leu Ala Arg Glu Ala Phe Glu Leu Ala Ala Ala Lys Leu Pro Ile Pro
        115                 120                 125

Thr Thr Phe Val Val Arg Gln Val Gly Gln
    130                 135


<210> SEQ ID NO 55
<211> LENGTH: 190
<212> TYPE: PRT
<213> ORGANISM: Neisseria meningitidis (group B)

<400> SEQUENCE: 55

Met Thr Tyr Glu Ile Gln Ala Ser Val Arg Glu Ala Gln Gly Thr Gly
  1               5                  10                  15

Ala Ser Arg Arg Leu Arg Arg Glu Gly Gln Ile Pro Gly Ile Leu Tyr
            20                  25                  30

Gly Glu Gly Gln Glu Pro Val Ala Ile Ala Val Asp His Lys Thr Val
        35                  40                  45
```

```
Phe Tyr Ala Leu Glu Lys Glu Ser Phe His Thr Ala Leu Ile Lys Leu
     50                  55                  60

Ser Leu Asn Gly Glu Thr Lys Asp Val Ile Val Arg Asp Phe Gln Met
 65                  70                  75                  80

His Pro Phe Arg Arg Glu Val Gln His Ile Asp Phe Gln Ala Val Lys
                 85                  90                  95

Ala Asp Gln Leu Val Arg Ile Arg Val Pro Leu His Ile Val Asn Ala
            100                 105                 110

Glu Asn Ser Gln Ala Val Lys Leu Gln Gly Gly Arg Val Ser Leu Leu
        115                 120                 125

Asn Thr Ser Val Glu Val Val Ala Leu Pro Ala Asn Ile Pro Ala Phe
    130                 135                 140

Leu Asp Leu Asp Cys Ala Glu Val Val Ala Gly Asp Ile Leu His Leu
145                 150                 155                 160

Ser Asp Ile Lys Leu Pro Glu Gly Val Glu Ser Val Ser Leu Lys Arg
                165                 170                 175

Asn Glu Asn Leu Ala Val Ala Thr Val Thr Gly Lys Lys Arg
            180                 185                 190


<210> SEQ ID NO 56
<211> LENGTH: 144
<212> TYPE: PRT
<213> ORGANISM: Neisseria meningitidis (group B)

<400> SEQUENCE: 56

Met Phe Leu Asn Thr Ile Gln Pro Ala Val Gly Ala Thr His Ala Gly
  1               5                  10                  15

Arg Arg Val Gly Arg Gly Ile Gly Ser Gly Leu Gly Lys Thr Gly Gly
             20                  25                  30

Arg Gly His Lys Gly Gln Lys Ser Arg Ser Gly Gly Phe His Lys Val
         35                  40                  45

Gly Phe Glu Gly Gly Gln Met Pro Leu Gln Arg Arg Leu Pro Lys Arg
     50                  55                  60

Gly Phe Lys Ser Leu Thr Ala Ser Ala Asn Ala Gln Leu Arg Leu Ser
 65                  70                  75                  80

Glu Leu Glu Ser Ile Ala Val Asn Glu Ile Asp Ile Leu Val Leu Lys
                 85                  90                  95

Gln Ala Gly Leu Ile Ala Ser Thr Val Ser Asn Val Lys Val Ile Ala
            100                 105                 110

Ser Gly Glu Ile Ser Lys Ala Val Ala Leu Lys Gly Ile Lys Val Thr
        115                 120                 125

Lys Gly Ala Arg Ala Ala Ile Glu Ala Val Gly Gly Lys Ile Glu Met
    130                 135                 140


<210> SEQ ID NO 57
<211> LENGTH: 109
<212> TYPE: PRT
<213> ORGANISM: Neisseria meningitidis (group B)

<400> SEQUENCE: 57

Met Arg Val Asn Ala Gln His Lys Asn Ala Arg Ile Ser Ala Gln Lys
  1               5                  10                  15

Ala Arg Leu Val Ala Asp Leu Ile Arg Gly Lys Asp Val Ala Gln Ala
             20                  25                  30

Leu Asn Ile Leu Ala Phe Ser Pro Lys Lys Gly Ala Glu Leu Ile Lys
         35                  40                  45
```

```
Lys Val Leu Glu Ser Ala Ile Ala Asn Ala Glu His Asn Asn Gly Ala
     50                  55                  60

Asp Ile Asp Glu Leu Lys Val Val Thr Ile Phe Val Asp Lys Gly Pro
 65                  70                  75                  80

Ser Leu Lys Arg Phe Gln Ala Arg Ala Lys Gly Arg Gly Asn Arg Ile
                 85                  90                  95

Glu Lys Gln Thr Cys His Ile Asn Val Thr Val Gly Asn
            100                 105


<210> SEQ ID NO 58
<211> LENGTH: 150
<212> TYPE: PRT
<213> ORGANISM: Neisseria meningitidis (group B)

<400> SEQUENCE: 58

Met Gln Ile Ile Leu Leu Glu Lys Ile Gly Gly Leu Gly Asn Leu Gly
  1               5                  10                  15

Asp Ile Val Thr Val Lys Asn Gly Tyr Ala Arg Asn Phe Leu Ile Pro
             20                  25                  30

Ala Gly Lys Ala Lys Arg Ala Thr Glu Ala Asn Met Lys Glu Phe Glu
         35                  40                  45

Ala Arg Arg Ala Glu Leu Glu Ala Lys Gln Ala Glu Ile Leu Ala Asp
     50                  55                  60

Ala Arg Val Arg Gln Glu Lys Leu Asp Gly Gln Thr Val Thr Val Ala
 65                  70                  75                  80

Gln Lys Ala Gly Val Asp Gly Arg Leu Phe Gly Ser Val Thr Asn Ala
                 85                  90                  95

Asp Ile Ala Ala Ala Ile Val Ala Ala Gly Ile Glu Ala Val Lys Ala
            100                 105                 110

Asn Val Arg Leu Pro Asn Gly Pro Leu Lys Ala Val Gly Glu Tyr Glu
        115                 120                 125

Val Glu Val Ala Leu His Thr Asp Ala Val Ala Lys Ile Thr Val Ala
    130                 135                 140

Val Val Ala Ala Thr Glu
145                 150


<210> SEQ ID NO 59
<211> LENGTH: 144
<212> TYPE: PRT
<213> ORGANISM: Neisseria meningitidis (group B)

<400> SEQUENCE: 59

Met Ala Lys Lys Ile Ile Gly Tyr Ile Lys Leu Gln Ile Pro Ala Gly
  1               5                  10                  15

Lys Ala Asn Pro Ser Pro Pro Val Gly Pro Ala Leu Gly Gln Arg Gly
             20                  25                  30

Leu Asn Ile Met Glu Phe Cys Lys Ala Phe Asn Ala Ala Thr Gln Gly
         35                  40                  45

Met Glu Pro Gly Leu Pro Ile Pro Val Val Ile Thr Ala Phe Ala Asp
     50                  55                  60

Lys Ser Phe Thr Phe Val Met Lys Thr Pro Pro Ala Ser Ile Leu Leu
 65                  70                  75                  80

Lys Lys Ala Ala Gly Leu Gln Lys Gly Ser Ser Asn Pro Leu Thr Asn
                 85                  90                  95

Lys Val Gly Lys Leu Thr Arg Ala Gln Leu Glu Glu Ile Ala Lys Thr
            100                 105                 110
```

```
Lys Asp Pro Asp Leu Thr Ala Ala Asp Leu Asp Ala Ala Val Arg Thr
        115                 120                 125

Ile Ala Gly Ser Ala Arg Ser Met Gly Leu Asp Val Glu Gly Val Val
    130                 135                 140


<210> SEQ ID NO 60
<211> LENGTH: 153
<212> TYPE: PRT
<213> ORGANISM: Horse

<400> SEQUENCE: 60

Gly Leu Ser Asp Gly Glu Trp Gln Gln Val Leu Asn Val Trp Gly Lys
  1               5                  10                  15

Val Glu Ala Asp Ile Ala Gly His Gly Gln Glu Val Leu Ile Arg Leu
             20                  25                  30

Phe Thr Gly His Pro Glu Thr Leu Glu Lys Phe Asp Lys Phe Lys His
         35                  40                  45

Leu Lys Thr Glu Ala Glu Met Lys Ala Ser Glu Asp Leu Lys Lys His
     50                  55                  60

Gly Thr Val Val Leu Thr Ala Leu Gly Gly Ile Leu Lys Lys Lys Gly
 65                  70                  75                  80

His His Glu Ala Glu Leu Lys Pro Leu Ala Gln Ser His Ala Thr Lys
                 85                  90                  95

His Lys Ile Pro Ile Lys Tyr Leu Glu Phe Ile Ser Asp Ala Ile Ile
            100                 105                 110

His Val Leu His Ser Lys His Pro Gly Asp Phe Gly Ala Asp Ala Gln
        115                 120                 125

Gly Ala Met Thr Lys Ala Leu Glu Leu Phe Arg Asn Asp Ile Ala Ala
    130                 135                 140

Lys Tyr Lys Glu Leu Gly Phe Gln Gly
145                 150


<210> SEQ ID NO 61
<211> LENGTH: 165
<212> TYPE: PRT
<213> ORGANISM: Homo sapiens

<400> SEQUENCE: 61

Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

-continued

```
Ala Glu Ile Met Arg Ser Phe Ser Leu Ser Thr Asn Leu Gln Glu Ser
145                 150                 155                 160

Leu Arg Ser Lys Glu
                165
```

METHOD OF SELECTIVE PEPTIDE ISOLATION FOR THE IDENTIFICATION AND QUANTITATIVE ANALYSIS OF PROTEINS IN COMPLEX MIXTURES

This application asserts priority to Cuban application number CU2003/0269 filed on Nov. 19, 2003. The specification of Cuban application number CU2003/0269 is hereby incorporated by reference in its entirety.

BACKGROUND OF THE INVENTION

The present invention relates to the biotechnology field, in particular with proteomics. Proteomics is defined as a group of tools, techniques and methods very close related to the proteomes studies. The term proteome is used to define the protein complement of the genome.

Nowadays the combination of separation technologies with mass spectrometry and automatic database search has made possible the high-trough put identification of proteins in complex mixtures.

Most of the emerging techniques analyze the peptides generated by hydrolysis of the proteins by the combination of liquid chromatography and mass spectrometry.

In 1999 Link et al. (Link, A. J. et al. Direct analysis of protein complexes using mass spectrometry. Nat. Biotechnol. 17, 676-682, 1999), developed a method based in two dimensional liquid chromatography and mass spectrometry (LC-MS/MS). For this purpose they packed a microcapillary column with ion exchange and reverse phase media. By this way, all proteolytic peptides are initially absorbed by the ion exchanger. Then, a single fraction of peptides is transferred to the reverse phase using a discontinuing salt gradient. Finally, the peptides are directly eluted from the reverse phase to the mass spectrometer using an increased gradient of acetonitrile. The described procedure is repeated several times using increased salts concentration in order to released additional fractions of peptides from the ion exchanger. This method is better known as MudPiT (Multidimensional Protein Identification Technology). Using the MudPiT, Washburn M. P. et al. identified 1484 proteins from the yeast *Saccharomyces cerevisiae* (Washburn M. P. et al. Large-scale analysis of the yeast proteome by multidimensional protein identification technology, *Nature Biotechnology* 19, 242-247, 2001). Although the MudPiT dramatically accelerated the proteins identification procedure, the relative quantitation of proteins could not be easily achieved. In this sense, Washburn M P et al., (Analysis of quantitative proteomic data generated via multidimensional protein identification technology. Analytical Chemistry. 74:1650-1656, 2002), quantified the proteins by the metabolic labeling of two *Saccharomyces cerevisiae* cultures. Cells were grown in enriched nitrogen-14/15 ($^{14}N/^{15}N$) media in a similar way to the previous studies of Oda et. al. (Accurate quantitation of protein expression and site-specific phosphorylation. Proc. Natl. Acad. Sci. USA 96, 6591-6596, 1999). These authors identified the proteins using two dimensional electrophoresis while Washburn M P et al. used MudPiT. For both cases the relative quantitation of proteins was done taking into account the relative intensities of the mass spectrum signals of a given labeled peptide according to the conditions cultures of its original sample.

Due to the high cost of reagents and media needed, the metabolic labeling is mainly applied to organisms such as bacteria and yeast. Moreover, in this kind of labeling all the nitrogen atoms of the proteins are labeled: the nitrogens atoms of the peptide bond as well as those of the amino acids side chains, which make impossible to predict the mass difference of homolog labeled peptides without the knowledge of the amino acid sequence.

An important step was taken by a group of authors using a different kind of metabolic labeling. In this case labeled essential amino acids are introduced to the cells cultures and hence they are incorporated to every expressed protein. This strategy was named SILAC (stable isotope labeling by amino acids in cell culture) and its potentialities have been proved using labeled amino such as leucine (1H/2D) and lysine ($^{12}C/^{13}C$) (S. E. Ong, B. Blagoev, I. Kratchmarova, D. B. Kristensen, H. Steen, A. Pandey, M. Mann, Mol. Cell Proteomics 1, 2002, 376-386); (Berger S J, Lee S W, Anderson G A, Lijiana P T, Tolić N, Shen Y, Zhao R, Smith R D, 2002, High-throughput Global Peptide Proteomic Analysis by Combining Stable Isotope Amino Acid Labeling and Data-Dependent Multiplexed-MS/MS. Analytical Chemistry 74:4994-5000); and (Precise Peptide Sequencing and Protein Quantification in the Human Proteome Through In Vivo Lysine-Specific Mass Tagging, J Am Soc Mass Spectrom 2003, 14, 1-7).

The enzymatic labeling of peptides has also been suggested and employed during the proteolytic digestion of the protein mixtures in the presence of water and oxygen-18 enriched water ($H_2{}^{18}O$). In the latest case, one or two atoms of oxygen-18 are incorporated to the carboxy terminus of generated peptides. The comparative proteomic study is conducted mixing the samples of labeled and non-labeled peptides and analyzing by mass spectrometry, the pairs of homolog peptides. The ratio between the areas of the signals of a given peptide is proportional to the concentration ratio of the corresponding protein in the analyzed samples.

With this labeling technique there is not enough separation between the mass signals to avoid the overlapping of the isotopic envelops. Additionally, the incorporation of one or two $^{18}O$ atoms produces a complex pattern which makes difficult the analysis. In this sense Yao et al. (Yao X, Afonso C, Fenselau C. Dissection of proteolytic $^{18}O$ labeling: endoprotease-catalyzed $^{16}O$-to-$^{18}O$ exchange of truncated peptide substrates. J Proteome Res. 2003, 2,147-52) proposed a procedure to catalyze the complete incorporation of two $^{18}O$ atoms to the C-terminus of peptides.

Besides the additional steps and experimental procedures, these methods are not saved from the possible appearance of other peptide(s) sharing part of the mass range covered by the isotopic envelope.

The inverse labeling methodology proposes a scheme to accentuate and emphasizes those ion signals that reflect the differential expression of proteins, by means of two experiments executed in parallel where each one use an inverse labeled respect to the other. The subtraction of the two mass spectra allows focusing the attention on those mass-changing-signals in one experiment respect to the other. The inverse labeling offers several advantages such as the identification of proteins which extreme expression changes and the detection of post-translational modifications. Furthermore, this methodology significantly reduces the time and efforts dedicated to the analysis of peptides MS/MS as well as protein identification and quantification. However, subtle changes in protein expression may no be detected by visual examination, especially when the differences do not exceed the noise of the mass spectra. In addition, the filtering and/or smoothing of the spectra results in lost of resolution and of relevant information in region of low signal-to-noise ratio. Another disadvantage of the inverse labeling method is the need of two experiments which certainly reduce the sensitivity.

Taking in to account the current resolution power of liquid chromatography and mass spectrometry systems, the analysis of all peptides generated during the hydrolysis of a complex mixture of protein results impracticable. For this reason, other alternatives of quantitative analysis of proteomes have emerged. In the new methods, the identification and quantification of protein is achieved by the selective isolation and analysis of a reduced group of peptides per protein present in the mixture.

An example of the emerging alternatives is the ICAT (isotope-code affinity tags) methodology (Quantitative analysis of complex protein mixtures using isotope-coded affinity tags. Gygi, S. P., Rist, B., Gerber, S. A., Turecek, F., Gelb, M. H., and Aebersold, R. *Nat. Biotechnol.* 17, 994-999, 1999). With ICAT, only cysteine containing peptides are isolated and analyzed through the use of reagent of three functional elements: an specific chemical reactivity, an isotopically coded linker and an affinity tag. In this method the free thiol of cysteines of a protein sample representative of a given cellular stage are modified with a light isotopically version of the ICAT reagent, while the sample representative of a second cellular stage is modified with the heavy version of the ICAT reagent. The two samples are combined, enzymatically digested and the cysteine contained peptides are isolated by affinity chromatography and analyzed by μLC-MS/MS.

The differential protein expression is quantify by measuring the relative intensities of the mass signals of the paired of peptides with identical sequences, but labeled with light and heavy isotopic version of the ICAT reagent.

An algorithm which reconstructs the spectra by means of a smoothing filter is used to determine the ratio of intensities. By this way the location and intensity of the local maxims (peaks) are identified. Finally, the average of the intensities of all identified peptides is determined to each protein.

The following limitations have been ascribed on the ICAT methodology:

- proteins not containing cysteines residues are excluded from the analysis.
- the size of the ICAT reagent causes interferences during the ionization and the mass spectra interpretation.
- peptides labeled with the light and heavy versions of the ICAT reagent ($H_8/D_8$) could eluted significantly separated on RP-HPLC systems, a fact that could mislead the quantification process.
- the quantification process could not be applied to labeling techniques that do not provide enough mass separation to avoid the overlapping of the isotopic distributions.
- the quantification process could not offer reliable results if there is an overlapping of the isotopic distributions of a given peptide with the isotopic distributions of any of the pair (light/heavy) of homolog labeled peptides.

In spite of the limitations described for this method, it continues being necessary to identify and determine relative levels of proteins expressions in complex mixtures, through the selective and specific isolation of a small group of peptide per protein, i.e. the previous simplification of the mixture of proteolytic peptides before the mass spectrometry analysis. The reduction of sample complexity would allow the identification of proteins poorly represented in the mixture, and would avoid the sequencing of many peptides from the same protein. Additionally, it is also necessary the development of methods to analyze and process the spectra of overlapped mass signals without complicating the experimental procedures.

DETAILED DESCRIPTION OF THE INVENTION

When a complex mixture of proteins is enzymatically digested, it generates a number of peptides, which is beyond the resolving power of liquid chromatography and mass spectrometry systems, making the analysis of all proteolytic peptides impracticable. Nevertheless, the sequence of a peptide of at least 7 residues, obtained by the cleavage of a protein with a highly specific protease, is sufficient for the identification of the protein.

The analysis of a small number of peptides per protein is often accomplished by the specific isolation of peptides containing low abundance amino acid. However, it is also possible to achieve such a goal taking into consideration physical features of the peptides, and excluding from the analysis those peptides containing well-distributed as well as low abundance amino acid within the protein sequence, for example peptides that contain histidine and arginine residues.

In this sense, the present invention provides a method for the selective isolation of peptides that do not contain histidine neither arginine residues (NHNR peptides) based on ion exchange chromatography of proteolytic peptides previously modified by covalent derivatization of α-amino terminal groups and ε-amino groups of lysines residues. The present method of invention can be used efficiently in the identification of proteins in a complex mixture, and in the determination of the ratio of expression levels of one or more proteins in two different samples since all the proteins contain NHNR peptides.

In a specific embodiment of the methods herein, a polypeptide mixture, which may be generated from a variety of natural or synthetic sources, is subjected to the steps illustrated in FIG. 1 and are explain as follows:

(1) Alkylation of cysteines with any known alkylating reagent i.e. iodoacetamide, iodoacetic acid or acrylamide. This is particularly useful for tightly folded protein(s) due to disulfide bridges formation or for protein containing free cysteines residues. For the fist case the cysteine alkylation assists in the enzymatic digestion process and for the second case it would avoid the formation of dimers and other adducts through disulfide/dithiol exchange reactions.

(2) Hydrolysis of the proteins. This goal is achieved by the enzymatic digest with endoproteinase Glu-C, endoproteinase Asp-N, endoproteinase Lys-C, trypsin, quimotrypsin, termolisin, pepsin, papain, pronase or any other protease. The chemical hydrolisis of protein with cyanogen bromide or with organic or anorganic acids could also be employed. In addition, peptide mixtures subjected to the method of this invention may be the results of the combination of enzymatic and/or chemical procedures such as those mentioned above. Peptides thus generated, preferably range in size from about 10 to 50 amino acids in length and are more preferable to facilitate peptide sequencing using tandem mass spectrometric methods. Those of ordinary skill in the art can select a protein digestion protocol suitable for use in the protein sample(s) of interest.

(3) Covalent modification of α-amino terminal groups and ε-amino groups of lysine side chains. A variety of useful amine protective groups are known in the art and readily available for application in this method. The protective group selected must no contains or generate basic groups nor possible sites for protonation. The list of reagents that could be used includes: acetic anhydride, N-hidroxysuccinimide, N-acetoxysuccinamide, citraconic anhydride, maleic anhydride, succinic anhydride, phtalic anhydride, tetrahidroftalic anhydride and 9-fluorenylmethyl chloroformate. Some other suitable N-terminal amino protecting groups are: (a) aromatic urethane-type protecting groups which include benzyloxycarbonyl, 2-chlorobenzyloxycarbonyl, 9-fluorenylmethyloxycarbonyl, isonicotinyloxycarbonyl and 4-methoxybenzyloxycarbonyl; (b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which include adamantyloxycarbonyl, cyclopentyloxycarbonyl, cyclohexyloxycarbonyl and isobornyloxycarbonyl; (d) acyl protecting groups or sulfonyl protecting groups. Preferred protecting groups include benzyloxycarbonyl, t-butoxycarbonyl, acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl; (e) photosensitive protective groups which include carbamates derivatives from m-nitrophenyl, 3,5-dimetoxybenzyl, 1-methyl-1(3,5-dimetoxyphenyl)etyl, α-methylnitropiperonyl, o-nitrobenzyl, 3,4-dimetoxy-6-nitrobenzyl, phenyl(o-nitrophenyl)methyl, 2-(2-nitrophenyl)etyl, 6-nitroveratryl, 4-metoxyfenacyl and 3',5'-dimetoxybenzoine.

Any method and/or reagents that achieve the function of selective derivatization of amino groups are intended to be encompassed by this invention. Examples of reagents and protocols for making such modification are easily find in the literature (Protective groups in organic synthesis, Teodora W. Greene and Peter G. M. Wuts, pag. 494-654, Ed. John Wiley & Sons, Inc. (1990) and Peptide Chemistry, Bodanszky, N., pag. 74-103, Springer-Verlag, N.Y. (1988)).

(4) Ion exchange chromatography of the mixture of modified peptides. The selection of peptides is accomplished by a strong cation exchange chromatography at pH 2-4. The acidic conditions include the use of formic acid, trifluoroacetic acid or any other buffer system, which gives the desired pH of work. This chromatographic step readily separates non-charged from single and double charged peptides. The charged peptides are retained by the exchanger while NHNR peptides, are collected in the flow through.

5) Regeneration of α-amino terminal groups and ε-amino groups of lysines. This is an optional step which greatly depends on the amino group modifier initially employed. If maleic or citraconic anhydride were used as modifying agents, the free amino groups could be restored by timed incubation in the same acid conditions employed during the cation exchange chromatography. For the case of reagents used in the peptide synthesis for the transitory protection of amino groups, the protective groups could generally be removed using basic conditions. If the modifier agent has a photosensitive properties, it could be eliminated by light irradiation of modified peptides.

The method of this invention as specifically exemplified employs steps of washing peptides on reverse phase columns to remove undesired materials from the peptide sample.

The determination of differences in concentration of one or more proteins in different samples is achieved through the mass spectra analysis of isolated NHNR peptides isotopically labeled in three different ways:

a) The proteins are extracted from tissues or cell cultures grown in media with two isotopic version of certain nutrient. Among isotopically labeled nutrients could be used the fundamental source of nitrogen labeled with $^{14}N/^{15}N$, and essential amino acids labeled with isotopes of hydrogen ($^{1}H/^{2}H$), nitrogen ($^{14}N/^{15}N$), carbon ($^{12}C/^{13}C$), oxygen ($^{16}O/^{18}O$), etc. After the protein extraction, at least a portion of the samples are mixed to yield a combined sample which is treated according to the step 1-5 of the method for the selective isolation of NHNR peptides explained above.

b) The protein samples are separately hydrolyzed as in the step 2 of the method in buffer solutions prepared one of them with normal water while the other one contains $H_2{}^{18}O$. After that, at least a portion of the samples are mixed to yield a combined sample which is treated according to the steps 3-5 of the method for the selective isolation of NHNR peptides explained above.

c) The protein samples are separately hydrolyzed as in the step 2 of the method, and the generated peptides are modified with different isotopic versions, of the same amino modifier reagent, according to the step 3 of the method. The mixture of both samples consists of peptides of the same chemical nature but isotopically different due to the isotopic version of the amino modifier reagent used, for instance H/D, $^{12}C/^{13}C$, $^{14}N/^{15}C$ $^{16}O/^{18}O$, etc. Next, NHNR peptides are isolated by cation exchange chromatography as explained above.

In any of the three exposed labeling techniques, the isolated NHNR peptides are analyzed by mass spectrometry. The concentration ratio between the analyzed proteins is determined from the areas ratios of the estimated theoretical spectra for differentially labeled NHNR peptides.

The theoretical spectrum is estimated from the lineal combination of the isotopic distributions of the NHNR peptides which better fit to the observed spectrum. This combination indicates the peptide contribution to the envelope of the observed spectrum. The ratio of areas is equivalent to the ratio of contributions if the isotopic distributions areas are normalized.

The compounds present in the analyzed m/z range can be sorted out in three groups: 1) the NHNR peptide species, coming from the first sample, 2) the NHNR peptide species, coming from the second sample, 3) a compound without interest for the present analysis.

The ratio of the total contribution of the NHNR peptide species of interest, coming from each sample, represents the ratio of concentration of the proteins in each sample. Any interference caused by the overlapping of other uninteresting compounds signals, can be equally considered by the theoretical spectra estimation, providing robustness and generality to this quantification method.

The isotopic distribution calculation considers the elemental composition of the NHNR peptides and any particular isotopic enrichment. This, along with the analysis of the signal overlapping, decouples the method from a particular isotopic labeling.

During labeling in the presence of $H_2{}^{18}O$, peptides prompted to deamidation such as those containing asparagine, glutamine or carbamidomethylcystein residues, might incorporate an additional $^{18}O$. This produces a wider isotopic distribution for the NHNR peptides coming from the $^{18}O$ labeled sample, misguiding any method which estimate the light/heavy ratio based only on the first two peaks from the isotopic distribution. The estimation of the theoretical spectrum allows extracting the information provided by the composition of isotopic distributions of the NHNR peptides which better fit to the observed spectrum. The information contained in the isotopic distribution is highly restrictive, allowing estimating the noise with high precision.

Mass spectrometers based on Electrospray (ESI-MS) or Matrix Assisted Laser Desorption Ionization (MALDI-MS) as ionization sources, could be employed in the analysis. The information thus provided is useful in determining the peptides amino acid sequences and their corresponding proteins through database search.

The following references relate to the application of mass spectrometric techniques to protein identification, particularly those related to proteome analysis: Ideker T, Thorsson V, Ranish J A, Christmas R, Buhler J, Eng J K, Bungarner R, Goodlett D R, Aebersold R, Hood L "Integrated genomic and proteomic analyses of a systematically perturbed metabolic network." Science. May 4, 2001;292(5518):929-34; Gygi S P, Aebersold R. "Mass spectrometry and proteomics." Curr Opin Chem Biol. October 2000;4(5):489-94.; Gygi S P, Rist B, Aebersold R "Measuring gene expression by quantitative proteome analysis" Curr Opin Biotechnol." August 2000;1 1(4):396-401; Goodlett D R, Bruce J E, Anderson G A, Rist B, Pasa-Tolic L, Fiehn O, Smith R D, Aebersold R. "Protein identification with a single accurate mass of a cysteine-containing peptide and constrained database searching." Anal Chem. Mar. 15, 2000;72(6):1112-8.; and Goodlett D R, Aebersold R, Watts J D. "Quantitative in vitro kinase reaction as a guide for phosphoprotein analysis by mass spectrometry." Rapid Commun Mass Spectrom. 2000;14(5):344-8; Zhou, H. et al (April 2001) Nature Biotechnol. 19:375-378.

Obtaining peptide structural information could be explained as follows. In a first stage of a tandem mass spectrometer, any given NHNR peptide is selected and subjected to a collision-induced dissociation (CID) experiment. The resulting fragment ions spectrum is recorded in a second stage of the mass spectrometer, as a so-called CID or MS/MS spectrum. Because the CID process usually causes fragmentation at peptide bonds along the peptide chain, the CID spectrum alone often provides enough information to determine a peptide sequence.

The sequence of the isolated peptides and the identification of proteins can be determined by a combination of tandem mass spectrometry and computer-assisted database search programs, such as MASCOT (Matrix Science Ltd, UK) (Perkins, D N, et al. (1999) "Probability-based protein identification by searching sequence databases using mass spectrometry data" *Electrophoresis* 20, 3551-3567) or SEQUEST (Trademark, University of Washington, Seattle Wash.) (McCormack, A. L. et al. (1996) "Direct Analysis and Identification of Proteins in Mixtures by LC/MS/MS and Database Searching at the Low-Femtomole Level", Anal. Chem. 69, 767-776; Eng, J. K. et al. (1994) "An Approach to Correlate Tandem Mass Spectral Data of Peptides with Amino Acid Sequences in a Protein Database" J. Amer. Soc. Mass. Spectrom., 5, 976-989; U.S. Pat. No. 5,538,897 (Jul. 23, 1996) Yates, III et al.). Both, MASCOT and SEQUEST takes all known genomic sequence, computes all possible theoretical CID spectra and compares them to experimental CID spectra for matches and sequence identification.

The protein identification process using the method of this invention could be greatly assisted with the use of genomic database of NHNR peptide sequences. Such databases would allow a fast and more reliable search using the MASCOT and/or SEQUEST programs, minimizing the possibilities of false positive identifications.

Once the NHNR peptides have been identified it is possible to determine the relative concentrations of the proteins, from the MS/MS spectra. This could be done by analyzing the isotopic distributions of the fragment ions containing the light and heavy versions of the labeling.

A) Mass spectra corresponding to the selective isolation of NHNR peptides from the mixture of both samples.

(B), (C) y (D) Expanded mass ranges for the m/z signals 725.83, 908.46 y 1081.60 corresponding to the proteins human alpha-2b interferon, horse myoglobin and recombinant streptokinase, respectively. These signals contain the typical isotopic distributions of the inclusion of $^{16}O$/$^{18}O$ at the C-termini of every peptide. It could also be observed the contribution to the estimated theoretical spectrum of the present peptide species according to the following representation:

IIII Observed Spectrum

Figure 4:
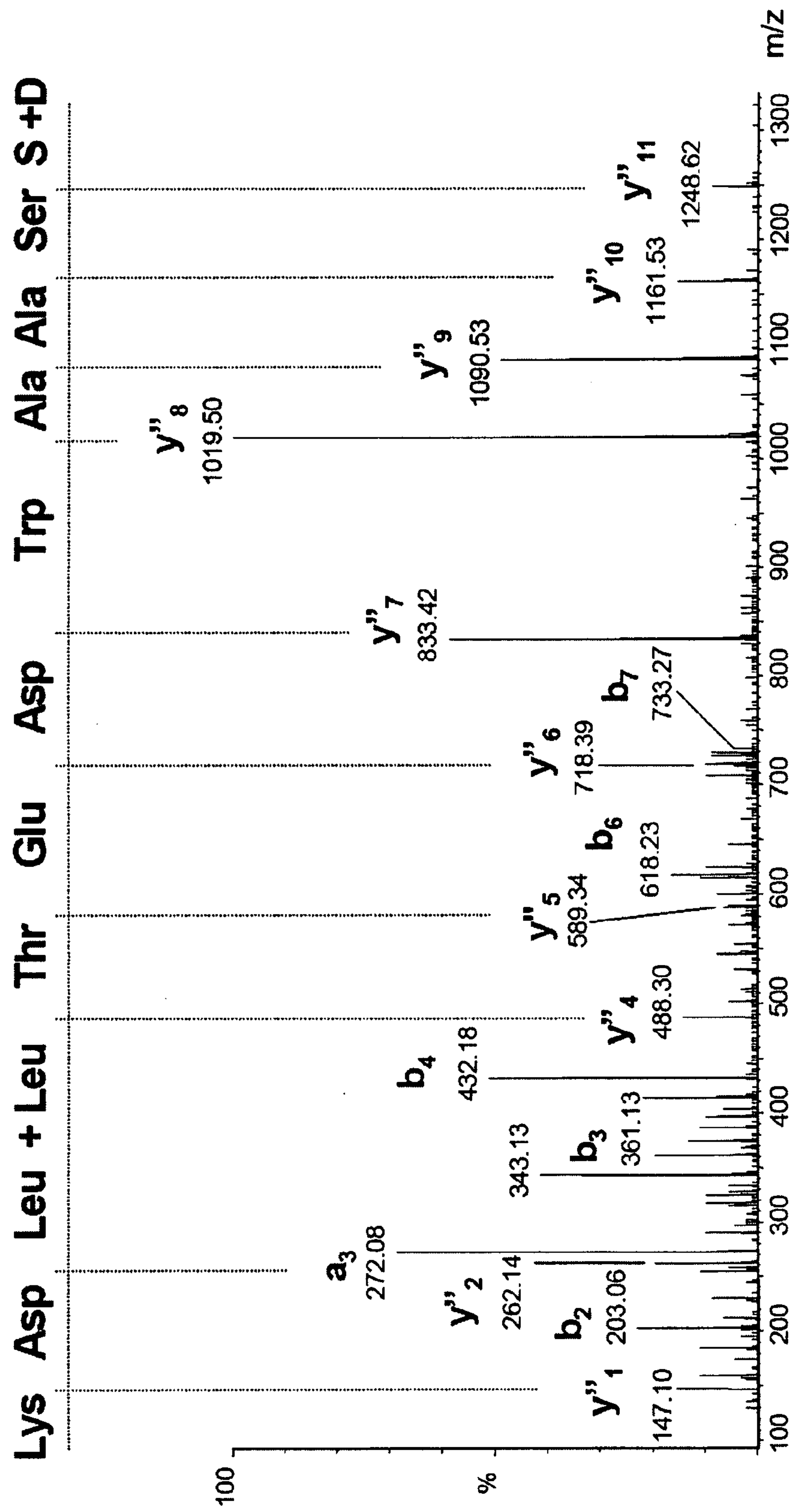

Contribution of each present peptide specie to the total estimated spectrum:

$^{16}O$ labeled labeled with one $^{18}O$ atom labeled with two $^{18}O$ atoms $^{16}O$ labeled and one desamidation $^{16}O$ labeled and two desamidation labeled with one $^{18}O$ atom and one desamidation labeled with one $^{18}O$ atom and two desamidations labeled with two $^{18}O$ atoms and one desamidation labeled with three $^{18}O$ atoms and one desamidation Theoretical total estimated spectrum which includes each peptide specie FIG. 4. MS/MS spectrum of the NHNR peptide of m/z 725.83 automatically assigned by the MASCOT program to the sequence DSSAAWDETLLDK corresponding to the protein human alpha 2b interferon. The N- and C-terminal ions are denoted in the spectrum according to the nomenclature proposed by Roepstorff P. and Fohlman J. (Proposal for a common nomenclature for sequence ions in mass spectra of peptides. Biomed Mass Spectrom. 11, 984, p.601)

EXAMPLES

Example 1

NHNR Peptide Isolation from Recombinant Streptokinase

Figure 1:
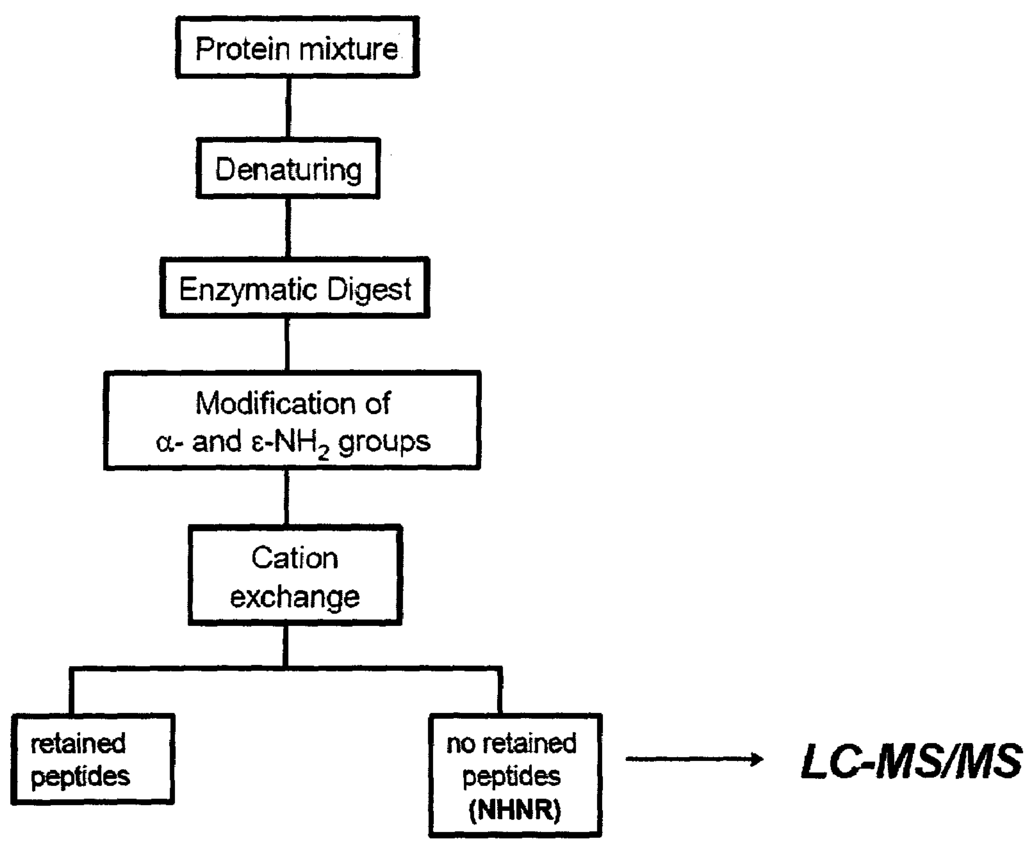
FIG. 1. Scheme depicting the selective isolation of peptides by the method of this invention.

Recombinant streptokinase was subjected to the method shown in FIG. 1 according to the following steps. 1) Hydrolysis for 6 hours at 37° C. with trypsin in 0.1 M HEPES buffer,pH 8.6, urea 4M. 2) Citraconic anhydride was added in a 50 molar excess over amino groups. The reactions proceed for 15 min at 4° C. 3) Excess of reagent was removed by desalting of peptides by HPLC using a RP-C4 column (20×2.1 mm), and a solvent system consisting of solvent A: 0.05% TFA in water and solvent B: 0.05% TFA in acetonitrile. 4) Modified peptides were loaded onto a strong cation exchanger and the flow-through fraction was immediately collected. 5) Isolated peptide fraction was incubated for 12 hours at 37° C. in order to remove the citraconyl groups and further analyzed by mass spectrometry.

Figure 2A:
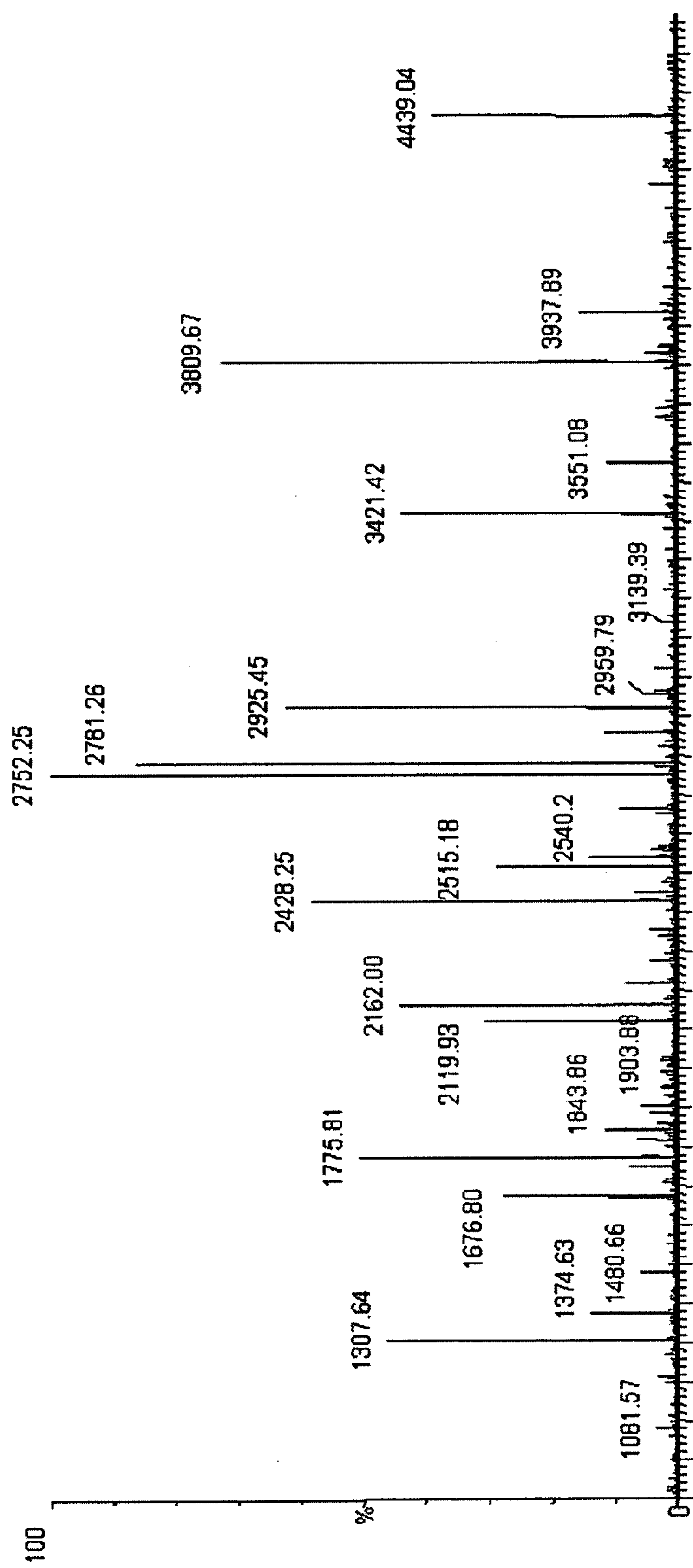
FIG. 2. Results of the selective isolation of NHNR peptides from the protein recombinant streptokinase. The LEP digest of the protein was analyzed by ESI-MS before (A) and after (B) the application of the method of this invention.
Figure 2B:
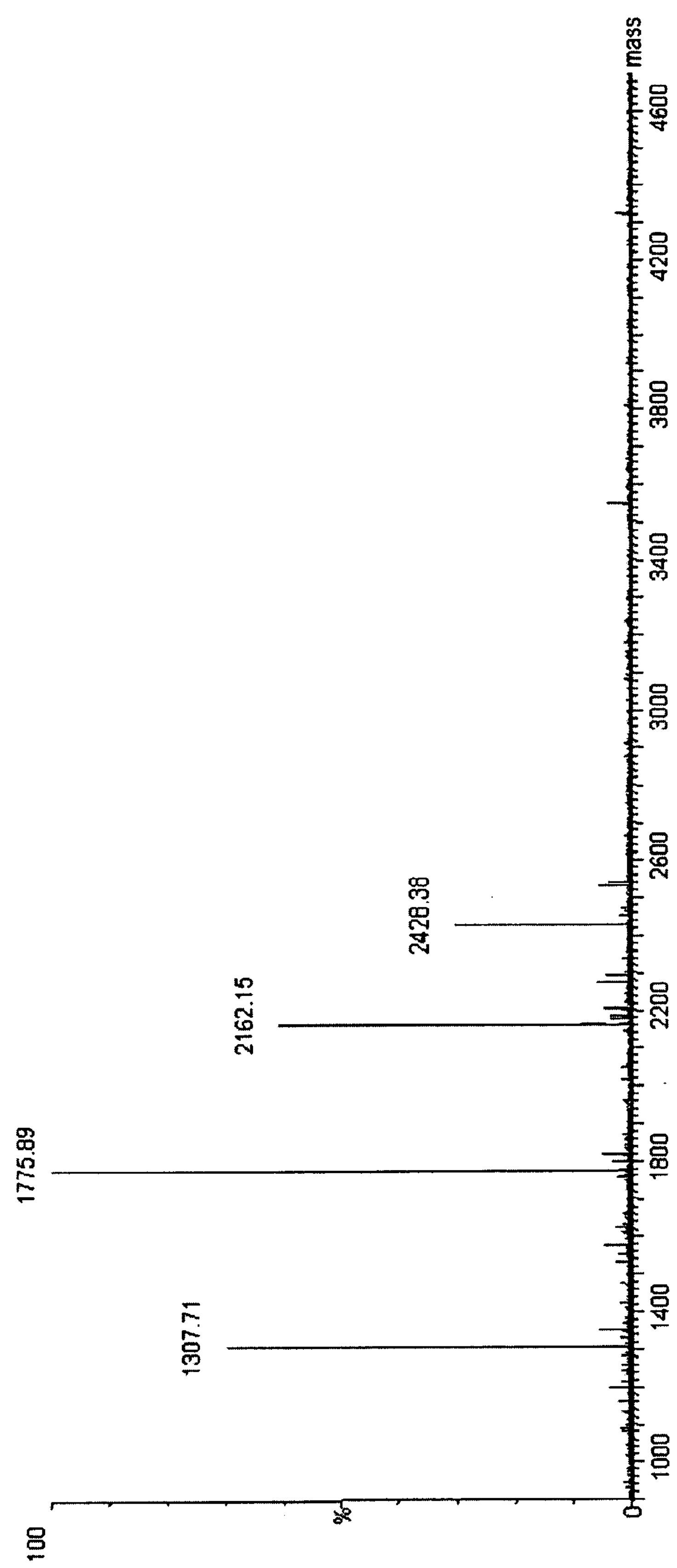

The ESI-MS of the entire digest of the protein is shown in the FIG. 2A. Subjecting the streptokinase digest to the NHNR peptide isolation procedure, considerably reduced sample complexity, yielding only 4 peptides (FIG. 2B). Table 1 exhibits the m/z values of isolated peptides and its assignment to the protein sequence (sequence #1 at the end of the document).

TABLE 1

Observed and calculated m/z values for the isolated peptides from the protein recombinant streptokinase according to the method of this invention.

| (M + H) obs | (M + H) cal | Sequence |
|---|---|---|
| 1307.71 | 1307.68 | 300-310 |
| 1775.89 | 1775.87 | 259-274 |
| 2162.15 | 2162.08 | 336-354 |
| 2428.38 | 2428.33 | 188-210 |

Example 2

Identification of proteins present in a membrane extract from the *Neisseria meningitidis* bacteria using the selective isolation of NHNR peptides.

The *Neisseria meningitidis* bacteria culture was grown during 16 hours and after that it was centrifuged at 5000 g for 15 min. The biomass was extracted with a buffer solution consisting in 0.1 M Tris-HCl pH 8.5, 10 mM EDTA and 0.5% sodium deoxicolate during 30 min at room temperature with constant agitation. Then, it was centrifuged at 20000 for 30 min at 4° C. and the supernatant was collected. Another extraction step was conducted over the pellet with the same buffer solution as above. This sample and the previously collected supernatant were mixed and further ultracentrifuged at 125000 for 2 hours at 4° C. The pellet was dissolved in 50 mM Tris-HCl, 2 mM EDTA, 1.2% sodium deoxicolate and 20% sucrose and the solution was subjected to another ultracentrifugation step. Finally, the protein pellet was homogenized in solution containing 3% sucrose and 0.01% tiomersal.

The extract of proteins (300 μg) were dissolved in 0.1 M HEPES buffer (pH 8.8), guanidinium chloride 6M, and the mixture was reduced and alkylated by addition of DTT (10 mM, 2 hours) followed by 1 hour of incubation with iodoacetamide. The sample were then diluted prior to digestion for 16 hours with trypsin at 37° C. The resulting peptide mixture was treated essentially as in example 1.

Isolated peptides by this method were analyzed by LC-MS/MS and the MS/MS spectra were recorded for database search identification of proteins. The table 2 shows the list of identified peptides and their corresponding proteins or genes. Nearly 40% of the identified proteins (58 in total) are localized in the bacteria membrane. Half of these proteins could not be detected in a previous study using two dimensional gel electrophoresis (results not shown). This perfectly agrees with the fact that membrane proteins are poorly represents when current two dimensional electrophoresis procedures are used.

TABLE 2

Proteins and peptides identified in the membrane extract from the *Neisseria meningitidis* bacteria using the method of this invention.

| Protein name | Access number to TREMBL or SWISSPROT | Protein # | Identified Peptide (initial amino acid-final amino acid) |
|---|---|---|---|
| outer membrane protein class 1 | Q9S4V0 | 2 | 67-77 |
| | | | 78-87 |
| | | | 225-235 |
| | | | 336-355 |
| outer membrane protein class 3 | P30690 | 3 | 64-73 |
| | | | 129-136 |
| | | | 118-128 |
| | | | 20-28 |
| | | | 185-197 |
| | | | 60-73 |
| outer membrane protein class 5c | Q9AE79 | 4 | 171-179 |
| | | | 186-199 |
| | | | 201-214 |
| outer membrane protein P64k | Q51225 | 5 | 87-99 |
| | | | 44-57 |
| | | | 367-381 |
| outer membrane protein class 4 | P38367 | 6 | 103-109 |
| | | | 56-102 |
| outer membrane protein Omp85 | Q9K1H0 | 7 | 146-153 |
| | | | 772-779 |
| | | | 687-701 |
| Fe-regulated protein B precursor - *Neisseria meningitidis* | Q9JXL3 | 8 | 130-148 |
| | | | 298-304 |
| | | | 633-643 |
| | | | 305-314 |
| | | | 29-37 |
| | | | 656-671 |

TABLE 2-continued

Proteins and peptides identified in the membrane extract from the *Neisseria meningitidis* bacteria using the method of this invention.

| Protein name | Access number to TREMBL or SWISSPROT | Protein # | Identified Peptide (initial amino acid-final amino acid) |
|---|---|---|---|
| Major ferric iron binding protein precursor (FBP) | P17940 | 9 | 142-150 |
| | | | 324-331 |
| | | | 266-274 |
| transferrin-binding protein 1 | Q09056 | 10 | 738-746 |
| | | | 800-810 |
| lactoferrin-binding protein A | O87343 | 11 | 483-493 |
| | | | 837-847 |
| hemoglobin receptor | Q9JYA8 | 12 | 600-605 |
| | | | 626-635 |
| | | | 636-644 |
| | | | 700-707 |
| | | | 711-717 |
| ATP synthase F1, beta subunit | Q9JXQ2 | 13 | 144-154 |
| ATP synthase F1, alpha subunit | Q9JXQ0 | 14 | 141-155 |
| ABC transporter, ATP-binding protein | Q9K112 | 15 | 36-46 |
| Opacity protein | O30756 | 16 | 159-166 |
| | | | 156-173 |
| putative pilus assembly protein | Q9JY02 | 17 | 72-88 |
| | | | 95-115 |
| Pilus secretin | Q9JVW4 | 18 | 426-441 |
| organic solvent tolerance protein, putative | Q9K187 | 19 | 359-369 |
| | | | 152-170 |
| surface protein A | Q9RP17 | 20 | 80-98 |
| pyruvate dehydrogenase, E2 component dihydrolipoamide acetyltransferase | Q9JZ11 | 21 | 364-372 |
| Elongation factor Tu | Q9JRI5 | 22 | 26-38 |
| Elongation factor G (EF-G) | Q9K1I8 | 23 | 190-198 |
| glyceraldehyde 3-phosphate dehydrogenase | Q9JX95 | 24 | 216-227 |
| alcohol dehydrogenase, propanol-preferring | Q9K0P0 | 25 | 3-10 |
| proline dehydrogenase | Q9K0Z9 | 26 | 996-1004 |
| 6-phosphogluconate dehydrogenase, decarboxylating | Q9K1Q5 | 27 | 38-47 |
| peroxiredoxin 2 family protein/glutaredoxin | Q9JQS4 | 28 | 220-230 |
| malate: quinone oxidoreductase | Q9JXD7 | 29 | 186-194 |
| aspartyl-tRNA synthetase | Q9JT23 | 30 | 376-383 |
| phosphoenolpyruvate synthase | Q9K012 | 31 | 527-533 |
| citrate synthase | Q9JQX0 | 32 | 275-293 |
| recA protein | P56988 | 33 | 287-297 |
| | | | 199-216 |
| 5-methyltetrahydropteroyltriglutamate-homocysteine methyltransferase | Q9JZQ2 | 34 | 298-308 |
| phospholipase A1, putative | Q9K0U7 | 35 | 181-187 |
| adenylosuccinate lyase | Q9K183 | 36 | 146-152 |
| oxoacyl-(acyl-carrier-protein) synthase III | Q9K1D8 | 37 | 131-152 |
| aconitate hydratase, Putative | Q9X5I6 | 38 | 615-622 |
| Succinyl-CoA synthetase beta chain | Q9JZP4 | 39 | 281-296 |
| homoserine dehydrogenase | Q9JR84 | 40 | 172-180 |
| stringent starvation protein A | Q9JXN8 | 41 | 23-30 |
| orotate phosphoribosyltransferase | Q9JR25 | 42 | 20-26 |
| Glutamate dehydrogenase, NADP-specific. | Q9JY71 | 43 | 105-113 |
| IgA1 protease | Q51169 | 44 | 1376-1386 |
| | | | 1503-1515 |
| | | | 1490-1502 |
| 30S ribosomal protein S2 | Q9JRG7 | 45 | 118-131 |
| | | | 65-73 |
| | | | 226-266 |
| 30S ribosomal protein S3 | Q9JQX2 | 46 | 26-34 |
| | | | 80-88 |
| 30s ribosomal protein S5 | Q9JQP3 | 47 | 96-102 |
| 30S ribosomal protein S10 | Q9JR21 | 48 | 38-45 |
| 30S ribosomal protein S11 | Q9JQR2 | 49 | 60-74 |
| 30S ribosomal protein S17 | Q9JQL7 | 50 | 74-83 |
| 50S ribosomal protein L14 | Q9JQY4 | 51 | 79-90 |

TABLE 2-continued

Proteins and peptides identified in the membrane extract from the *Neisseria meningitidis* bacteria using the method of this invention.

| Protein name | Access number to TREMBL or SWISSPROT | Protein # | Identified Peptide (initial amino acid-final amino acid) |
|---|---|---|---|
| 50S ribosomal protein L1 | Q9JRJ1 | 52 | 142-154 |
| 50S ribosomal protein L6 | Q9K1I3 | 53 | 19-27 |
| 50S ribosomal protein L16 | Q9JR26 | 54 | 27-35 |
| 50S ribosomal protein L25 | Q9JZW3 | 55 | 165-175 |
| 50S ribosomal protein L15 | Q9K1I2 | 56 | 97-109 |
| 50S ribosomal protein L22 | Q9JRD8 | 57 | 28-41 |
| 50S ribosomal protein L9 | Q9JZ31 | 58 | 72-82 |
| 50S ribosomal protein L11 | Q9K1J3 | 59 | 73-81 |

From table 2 it could be observed that out of the 95 positively identified peptides only one contains an arginine residue. These results probed the high degree of selectivity that could be achieved with the present method. On the other hand, 20 identified proteins (34%) do not contain cysteine, which means that could have not been detected using methods based on the selective isolation of cysteine residues. (Quantitative analysis of complex protein mixtures using isotope-coded affinity tags. Gygi, S. P., Rist, B., Gerber, S. A., Turecek, F., Gelb, M. H., and Aebersold, R. *Nat. Biotechnol.* 17, 994-999, 1999; Simplification of complex peptide mixtures for proteomic analysis: reversible biotinylation of cysteinyl peptides. Spahr C S, Susin S A, Bures E J, Robinson J H, Davis M T, McGinley M D, Kroemer G, Patterson S D. Electrophoresis, 21(9), 1635-1650, 2000). This fact affords for a broader application of the present invention.

for myoglobin and 1:4 for the alpha interferon. The isolation of NHNR peptides was achieved essentially as in the example 1, but for this case the enzymatic digestion with trypsin was carried out in the presence of normal water for the mixture A while the mixture B was hydrolyzed in presence of $H_2{}^{18}O$. Both samples were mixed and the NHNR peptides were isolated according to the method of this invention.

The enzymatic labeling with $^{16}O/^{18}O$ was chosen due to the increasing level of complexity that this labeling procedure may introduce. For instance, it does not produce enough separation between the mass signals to avoid the overlapping of the peptides isotopic envelops. Additionally, the incorporation of one or two $^{18}O$ atoms creates a complex pattern which makes more difficult the quantification analysis.

The isolated NHNR peptides were sequenced and quantified in a single LC-MS/MS experiment. This allows an unambiguous identification of the three proteins present in the mixture as well as their precise quantification with less than 14% of error (table 3).

TABLE 3

Identification and quantitative analysis of the proteins in the mixtures A and B by selective isolation of NHNR peptides labeled with $^{16}O$ and $^{18}O$, respectively.

| Protein | Protein No. | Identified Peptide (initial amino acid - final amino acid) | m/z (charge) | Observed $^{16}O/^{18}O$ relation | Mean Value $^{16}O/^{18}O$ | Expected $^{16}O/^{18}O$ Relation | Desviation | % error |
|---|---|---|---|---|---|---|---|---|
| Streptokinase | 1 | 300-310 | 654.35 (+2) | 0.933 | 1.04 | 1 | 0.09 | 4 |
| | | 2549-274 | 888.43 (+2) | 1.010 | | | | |
| | | 336-354 | 1081.55 (+2) | 1.22 | | | | |
| | | 336-354[(a)] | 1082.04 (+2) | 0.93 | | | | |
| | | 336-354[(b)] | 1082.54 (+2) | 1.39 | | | | |
| | | 188-210 | 1214.69 (+2) | 1.126 | | | | |
| | | 188-210 | 810.11 (+3) | 0.952 | | | | |
| Myoglobin | 60 | 1-16 | 908.46 (+2) | 1.872 | 1.87 | 2 | 0.13 | 6.5 |
| Alpha interferon | 61 | 71-83 | 725.83 (+2) | 3.46 | 3.46 | 4 | 0.54 | 13.5 |

[(a)]Peptide with one desamidated asparagine.
[(b)]Peptide with two desamidated asparagines

Example 3

Identification and relative quantification of the proteins components of the two mixtures (A and B) by the method of this invention.

The samples A and B where prepared with the proteins recombinant streptokinase, horse myoglobin and human alpha-2b interferon. The three proteins were mixed in a molar ratio of A respected to B of 1:1 for streptokinase, 1:2

Figure 3A:
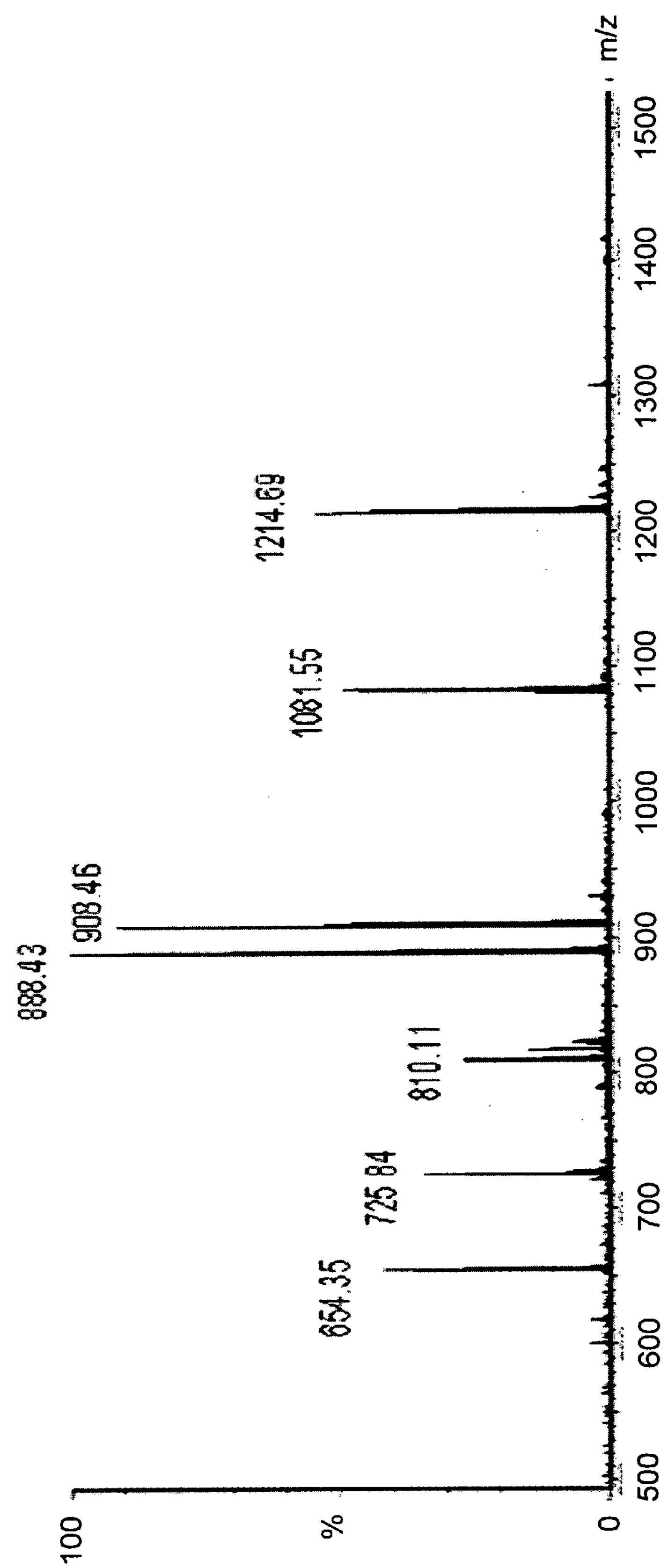
FIG. 3 Mass spectra obtained after the application of the method of this invention to the mixture of proteins A and B which were digested in the presence of $H_2{}^{16}O$ y $H_2{}^{18}O$ respectively. The mixtures were composed by the proteins recombinant streptokinase, horse myoglobin and human alpha-2b interferon. The concentration ratios of the proteins recombinant streptokinase, horse myoglobin and human alpha-2b interferon in the mixture A respect to the mixture B were of 1:1, 1:2 and 1:4, respectively.
Figure 3B:
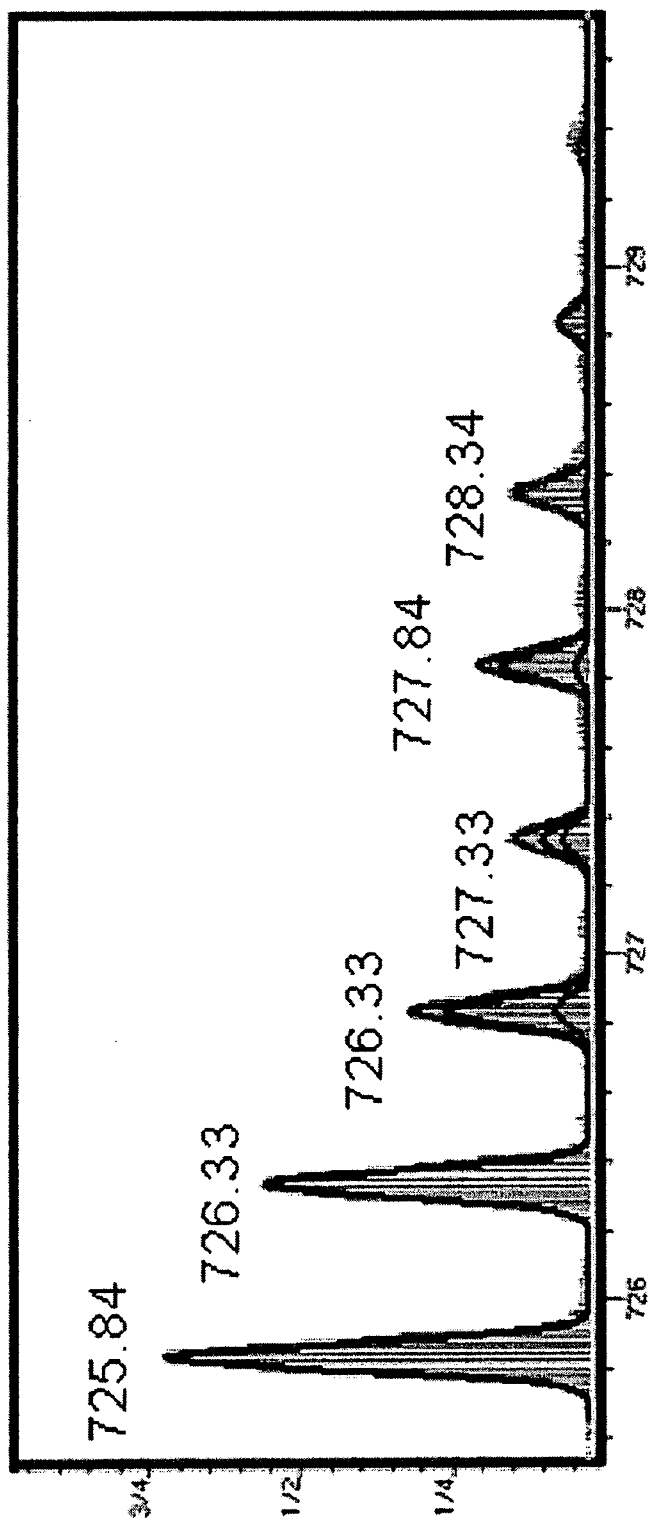
Figure 3C:
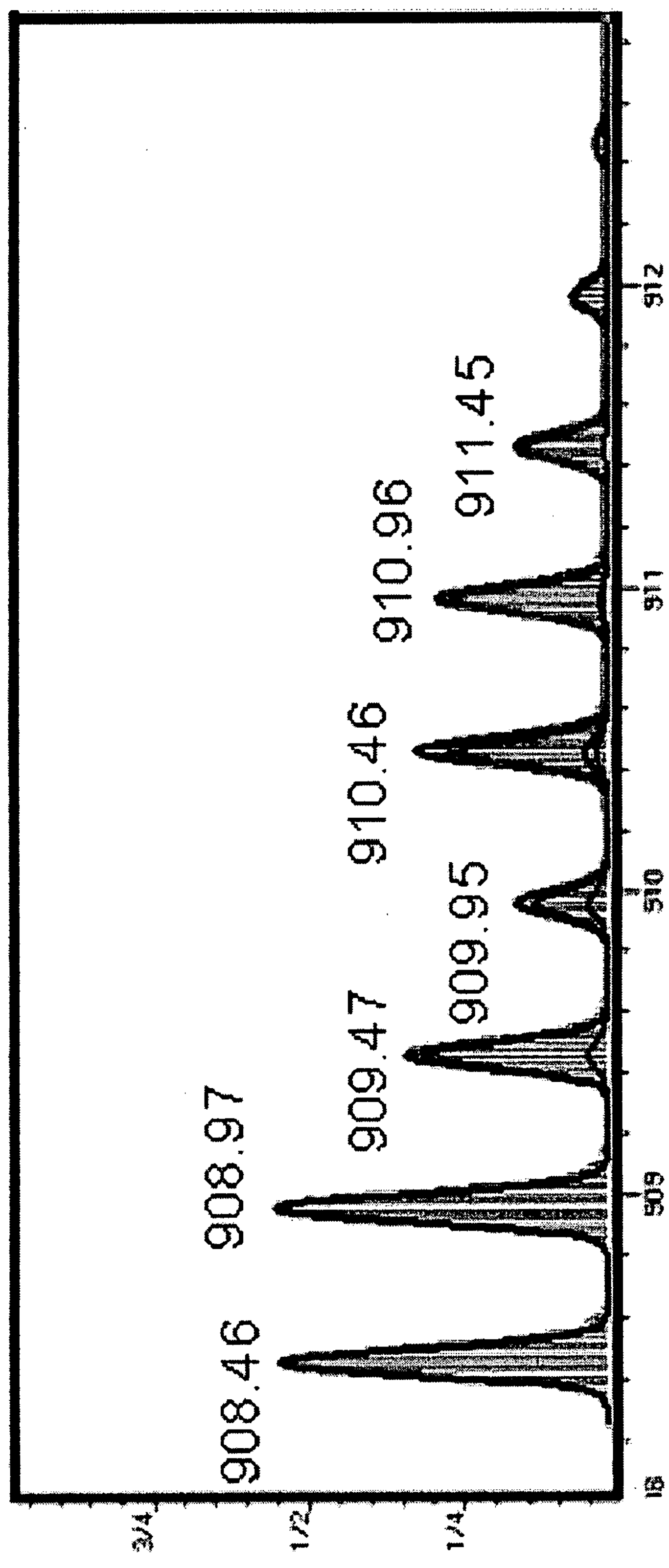
Figure 3D:
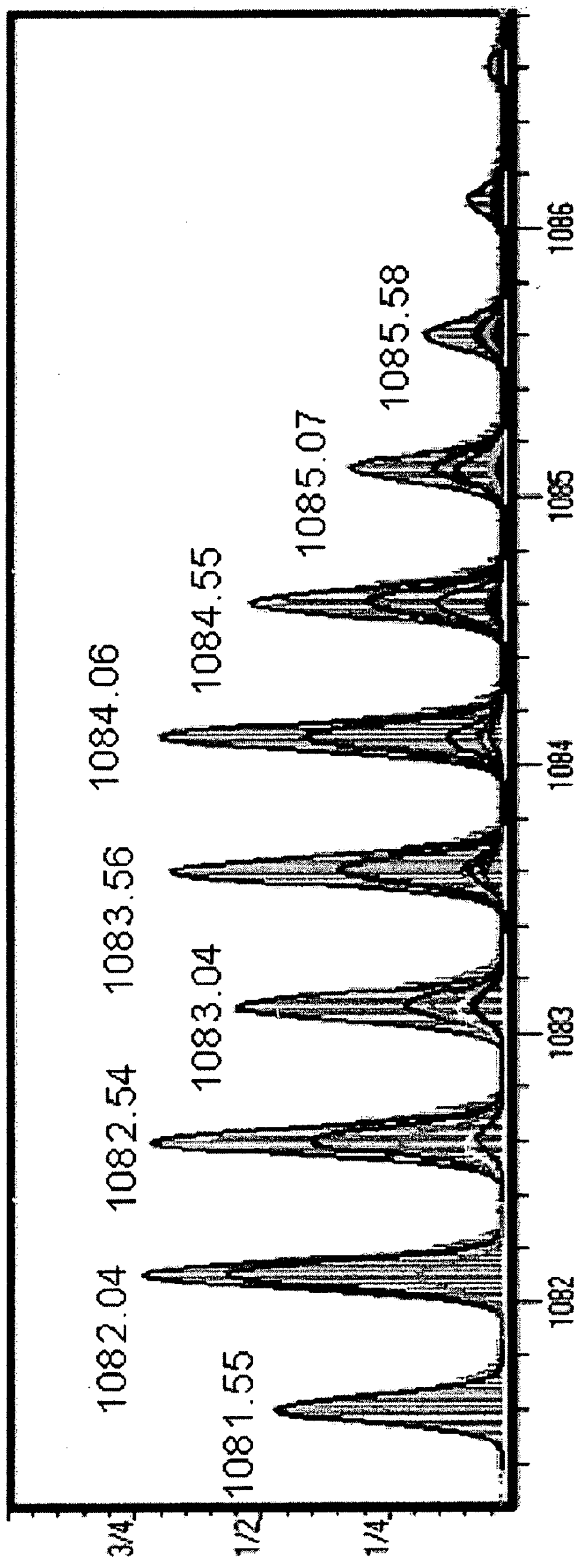

The FIG. 3A shows the mass spectrum corresponding to the isolation of NHNR peptides from the mixture of both samples. The FIGS. 3B, 3C and 3D shows the expanded ranges of the spectrum for the m/z signals 725.83, 908.46 and 1081.55 respectively, containing typical isotopic distributions of $^{16}O/^{18}O$ at the C-terminus of each peptide. Furthermore, it can be observed the contribution of each peptide specie and isotopic variants to the total theoretical spectrum. In the case of the peptide of m/z 1081.55 it could be identified and quantified the presence of asparagine deamidations which where also considered for the calculations of the relative concentrations of peptides labeled with $^{16}O/^{18}O$.

The quantitation procedure takes into account the possible deamidation of NHNR peptides according to their composition of Asn and Gln residues. The deamidation process occurring during the $H_2{}^{18}O$ exposition may introduces an additional atom of $^{18}O$ in the OH group that substitutes the $NH_2$ group of the Asn to form Asp. Hence, in addition to the $^{18}O$ atoms that are incorporated at the C-terminus of the peptides during the enzymatic hydrolysis, the NHNR peptides coming from the sample hydrolyzed in the presence of $H_2{}^{18}O$ might incorporate an additional $^{18}O$ in every Asn o Gin of the peptides.

For the spectra analysis, the theoretical isotopic distribution of each NHNR peptide are calculated and normalized including the isotopic variants and possible deamidations. The combination of the isotopic distributions that better matches to the observed spectra is estimated.

For each peptide it is calculated the ratio between the sum of areas of the isotopic envelops of the natural isotopic variants i.e. $^{16}O$ labeled species, and the sum of areas of the isotopic envelops of the $^{18}O$ enriched species. Due to the possible differences in the ionization efficiency of the peptide with Asn and the deamidated peptide containing Asp, the concentration ratio of their isotopic variant is separately calculated. For instance the peptide of m/z 1081.55 contains two Asn, and the calculations were made taking into account the areas of the isotopic envelopes of the three species of the peptides detected in the spectrum: 1) the peptide without deamidation, 2) with one deamidation and 3) with two de deamidation.

The application of the method of this invention to these samples resulted in the isolation and identification of 6 peptides, out of the 59 possible peptides that could be generated during the LEP hydrolysis of the mixture. This result shows the substantive simplification of the mixture composition obtained by this way. The mass spectrometry analysis is reduced to about 90% of the peptides, without detriment in the capacity to identify the proteins presents. For instance, the identification of the protein alpha interferon was feasible with the isolation of a single peptide with sequence DSSAAWDETLLDK and m/z 725.83 (FIG. 4).

LC-MS/MS and database search.

Mass spectrometric measurements were done in a hybrid quadrupole orthogonal acceleration tandem mass spectrometer QTof-2™ (Micromass, Manchester, UK). The mass spectrometer was connected online with a liquid chromatographer AKTA Basic (Amersham Pharmacia Biotech, Sweden) by using a RP-C18, 200×1 mm column (Vydac, USA). Peptides were eluted using a lineal gradient of solvent B ($CH_3CN$, 0.2% formic acid) from 5 to 45% in 120 min.

The capillary and cone voltages were set at 3000 and 35, respectively. Doubly and triply charged precursor ions to be fragmented were selected automatically once their intensity rose above a defined threshold (7 conts $sec^{-1}$). The MS/MS was switched to MS mode once the TIC decreased below 2 count $sec^{-1}$ or when MS/MS mode was achieved during 4 sec. Data acquisition and processing were performed using a MassLynx system (version 3.5) from Micromass.

Protein identification based on MS/MS spectra was made using the Internet available search engine Mascot. Search parameters included fixed (carbamidomethylcystein) and variable modifications, which included deamidation of asparagines and/or glutamines residues and oxidation of methionines.

What is claimed is:

1. A method for identification and quantification of one or more proteins in complex mixtures wherein the peptides not containing histidine nor arginine, named here NHNR peptides, are selectively isolated from each protein and a relative concentration of one or more proteins is determined from the ratio between the areas of estimated theoretical spectra for each NHNR peptide labeled with different isotopes in each sample, the method comprising the following steps:

a. enzymatically or chemically hydrolyzing the sample or samples of proteins;

b. chemically modifying alpha and epsilon amino groups ($\alpha$ and $\epsilon$-NH2) of every peptide obtained in step (a) with an agent that neither contains, nor generates positively charged groups, nor basic groups, nor possible sites of protonation;

c. isolating the NHNR peptides by cation exchange chromatography from the mixture of peptides obtained in step (b);

d. identifying proteins by mass spectrometry analysis of the NHNR peptides obtained in step (c);

e. differential isotopic labeling of protein samples previously to step (a) or during steps (a) or (b) and immediately mixing at least a portion of the samples; and f. relative quantifying one or more proteins in the mixtures of step (e) from the ratio between the areas of estimated theoretical spectra of the NHNR peptides identified in step (d), as well as from the ratio between the areas of the estimated theoretical spectra of fragments from the NHNR peptides, generated in step (d).

2. The method of claim 1 wherein the sample or samples of proteins in step (a) is a mixture of peptides or proteins from a cellular extract or biological fluid.

3. The method of claim 1 wherein the peptides are generated by enzymatic agents, chemical agents, or a combination thereof.

4. The method of claim 1, wherein the obtained peptides of step c) are fractionated by liquid chromatography or separation and concentration of analytes.

5. The method of claim 1, wherein the amino group modifier agents are selected from a group consisting of acetic anhydride, N-hidroxysuccinimide, N-acetoxysuccinamide, citraconic anhydride, maleic anhydride, succinic anhydride, phtalic anhydride, tetrahidroftalic anhydride and 9-fluorenylmethyl chloroformate, some other suitable N-terminal amino protecting groups are: (a) aromatic urethane-type protecting groups which includes benzyloxycarbonyl, 2-chlorobenzyloxycarbonyl, 9-fluorenylmethyloxycarbonyl, isonicotinyloxycarbonyl and 4-methoxybenzyloxycarbonyl; (b) aliphatic urethane-type protecting groups which includes t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which includes adamantyloxycarbonyl, cyclopentyloxycarbonyl, cyclohexyloxycarbonyl and isobornyloxycarbonyl; (d) acyl protecting groups or sulfonyl protecting groups, preferred protecting groups include benzyloxycarbonyl, t-butoxycarbonyl, acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl; (e) photosensitive protective groups which include carbamates derivatives from m-nitrophenyl, 3,5-dimetoxybenzyl, 1-methyl-1(3,5-dimetoxyphenyl)etyl, $\alpha$-methylnitropiperonyl, o-nitrobenzyl, 3,4-dimetoxy-6-nitrobenzyl, phenyl(o-nitrophenyl)methyl, 2-(2-nitrophenyl)etyl, 6-nitroveratryl, 4-metoxyfenacyl and 3', 5'-dimetoxybenzoine.

6. The method of claim 1, step (c), wherein NHNR peptides are obtained in the flow-through of the ion exchange chromatography.

7. The method of claim 6 wherein the NHNR peptides are physically, chemically or enzymatically treated to regenerate free $\alpha$- and $\epsilon$-amino groups.

8. The method of claim 6, wherein mass spectrometry or its combination with liquid chromatography is used to detect and identify the NHNR peptides and the proteins from where they were originated.

9. The method of claim 8 wherein the identification of the peptides present in the mixture is done by using the amino acid composition information of the NHNR peptides for their sequencing and/or identification in genomic databases of proteolytic digestions generated in advance.

10. The method of claim 1, step (f), wherein the relative concentration of one or more proteins present in the samples is determined from the ratio between the areas of the estimated theoretical spectra of the NHNR peptides isotopically labeled or from the ratio between the areas of the estimated theoretical spectra of fragments from NHNR peptides generated in the step (d).

11. The method of claim 10 wherein the theoretical spectra are estimated from the combination of isotopic distributions of the peptides molecular species detected that better match the observed spectra.

* * * * *